United States Patent
Brady et al.

(10) Patent No.: US 11,559,547 B2
(45) Date of Patent: Jan. 24, 2023

(54) NATURAL KILLER CELLS

(71) Applicant: IMPERIAL COLLEGE OF SCIENCE, TECHNOLOGY AND MEDICINE, London (GB)

(72) Inventors: Hugh J. M. Brady, London (GB); Matthew Fuchter, London (GB)

(73) Assignee: IMPERIAL COLLEGE INNOVATIONS LIMITED, London (GB)

( * ) Notice: Subject to any disclaimer, the term of this patent is extended or adjusted under 35 U.S.C. 154(b) by 241 days.

(21) Appl. No.: 16/490,258

(22) PCT Filed: Mar. 2, 2018

(86) PCT No.: PCT/GB2018/050542
§ 371 (c)(1),
(2) Date: Aug. 30, 2019

(87) PCT Pub. No.: WO2018/158587
PCT Pub. Date: Sep. 7, 2018

(65) Prior Publication Data
US 2019/0381102 A1    Dec. 19, 2019

(30) Foreign Application Priority Data
Mar. 3, 2017  (GB) .................................... 1703476

(51) Int. Cl.
| | | |
|---|---|---|
| A61K 35/17 | (2015.01) | |
| A61K 31/4725 | (2006.01) | |
| A61K 45/06 | (2006.01) | |
| C12N 5/0783 | (2010.01) | |

(52) U.S. Cl.
CPC .......... *A61K 35/17* (2013.01); *A61K 31/4725* (2013.01); *A61K 45/06* (2013.01); *C12N 5/0646* (2013.01); *C12N 2501/999* (2013.01); *C12N 2506/11* (2013.01)

(58) Field of Classification Search
None
See application file for complete search history.

(56) References Cited

U.S. PATENT DOCUMENTS

| | | | |
|---|---|---|---|
| 2007/0048290 A1 | 3/2007 | Tsai | |
| 2018/0280372 A1* | 10/2018 | Moley | A61K 31/167 |

FOREIGN PATENT DOCUMENTS

| | | |
|---|---|---|
| CN | 105596336 | 5/2016 |
| WO | 2011/080740 | 7/2011 |
| WO | 2012/128622 | 9/2012 |
| WO | 2013/033310 | 3/2013 |
| WO | 2015/052283 | 4/2015 |
| WO | 2015/103527 | 7/2015 |
| WO | 2018-178666 | 10/2018 |
| WO | 2020/002911 | 1/2020 |

OTHER PUBLICATIONS

Torrente et al., ACS Chemical Biology, 6: 131-134 (2011) (Year: 2011).*
International Search Report and Written Opinion of the International Searching Authority, dated Apr. 26, 2018 in corresponding International Patent Application No. PCT/GB2018/050542.
Gagnidze et al., "Nuclear receptor REV-ERBα mediates circadian sensitivity to mortality in murine vesicular stomatitis virus-induced encephalitis", PNAS, 113(20): 5730-5735 (2016).
Kojetin et al., "Identification of SR8278, a Synthetic Antagonist of the Nuclear Heme Receptor REV-ERB", ACS Chemical Biology, 6: 131-134 (2011).
Sukumaran et al., "Circadian rhythms in gene expression: Relationship to physiology, disease, drug disposition and drug action", Advanced Drug Delivery Reviews, 62: 904-917 (2010).
Seillet et al., "Differential Requirement for Nfil3 during NK Cell Development", J Immunol, 192: 2667-2676 (2014).
Search Report, dated Dec. 29, 2017 in corresponding GB application No. GB 1703476.0.
Dong et al., "A validated ultra-performance liquid chromatography-tandem mass spectrometry method to identify the pharmacokinetics of SR8278 in normal and streptozotocin-induced diabetic rats", Journal of Chromatography B, 1020: 142-147 (2016).
De Mei et al., "Dual inhibition of REV-ERBβ and autophagy as a novel pharmacological approach to induce cytotoxicity in cancer cells", Oncogene, 34: 2597-2608 (2015).
Davis et al., "Immunotherapeutic Applications of NK Cells". Pharmaceuticals, 2015, vol. 8, pp. 250-256.
Carter et al., "High Affinity Heme Binding to a Heme Regulatory Motif on the Nuclear Receptor Rev-erbβ Leads to Its Degradation and Indirectly Regulates Its Interaction with Nuclear Receptor Corepressor". The Journal of Biological Chemistry, Vo. 291, No. 5, pp. 2196-2222.
Altman et al., "MYC Disrupts the Circadian Clock and Metabolism in Cancer Cells", Cell Metabolism, Dec. 1, 2015, vol. 22, pp. 1009-1019.
Tang et al., "Smad3 promotes cancer progression by inhibiting E4BP4-mediated NK cell development", Nature Communications, 8:14677, pp. 1-15, Mar. 6, 2017.
Miller, J.S. "Therapeutics applications: natural killer cells in the clinic", Hematology Am Soc Hematol Educ Program 2013; 1: 247-253.
Official Communication dated May 10, 2021 in European Application No. 18 710 125.8.
Notification of Reasons for Refusal dated Oct. 27, 2021 in Japanese Application No. 2019-547262 with English translation.

(Continued)

*Primary Examiner* — Daniel C Gamett
(74) *Attorney, Agent, or Firm* — Wenderoth, Lind & Ponack, L.L.P.

(57) ABSTRACT

This invention relates to Natural Killer (NK) cell populations, to methods of producing the same and therapeutic applications thereof. More specifically, the invention relates to the expansion of NK cells by increasing the expression of specific transcription factors associated with NK cell production.

10 Claims, 18 Drawing Sheets
Specification includes a Sequence Listing.

(56) References Cited

OTHER PUBLICATIONS

Noshiro, Mitsuhide et al., "Multiple Mechanisms Regulate Circadian Expression of the Gene for Cholesterol 7α-Hydroxylase (Cyp7a), a Key Enzyme in Hepatic Bile Acid Biosynthesis", Journal of Biological Rhythms, Aug. 2007, vol. 22, No. 4, pp. 299-311.
Gascoyne, Duncan M. et al., "The basic leucine zipper transcription factor E4BP4 is essential for natural killer cell development", Nature Immunology, Oct. 2009, vol. 10, No. 10, pp. 1118-1124.
Duez, Hélène et al., "Regulation of Bile Acid Synthesis by the Nuclear Receptor Rev-erbα", Gastroenterology, 2008, vol. 135, No. 2, pp. 689-698.
Ramakrishnan, Sadeesh K. et al., "Loss of von Hippel-Lindau Protein (VHL) Increases Systemic Cholesterol Levels through Targeting Hypoxia-Inducible Factor 2α and Regulation of Bile Acid Homeostasis", Molecular and Cellular Biology, Apr. 2014, vol. 34, No. 7, pp. 1208-1220.
English translation of Decision of Refusal dated Aug. 8, 2022 in Japanese Application No. 2019-547262.
Dahlberg, Carin I. M., "Natural Killer Cell-Based Therapies Targeting Cancer: Possible Strategies to Gain and Sustain Anti-Tumor Activity", Frontiers in Immunology, Nov. 2015, vol. 6, Article 605, pp. 1-19.

\* cited by examiner

D

A

NATURAL KILLER CELLS

FIELD OF THE INVENTION

This invention relates to expanded Natural Killer (NK) cell populations, to methods of producing the same and therapeutic applications thereof. More specifically, the invention relates to the expansion of NK cells by increasing the expression of specific transcription factors associated with NK cell production.

BACKGROUND OF THE INVENTION

There has been an increase in interest in Natural Killer (NK) cells as they are cytotoxic against cancerous, pathogen-infected and otherwise damaged cells. NK cells are innate lymphoid cells (ILCs), specifically large granular cytotoxic lymphocytes that bridge the innate and the adaptive arms of the immune response. They make up 10-15% of circulating lymphocytes in the peripheral blood. NK cells also exhibit the highest level of cytotoxic activity within the immune system. Therefore, altered NK cell functionality or numbers impact the functioning of the immune system against infection and cancer. For example, a large scale study in Japan has shown that reduced levels of NK cells in a cohort of people aged over 40 is associated with a significantly higher incidence of cancer.

Similarly to B cells and T cells, these NK cells are derived from Common Lymphoid Progenitor (CLP) cells that in turn come from Haematopoietic Stem Cells (HSCs). However, NK cells are different from B and T cells as they lack specific cell surface antigen receptors. Due to this, NK cells may kill cancerous and pathogen-infected cells without prior sensitisation, making them part of the innate immune response. They also have a critical role in tumour immunosurveillance by directly influencing the adaptive immune response.

Activation of NK cells triggers them to release perforin and cytoplasmic granules containing granzymes. Perforin polymerises to form pores on target cells in the presence of Ca2+. Granzymes may enter these pores into target cells, causing DNA fragmentation and apoptosis. NK cells may also secrete cytokines, which trigger the action of other immune cells in the adaptive arm of the immunity.

Due to the importance of NK cells in immune response against pathogen infection and cancer cells, multiple clinical trials have tested the efficacy of NK cells in adoptive transfer protocols. In adoptive transfer, NK cells isolated from the blood of donors are expanded ex vivo and matured into healthy and functional NK cells prior to transfusion into recipients. However, to be effective it is crucial that NK cell donors are be screened for their KIR genotype, where the donor must have the appropriate KIR allelic polymorphism to the recipient to allow recognition of target cells for destruction. In any event, studies have found that the expanded products have lower clinical success rate than expected, with less ability to kill cancerous or infected cells. Thus, there are significant barriers to the current adoptive transfer protocols.

An alternative therapeutic approach is to increase the number of endogenous NK cells. One method is the administration of cytokines that are essential for NK cell development. Administration of IL-2 and IL-15 was predicted to enhance NK cell development. IL-2 promotes the proliferation and cytotoxicity of NK cells, whereas IL-15 promotes the development and expansion of NK cells. However, in in vivo studies, the cytokines were found only stimulate a minimal expansion of NK cells with reduced half-life, even at a very high dose. Further, administered cytokines often leads to systemic toxicity due to inappropriate activation of immune responses and the induction of NK cell apoptosis.

Thus, using conventional methods and techniques, producing large numbers of NK cells is difficult, and producing fully functional NK cells with high cytotoxicity is even harder. There is currently no drug available that selectively increases NK cell numbers. Therefore, there is a need to develop new methods of NK cell production; both ex vivo to produce large numbers of functional NK cells for therapeutic and research use; and in vivo.

SUMMARY OF THE INVENTION

Natural Killer (NK) cells have a critical role in the immune system where they destroy cancerous, pathogen-infected or damaged cells. Boosting NK cell number or functionality is predicted to increase the killing of these cells. Existing therapies such as NK cell adoptive transfer and cytokine enhancement of endogenous NK cells are not very successful in terms of their efficacy.

NK cells are differentiated from the HSCs in the bone marrow and distributed throughout lymphoid and non-lymphoid tissues including lymph nodes, spleen, peripheral blood, lungs and liver. Specific cytokines and transcription factors are needed to encourage HSCs to develop into NK cells. Each cytokine and transcription factor must be present at a precise time and concentration in order to push differentiation from HSCs into NK cells. However, the precise hierarchy of cytokines and transcription factors governing NK cell maturation is still incompletely understood.

The present inventors have worked to identify drugs that can increase NK cell number. In particular, the present inventors have focussed on E4 binding protein 4 (E4bp4), which is also known as Nfil3. Upregulation of E4bp4 is a promising strategy to increase the production of NK cells as over expression of E4bp4 in HSCs greatly enhances in vitro NK cell production. However, transcription factors can be hard to drug because of their structure and function. For example, they usually lack enzymatic activity or cofactor binding sites. The present inventors have shown for the first time that inhibiting the action of REV-ERB increases NK cell production. In more details the inventors have found that inhibiting the action of REV-ERB increases E4bp4 expression, which in turn increases NK cell production. In particular, the present inventors have shown that an REV-ERB antagonist, SR8278, increases E4bp4 expression and hence NK cell production.

Accordingly, the present invention provides an ex vivo method for expanding an NK cell population, comprising the steps of: a) culturing an haematopoietic progenitor cell (HPC) comprising sample obtained from a patient; b) contacting said sample with a compound which inhibits the action of REV-ERB; and c) expanding said cells in vitro to produce an NK cell population.

Said compound may increase E4bp4 expression by decreasing REV-ERB activity. Typically said compound decreases the activity of REV-ERB-α and/or REV-ERB-β. Preferably said compound decreases the activity of REV-ERB-α and REV-ERB-β. In some embodiments, said compound is a REV-ERB antagonist, preferably an antagonist of REV-ERB-α and REV-ERB-β. Said compound may be selected from a small molecule, a PROTAC reagent, a double stranded RNA (dsRNA), a small interfering RNA (siRNA), a small hairpin RNA (shRNA), a micro RNA, an antisense RNA, an aptamer, an antibody, a ribozyme, a peptide or a peptidomimetic. In some preferred embodiments, said compound is a small molecule, for example SR8278, ARN5187, ethyl 2-(5-methylfuran-2-carbonyl)-1,2,3,4-tetrahydroisoquinoline-3-carboxylate, 4-((4-chlorobenzyl)((5-nitrothiophen-2-yl)methyl)amino)-N-phenylpiperidine-1-carboxamide, 4-(((1-(4-fluorophenyl)cyclopentyl)amino)methyl)-2-((4-methylpiperazin-1-yl)methyl)phenol, 1-(2-fluorophenyl)-N-(3-((1-methylpiperidin-4-yl)methyl)benzyl)cyclopentan-1-amine or 1-(4-fluorophenyl)-N-(3-((1-methylpiperidin-4-yl)methyl)benzyl)cyclopentan-1-amine, SR8278 is particularly preferred.

The sample of HPCs may be obtained from bone marrow, cord blood and/or peripheral blood. In some embodiments, the compound is added within 2 days of isolating the HPCs in the sample.

The invention further provides an expanded NK cell population obtained by the method of the invention, wherein at least 90% of the NK cells are $CD56^+$ and $CD45^+$.

The invention also provides a composition comprising an expanded NK cell population of the invention and a pharmaceutically acceptable carrier, diluent and/or excipient.

The invention further provides a compound which inhibits the action of REV-ERB for use in a method of therapy by increasing production of natural killer (NK) cells in a patient. Typically said compound is a compound of the invention as defined herein. The method of therapy may be a method of treating a disease or disorder selected from cancer, an infectious disease (acute or chronic), an autoimmune disease or a disease or disorder related to female infertility or pregnancy. The infection to be treated may be a viral infection, a bacterial infection, a protest infection, a fungal infection and/or a helminth infection. In some embodiments, the compound for use of the invention is used in combination with antibody-mediated immunotherapy. Said compound may be for administration before, simultaneously with, or after administration of the antibody-mediated immunotherapy. In some preferred embodiments, said compound is SR8278, ARN5187, ethyl 2-(5-methylfuran-2-carbonyl)-1,2,3,4-tetrahydroisoquinoline-3-carboxylate, 4-((4-chlorobenzyl)((5-nitrothiophen-2-yl)methyl)amino)-N-phenylpiperidine-1-carboxamide, 4-(((1-(4-fluorophenyl)cyclopentyl)amino)methyl)-2-((4-methylpiperazin-1-yl)methyl)phenol, 1-(2-fluorophenyl)-N-(3-((1-methylpiperidin-4-yl)methyl)benzyl)cyclopentan-1-amine or 1-(4-fluorophenyl)-N-(3-((1-methylpiperidin-4-yl)methyl)benzyl)cyclopentan-1-amine, with SR8278 being particularly preferred.

The invention further provides a method of treatment by increasing the number of NK cells in a patient in need thereof, comprising administering to said patient a therapeutically effective amount of a compound which inhibits the action of REV-ERB. Said compound may be used in combination with antibody-mediated immunotherapy.

DETAILED DESCRIPTION OF THE INVENTION

Natural Killer Cells

Natural Killer (NK) cells exhibit the highest level of cytotoxic activity within the immune system. NK cells are similar to B cells and T cells, but lack specific cell surface antigen receptors. Instead, NK cells have activatory and inhibitory receptors that recognise motifs.

NK cells circulate in the blood and the peripheral lymphoid organs such as lymph nodes and spleen. They can become activated by cytokines or upon encountering target cells. The recognition and elimination of target cells is based on balancing between inhibitory and activatory signals. Activatory signals are generated by activatory receptors (NKG$_2$D, NKp$_{46}$, NKp$_{30}$) binding to ligands, which can be present not only on cancerous, pathogen-infected and damaged cells, but also on healthy cells. On the other hand, inhibitory signals are generated when inhibitory receptors (KIR, CD$_{94}$/NKG$_2$A) on NK cells bind to Major Histocompatability Complex (MHC) Class I molecules that are normally present on all healthy cells. MHC Class I molecules on target cells are absent or greatly downregulated, making them ideal NK cell targets. This allowed NK cells to distinguish between target and healthy cells. In order for NK cells to recognise and kill target cells, overall activatory signals must be greater than inhibitory signals.

NK cells recognise and kill cancerous, pathogen-infected and damaged cells without prior sensitisation, making them part of the innate immune response. For example, NK cells provide an early response to virus infection, occurring prior to T cell killing of infected cells. NK cells can kill target cells within minutes. NK cells also secrete cytokines and "weaponise" other parts of the immune system. For example, NK cells promote T cell effector function and enhance antibody-directed cellular cytotoxicity (ADCC).

Figure 1:
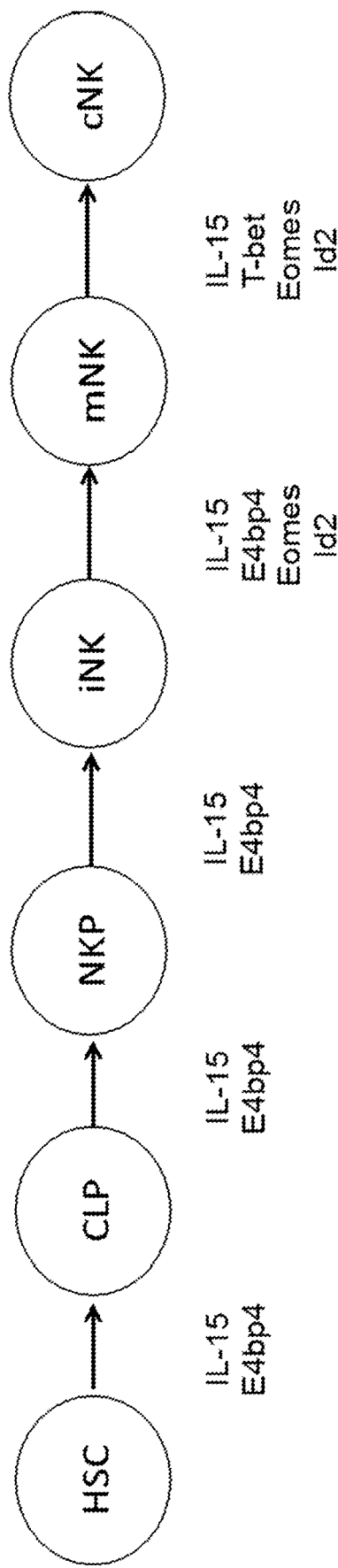
FIG. 1: NK cell developmental pathway. NK cells are differentiated from Hematopoietic Stem Cells (HSCs). NK cells develop from HSC into Common Lymphoid Progenitor (CLP) cells, NK progenitor (NKP) cells, immature NK (iNK) cells, mature NK (mNK) cells and finally into conventional NK (cNK) cells, which circulate in the bloodstream. Below the diagram of the pathway are the cytokines and transcription factors that are required for NK cell development. IL-15 is one of the main cytokine required for the development of NK cells. Others are transcription factors required for the transitions shown on the diagram.

NK cells are differentiated from haematopoietic stem cells (HSCs) via the pathway set out in FIG. 1. In more detail, NK cells develop from HSCs into Common Lymphoid Progenitor (CLP) cells, pre-NK progenitor (pre-NKP) cells, NK progenitor (NKP) cells, immature NK (iNK) cells, mature NK (mNK) cells and finally into conventional NK (cNK) cells, which circulate in the bloodstream. Although this terminology derives from NK cell development in mice, a corresponding pathway occurs in human NK cell development. For example, HSCs develop through multiple stages of precursors (stage 1, 2 and 3), before developing into mature NK cells (stages 4 and 5). For consistency, references HSCs, CLPs, pre-NKPs, NKPs, iNK, mNK, cNK and NK cells are used herein. However, in the context of the present invention, these terms are interchangeable with stages 1 to 5 of the human nomenclature. Below the diagram of the pathway in FIG. 1 are the cytokines and transcription factors that are essential for NK cell development. IL-15 is one of the main cytokine required for the development of NK cells. Other extrinsic factors, such as specific stromal cells, are also required for the development and maturation of NK cells. According to the present invention, Hematopoietic Progenitor Cells (HPCs) are a heterogeneous population containing multi-potential progenitors such as HSCs, CLPs and also NKPs. HPCs are referred to as lineage negative cells, as they have not yet committed to a developmental pathway. Accordingly, in the context of the present invention, HSCs, CLP cells and NKP cells are all HPCs and a reference to HPCs is a reference to any of HSCs, CLP cells and/or CLP cells, or any combination thereof, unless explicitly stated to the contrary.

Due to the importance of NK cells in immune response, multiple clinical trials have tested the efficacy of NK cells in adoptive transfer protocols. Typically this is allogenic transfer, with the NK cells being isolated from a healthy donor and expanded. However, the downregulation of MHC Class I molecules on target cells is partial and the KIR genotype from donors and recipients may be similar. Due to this, NK cells transfused into recipients, even from different individuals may not attach target cells if their KIRs recognise MHC Class I molecules. Therefore, it is crucial that NK cell donors must be screened for their KIR genotype, where the donor must have the appropriate KIR allelic polymorphism to the recipient to allow recognition of target cells for destruction. Moreover, the expanded products were found to have lower clinical success rate than expected, with less ability to kill cancerous or infected cells.

An NK cell may be defined in terms of its marker expression, its function/activity, or a combination thereof. Such definitions are standard in the art and methods are known by which marker expression and/or NK cell activity may be assessed. Thus, one of skill in the art would readily be able to categorise a cell as an NK cell using standard methodology and definitions.

For example, mNK and cNK cells may be recognised by their expression of the surface markers CD16 (FcγRIII) and/or CD56, typically both CD16 and CD56 in humans, and NK1.1 or NK1.2 in some mice strains. NKp46 is another marker for mNK and cNK cells, and is expressed in humans and several mice strains. Thus, NKp46 may be used as a marker for NK cells either with or without CD16 and/or CD56 (in humans) or with or without NK1.1 or NK1.2 (in mice). Other examples of makers which can be used to identify/define NK cells according to the present invention include Ly49, natural cytotoxicity receptors (NCRs), CD94, NKG2, killer-cell immunoglobulin-like receptors (KIRs), and/or leukocyte inhibitory receptors (ILT or LIR), or any combination thereof, including in combination with CD16 and or CD56 (in humans) or NK1.1/NK1.2 (in mice). In some preferred embodiments mature NK cells according to the invention (i.e. mNK and cNK cells) are $CD56^+$ and $CD45^+$, and may be also be $CD16^+$. As used herein, the term mature human NK cell encompasses NK cells that are $CD56^{bright}$ (stage 4) and $CD56^{dim}$ (stage 5), both of which are $CD56^+$. Mature NK cells may also be defined by the absence of markers, such as CD34, and lymphocyte markers CD3 and/or CD19. Thus, mature NK cells of the invention may be $CD56^+$, $CD45^+$, $CD16^+$, $CD3^-$ and/or $CD19^-$, or any combination thereof, such as $CD56^+$, $CD45^+$, $CD16^+$, $CD3^-$ and $CD19^-$.

In addition or alternatively, an NK may be identified by/defined in terms of its activity. For example, an NK cell may be identified/defined by the presence of cytolytic granules within its cytoplasm, by its ability to secrete antimicrobial molecules such as α-defensins, and/or its ability to secrete cytokines such as TNF-α, IL-10, IFN-γ and TFG-β.

Unless otherwise stated herein, a reference to NK cells includes a reference to iNK, mNK and cNK cells. HSCs, CLP cells and NKPs will typically be referred to as such.

Expanded NK Cell Populations

As disclosed herein, the invention provides methods for generating an expanded population of NK cells (referred to interchangeably herein as an expanded NK cell population or an NK cell population). Any of the disclosure herein in relation to NK cells of the present invention may also be applied to an expanded NK cell population of the invention.

Accordingly, the present invention provides an expanded NK cell population. Typically an expanded NK cell population of the invention comprises iNK cells, mNK cells and/or cNK cells, or a combination thereof. Said population may comprise HPCs, such as HSCs, CLP cells and/or NKPs, or a combination thereof, although the numbers of such cells is typically low relative to the number of NK cells, as the majority of these HPCs have differentiated into NK cells in the population. Said population may comprise other immune and/or non-immune cells. Again, the number of any such cells is typically low relative to the number of NK cells present in the population.

As a non-limiting example, at least 60%, at least 70%, at least 80%, at least 85%, at least 90%, at least 91%, at least 92%, at least 93%, at least 94%, at least 95%, at least 96%, at least 97%, at least 98%, at least 99% or more, up to 100% of the cells of an expanded NK cell population of the invention may be NK cells. Typically at least 80%, preferably at least 90%, more preferably at least 95% of the cells of an expanded NK cell population of the invention are NK cells.

In some embodiments, at least 60%, at least 70%, at least 80%, at least 85%, at least 90%, at least 91%, at least 92%, at least 93%, at least 94%, at least 95%, at least 96%, at least 97%, at least 98%, at least 99% or more, up to 100% of the cells of an expanded NK cell population of the invention are mature NK cells (i.e. mNK cells and/or cNK cells). Preferably at least 80%, more preferably at least 90%, and even more preferably at least 95%, even more preferably at least 98% or more of the cells of an expanded NK cell population of the invention are mature NK cells.

The number of HPCs (including HSCs, CLP cells and/or NKPs) may be less than 40%, less than 30%, less than 25%, less than 20%, less than 15%, less than 14%, less than 13%, less than 12%, less than 11%, less than 10%, less than 9%, less than 8%, less than 7%, less than 6%, less than 5%, less than 4%, less than 3%, less than 2%, less than 1% of the cells of the expanded NK cell population. Typically the number of HPCs (including HSCs, CLP cells and/or NKPs) is less than 20%, preferably less than 10%, more preferably less than 5%, even more preferably less than 2% or less of the cells of the expanded NK cell population.

The number of other immune and/or non-immune cells may be less than 40%, less than 30%, less than 25%, less than 20%, less than 15%, less than 14%, less than 13%, less than 12%, less than 11%, less than 10%, less than 9%, less than 8%, less than 7%, less than 6%, less than 5%, less than 4%, less than 3%, less than 2%, less than 1% of the cells of the expanded NK cell population. Typically the number of other immune and/or non-immune cells is less than 20%, preferably less than 10%, more preferably less than 5% of the cells, even more preferably less than 2%, or less of the expanded NK cell population.

As described herein, the expanded NK cell populations made by the methods of the present invention offer several advantages over NK cell populations made by conventional adoptive transfer methods. In particular, the methods of the present invention enable the production of expanded populations with greater number of NK cells compared with conventional methods. Further, a greater proportion of the NK cells in a population of the invention are functional, preferably fully functional, compared with populations obtained by conventional methods, in which a large number of the NK cells are "exhausted".

As used herein, the term "exhausted" in the context of NK cells means that an NK cell or expanded NK cell population has lost at least some of its effector functions, such as cytotoxic function, cytokine production and/or ADCC. Thus, an exhausted NK cell or expanded NK cell population may exhibit impaired survival, impaired cytotoxic function, altered or impaired cytokine production and/or impaired ADCC. For example, an exhausted NK cell or exhausted NK cell population may exhibit at least a 50% reduction in one of its effector functions. For example, at least a 50% reduction in cytokine secretion, at least a 50% reduction in ADCC and/or at least 50% reduction in cytotoxic activity. These values may be quantified relative to any appropriate control as defined herein. Any appropriate technique can be used to determine effector function, and hence to quantify and reduction therein. Suitable techniques are known in the art. Alternatively and/or in addition, exhausted NK cells may exhibit altered marker expression, such as an increase in the expression of one or more inhibitory receptor (as described herein) and/or a decrease in the expression of one or more activatory receptor (as described herein). In some embodiments, increased expression of NKG2A and/or Tim3 may be used as a marker for NK cell exhaustion. Again, the expression of these markers may be quantified relative to any appropriate control as defined herein.

In contrast, the terms "functional" and "fully functional" in the context of NK cells means that an NK cell or expanded NK cell population has all of the expected effector functions when responding to a given immune challenge. Thus, a (fully) functional NK cell or expanded NK cell population will typically exhibit cytotoxic function, cytokine production and/or ADCC as would be observed in vivo when NK cells are activated in response to an immune challenge, and will typically exhibit enhanced survival compared with NK cells produced using conventional methods. Alternatively and/or in addition, (fully) functional NK cells may exhibit altered marker expression, such as an increase in the expression of one or more activatory receptor (as described herein) and/or a decrease in the expression of one or more inhibitory receptor (as described herein). As a non-limiting example, a functional (mature) human NK cell may be $CD56^+$ and/or $CD45^+$, preferably both $CD56^+$ and $CD45^+$.

As a non-limiting example, the cytotoxicity of NK cells can be determined using a degranulation assay in NK cells co-incubated with 'target cells'. A degranulation assay involves analysing the expression of CD107a within the NK cell population. The amount of CD107a correlates with cytokine secretion and NK cell-mediated lysis of target cells. NK cells can also be analysed for the expression of Interferon-γ (IFN-γ), which is the main cytokine secreted when functional NK cells are activated. NK cells that are functional should express similar or higher CD107a as well as IFN-γ when compared to a control.

Any increase in NK cell number/functionality in an expanded NK cell population made by a method of the present invention may be compared with the NK cell number/function of an NK cell population obtained from a control method as described herein. A control method may be any standard method known in the art for producing NK cell populations. For example, a control method may use conventional adoptive transfer techniques, rather than a method using a REV-ERB inhibitor according to the present invention. NK cells and NK cell populations produced by such control/standard methods may be used as control cells and populations as described herein.

As an expanded NK cell population of the present invention comprises significantly fewer exhausted NK cells compared to conventionally prepared NK cell populations, but instead contains a higher proportion of fully functional NK cells, this advantageously allows the use of smaller numbers of cells to treat patients.

As described herein, the methods of the invention produce expanded NK cell populations with a higher proportion of (fully) functional NK cells compared with conventional methods, which produce populations with large numbers of "exhausted" NK cells. Typically, in an expanded NK cell population of the invention at least 50%, at least 60%, at least 70%, at least 80%, at least 85%, at least 90%, at least 91%, at least 92%, at least 93%, at least 94%, at least 95%, at least 96%, at least 97%, at least 98%, at least 99% or more, up to 100% of the NK cells of an expanded NK cell population of the invention are (fully) functional. Typically at least 80%, preferably at least 90%, more preferably at least 95%, even more preferably at least 98% or more of the NK cells of an expanded NK cell population of the invention are fully functional, according to any definition (e.g. marker and/or effector function definition) herein.

An expanded NK cell population of the invention may be produced by any of the methods disclosed herein. Typically an expanded NK cell population of the invention is produced by an ex vivo method as disclosed herein.

E4bp4

E4bp4 (also known as Nfil3) is a basic leucine zipper protein transcription factor which is involved in the regulation of IL-3 expression, and is involved in the coordinating the circadian clock. The genomic DNA sequence of the human E4bp4 gene is given in SEQ ID NO: 1 (Genbank Accession No. X64318, version X64318.1). As shown in FIG. 1, E4bp4 is expressed in CLPs and is critical in the production of NK cells from blood stem cell progenitors. Mice with the E4bp4 gene deleted do not have functional NK cells, but have normal numbers of T and B cells. In contrast, overexpression of E4bp4 in HSCs in vitro increases NK cell production. Thus, E4bp4 is a lineage commitment factor, controlling the development of NKPs from HSCs (FIG. 1). E4bp4's critical function in NK cells is specific to the early stages of the developmental pathway, as specific ablation of E4bp4 in peripheral mNK cells does not affect NK cell number or response to cytomegalovirus infection. In addition E4bp4 regulates other transcription factors that are essential in NK cell development, such as Id2 and Eomes.

Although IL-7 and IL-15 have been shown to regulate E4bp4 expression, generally very little is known about how either extrinsic or intrinsic stimuli influence E4bp4. Transcription factors such as E4bp4 can be hard to target because of their structure and function. For example, they usually lack enzymatic activity or cofactor binding sites. However, as demonstrated in the Examples herein, the present inventors have found that E4bp4 expression can be increased using a compound which inhibits the activity of REV-ERB. Further, the present inventors have demonstrated that the use of a REV-ERB inhibitor to increase E4bp4 expression results in an increase in NK cell number. Without wishing to be bound by theory, REV-ERB binds to porphyrin heme, and it is this characteristic that is believed to make REV-ERB a druggable target (see below). In sum, the inventors have shown that by targeting REV-ERB and inhibiting its activity, it is possible to increase E4bp4 expression and hence increase NK cell number. Accordingly, the present invention is concerned with compounds which inhibit the action of REV-ERB, and their use in increasing E4bp4 expression, and hence NK cell number.

Increase in E4bp4 Expression

Accordingly, the present invention provides ex vivo methods for producing expanded NK cell populations, and therapeutic methods and applications for increasing NK cell number in a patient in need thereof. As disclosed herein, said methods and applications involve the use of a compound which inhibits the action of REV-ERB. Typically said compounds act by increasing E4bp4 expression.

An increase in E4bp4 expression may be measured relative to a control. Thus, the expression of E4bp4 in a sample of HPCs, an expanded NK cell population or in a sample obtained from a patient to be treated according to the invention may be compared with the expression of E4bp4 in a control. Expression may be quantified in terms of gene and/or protein expression, and may be compared with expression of a control (e.g. housekeeping gene or protein). The actual amount of the E4bp4 gene, mRNA transcript and/or protein, such as the mass, molar amount, concentration or molarity of the E4bp4 gene, mRNA transcript and/or protein, or the number of mRNA molecules per cell in a sample of HPCs, an expanded NK cell population or in a sample obtained from a patient to be treated according to the invention and the control may be assessed and compared with the corresponding value from the control. Alternatively, the expression of the E4bp4 gene and/or protein in a sample of HPCs, an expanded NK cell population or in a sample obtained from a patient to be treated according to the invention may be compared with that of the control without quantifying the mass, molar amount, concentration or molarity of the one or more gene and/or protein.

Typically the control is an equivalent population or sample in which no increase in E4bp4 expression has been effected. As a non-limiting example, in the case where a patient is treated with a compound that inhibits REV-ERB activity in order to increase E4bp4 expression, a suitable control would be a different individual to which the compound has not been administered or the same individual prior to administration of the compound. Conventional methods for the ex vivo expansion of NK cells, including known methods may be considered control methods according to the present invention.

In the context of the present invention, a reference to increasing E4bp4 expression may be understood to mean that, the expression of E4bp4 is increased by at least 10%, at least 20%, at least 30%, at least 40%, at least 50%, at least 60, at least 70%, at least 80%, at least 85%, at least 90%, at least 95%, at least 100%, at least 150%, at least 200% compared with the control. Typically E4bp4 expression is increased by at least 50%, preferably at least 70%, more preferably at least 80%, even more preferably at least 90% or more compared with the control.

A reference to increasing E4bp4 expression may be understood to mean that, the expression of E4bp4 is increased by at least 1.5-fold, at least 2-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3-fold, at least 4-fold, at least 5-fold, at least 6-fold, at least 7-fold, at least 8-fold, at least 9-fold, at least 10-fold or more relative to a control. Typically E4bp4 gene expression is increased by at least 2-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3-fold, or more compared with the control. Typically E4bp4 protein expression is increased by at least 2-fold, at least 3-fold, preferably at least 5-fold, more preferably at least 6-fold or more compared with the control.

The expression of the E4bp4 gene and/or protein according to the invention may be determined by quantitative and/or qualitative analysis. Typically, gene expression may be expressed in terms of mRNA levels.

The expression level of the E4bp4 gene and/or protein according to the invention encompasses the mass of the E4bp4 mRNA transcript and/or protein, the molar amount of the E4bp4 gene, mRNA transcript and/or protein, the concentration of the E4bp4 gene and/or protein and the molarity of the E4bp4 gene and/or protein. This expression level may be given in any appropriate units. For example, the concentration of the E4bp4 gene and/or protein may be given in pg/ml, ng/ml or pg/ml.

The expression level of the E4bp4 gene and/or protein according to the invention may be measured directly or indirectly.

The relative expression of the E4bp4 gene and/or protein according to the invention relative to a control may be determined using any appropriate technique. Suitable standard techniques are known in the art, for example Western blotting, enzyme-linked immunosorbent assays (ELISAs) and RT-qPCR.

The expression level of the E4bp4 gene and/or protein may be increased compared with a control for at least 6 hours, at least 12 hours, at least 24 hours, at least 30 hours, at least 36 hours, at least 42 hours, at least 48 hours, at least 54 hours, at least 60 hours, at least 72 hours, at least 4 days, at least 5 days, at least 6 days, at least 1 week. Preferably, the expression level of the E4bp4 gene and/or protein is increased for at least 12 to 72 hours. Typically this is assessed relative to the last administration of the compound which inhibits REV-ERB activity.

The expression level of the E4bp4 gene and/or protein may be increased compared with a control for at least one, at least two, at least three, at least four, at least five, at least ten, at least 20, at least 30, at least 40 or more passages of the NK cell precursors in culture. The expression level of the E4bp4 gene and/or protein may be altered indefinitely.

REV-ERB

REV-ERB proteins are members of the nuclear receptor family of intracellular transcription factors. The mRNA sequence of the human REV-ERBα gene (Nr1d1) is given in SEQ ID NO: 3 (Genbank Accession No. NM_021724, version NM_021724.4). The mRNA sequence of the human REV-ERBβ gene (Nr1d2) is given in SEQ ID NO: 5 (Genbank Accession No. AB307693, version AB307693.1). REV-ERB regulates the circadian clock, and has also been implicated in the regulation of cartilage breakdown. It has previously been shown that REV-ERBα knock-out mice have decreased number of TH17 cells compared with the corresponding wild-type mouse strain. However, the role of REV-ERB in NK cell development has not previously been investigated.

Control of E4bp4 expression is a complex multi-component mechanism, involving many transcription factors that bind to E4bp4 regulatory regions, of which REV-ERB is just one. The present inventors have demonstrated for the first time that inhibition of REV-ERB activity is sufficient to elicit a significant increase in E4bp4 expression, and that this in turn brings about an expansion of NK cells, resulting in an increase in NK cell number. As demonstrated in the Examples herein, the present inventors have demonstrated for the first time that inhibition of REV-ERB activity can bring about an increase in NK cell number, and that typically the resulting NK cells are (fully) functional as defined herein. The inventors have further demonstrated that the effect of REV-ERB inhibition is mediated in an E4pb4-dependent manner. Without wishing to be bound by theory, it is believed that inhibition of REV-ERB activity results in an increase in E4bp4 expression (E4bp4 expression is normally repressed by REV-ERB), and that the E4bp4 acts to stimulate the production of NK cells (as shown in FIG. 1). In particular, the present inventors have demonstrated that the small molecule SR8278 is capable of binding to the porphyrin heme moiety of REV-ERB, resulting in inhibition of REV-ERB activity and an increase in NK cell number Accordingly, the present invention is concerned with compounds which inhibit the action of REV-ERB, and their use in increasing E4bp4 expression, and hence NK cell number.

Inhibition of REV-ERB Activity

The present invention relates to the use of compounds to inhibit the action of REV-ERB, i.e. compounds which inhibit REV-ERB activity. REV-REB activity may be inhibited by any appropriate means. Suitable standard techniques are known in the art. Inhibition may take place via any suitable mechanism, depending for example on the nature (see below) of the compound used, e.g. steric interference in any direct or indirect interaction or inhibition of REV-ERB. In the context of the present invention a REV-ERB inhibitor (interchangeably referred to herein as a REV-ERB antagonist) is any compound which inhibits, decreases, suppresses or ablates the action of REV-ERB, whether in part or completely.

A decrease in REV-ERB activity may be measured relative to a control. Thus, the activity of REV-ERB in a sample of NK precursor or progenitor cells, an expanded NK cell population or in a sample obtained from a patient to be treated according to the invention may be compared with the activity of REV-ERB in a control. Activity may be quantified in any appropriate terms, for example binding of REV-ERB to the E4bp4 gene, or in terms of E4bp4 expression as defined herein. Any appropriate technique or method may be used for quantifying REV-ERB activity. Suitable techniques are known in the art, for example luciferase assays for quantifying expression of a reporter gene.

Typically the control is an equivalent population or sample in which no REV-ERB inhibitory compound has been added, for example a sample obtained from a different individual to which the compound has not been administered, or the same individual the prior to administration of the compound. Conventional methods for the ex vivo expansion of NK cells, including known methods may be considered control methods according to the present invention.

In the context of the present invention, a reference to inhibiting REV-ERB activity may be understood to mean that, the activity of REV-ERB is decreased by at least 10%, at least 20%, at least 30%, at least 40%, at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, up to total (100%) inhibition of REV-ERB activity, as compared with the control. Typically REV-ERB activity is decreased by at least 50%, preferably at least 70%, more preferably at least 80%, more preferably at least 90%, even more preferably at least 95% or more compared with the control.

The activity of REV-ERB may be determined by quantitative and/or qualitative analysis, and may be measured directly or indirectly.

The activity of REV-ERB relative to a control may be determined using any appropriate technique. Suitable standard techniques are known in the art, such as by quantifying E4bp4 expression, and/or luciferase assays.

The activity of REV-ERB may be inhibited compared with a control for at least 6 hours, at least 12 hours, at least 24 hours, at least 30 hours, at least 36 hours, at least 42 hours, at least 48 hours, at least 54 hours, at least 60 hours, at least 72 hours, at least 4 days, at least 5 days, at least 6 days, at least 1 week. Preferably, the activity of REV-ERB is decreased for at least 12 to 72 hours. Typically this is assessed relative to the last administration of the compound which inhibits REV-ERB activity.

The activity of REV-ERB may be inhibited compared with a control for at least one, at least two, at least three, at least four, at least five, at least ten, at least 20, at least 30, at least 40 or more passages of the cells (either in vivo, or cultured ex vivo or in vitro). The activity of REV-ERB may be inhibited and/or the expression level of the E4bp4 gene and/or protein may be altered indefinitely.

In the context of the present invention any reference to inhibiting REV-ERB activity may be understood to mean inhibiting the activity of REV-ERBα and/or REV-ERBβ. In preferred embodiments, the activity of both REV-ERBα and REV-ERBβ is inhibited. Thus, the invention relates to compounds which inhibit REV-ERB activity, including compounds which inhibit REV-ERBα activity (i.e. REV-ERBα inhibitors, also referred to as REV-ERBα antagonists) and/or to compounds which inhibit REV-ERBβ activity (i.e. REV-ERBβ inhibitors, also referred to as REV-ERBβ antagonists). In preferred embodiments, the invention relates to compounds which inhibit the activity of both REV-ERBα and REV-ERBβ (i.e. REV-ERBα and REV-ERBβ inhibitors, also referred to as REV-ERBα and REV-ERBβ antagonists).

REB-ERB Antagonists/Inhibitors

Compounds of the invention may be specific for REV-ERB. By specific, it will be understood that the compound binds to REV-ERBα and/or REV-ERBβ, with no significant cross-reactivity to any other molecule, particularly any other protein. For example, modulator that is specific for REV-ERBα and/or REV-ERBβ will show no significant cross-reactivity with human neutrophil elastase. Cross-reactivity may be assessed by any suitable method. Cross-reactivity of REV-ERBα and/or REV-ERBβ inhibitor with a molecule other than REV-ERBα and/or REV-ERBβ may be considered significant if the inhibitor binds to the other molecule at least 5%, 10%, 15%, 20%, 25%, 30%, 35%, 40%, 45%, 50%, 55%, 60%, 65%, 70%, 75%, 80%, 85%, 90% or 100% as strongly as it binds to REV-ERBα and/or REV-ERBβ. An inhibitor that is specific for REV-ERBα and/or REV-ERBβ may bind to another molecule such as human neutrophil elastase at less than 90%, 85%, 80%, 75%, 70%, 65%, 60%, 55%, 50%, 45%, 40%, 35%, 30%, 25% or 20% the strength that it binds to REV-ERBα and/or REV-ERBβ. Preferably, the inhibitor binds to the other molecule at less than 20%, less than 15%, less than 10% or less than 5%, less than 2% or less than 1% the strength that it binds to REV-ERBα and/or REV-ERBP3.

Compounds of the invention may have off-target effects. An off-target effect is activity against a target other than REV-ERB. Typically compounds with off-target effects are encompassed by the present invention if the activity against the non-REV-ERB target is not significant compared with the activity against REV-ERB. Whether an off-target effect is significant may depend on the intended use of the compound. As a non-limiting example, a compound which may exert an off-target effect on the central nervous system would not be significant for a compound used in an ex vivo method as disclosed herein, but may be significant (depending on the magnitude of the off-target effect) for an in vivo therapeutic indication as disclosed herein. The presence and magnitude of any potential off target effects can be readily assessed using standard methods known in the art.

Any suitable inhibitor may be used according to the invention, for example small molecules, PROTAC reagents, double stranded RNA (dsRNA), small interfering RNA (siRNA), small hairpin RNA (shRNA), microRNA, antisense (single stranded) RNA, peptides and peptidomimetics, antibodies, aptamers and ribozymes. Preferred inhibitors include small molecules and PROTAC reagents.

Small Molecules

Small molecules may be used to inhibit REV-ERB activity as described herein. As defined herein, small molecules are low molecular weight compounds, typically organic compounds. Typically, a small molecule has a maximum molecule weight of 900 Da, allowing for rapid diffusion across cell membranes. In some embodiments, the maximum molecular weight of a small molecule is 500 Da. Typically a small molecule has a size in the order of 1 nm.

According to the present invention, small molecules may be able to exert an inhibitory effect on REV-ERB activity by binding to the porphyrin heme moiety of REV-ERB. Thus in some preferred embodiments, a compound that inhibits the action of REV-ERB according to the present invention is a compound which binds to the porphyrin heme moiety of REV-ERB, and hence inhibits the activity of REV-ERB. Alternatively, the small molecule may act via a different mechanism, for example, by binding to a non-heme portion of REV-ERB. Standard techniques are known in the art for the production of small molecules, which can then readily be tested for REV-ERB inhibitory activity as described herein.

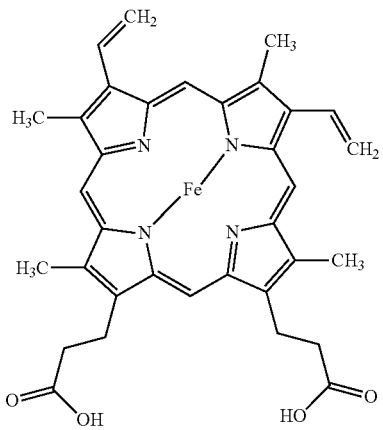

Structure of Porphyrin Heme

In a preferred embodiment, the invention relates to the small molecule 1,2,3,4-Tetrahydro-2-[[5-(methylthio)-2-thienyl]carbonyl]-3-isoquinolinecarboxylic acid ethyl ester, herein referred to as SR8278 as a REV-ERB inhibitor.

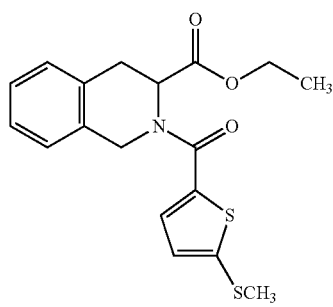 [SMILES: CCOC(=O)C1Cc2ccccc2CN1C(=O)c1ccc(SC)s1]

Structure of SR8278

The invention also encompasses the use of variants of SR8278 which retain the REV-ERB inhibitory function of SR8278.

Any small molecule which exerts an inhibitory effect on REV-ERB activity may be used as a REV-ERB inhibitor according to the present invention. Such small molecule inhibitors may also bind to REV-ERB. Examples of other small molecules which may be used as REV-ERB inhibitors according to the present invention include 4-[[[1-(2-fluorophenyl)cyclopentyl]amino]methyl]-2-[(4-methylpiperazin-1-yl)methyl]phenol (also referred to herein as ARN5187), ethyl 2-(5-methylfuran-2-carbonyl)-1,2,3,4-tetrahydroisoquinoline-3-carboxylate, 4-((4-chlorobenzyl)((5-nitrothiophen-2-yl)methyl)amino)-N-phenylpiperidine-1-carboxamide, 4-(((1-(4-fluorophenyl)cyclopentyl)amino)methyl)-2-((4-methylpiperazin-1-yl)methyl)phenol, 1-(2-fluorophenyl)-N-(3-((1-methylpiperidin-4-yl)methyl)benzyl)cyclopentan-1-amine and 1-(4-fluorophenyl)-N-(3-((1-methylpiperidin-4-yl)methyl)benzyl)cyclopentan-1-amine.

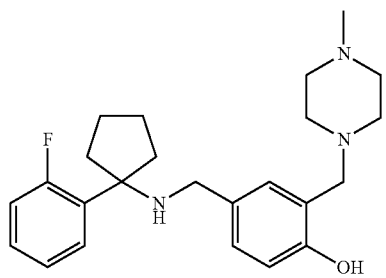 [SMILES: CN1CCN(Cc2cc(CNC3(c4ccccc4F)CCCC3)ccc2O)CC1]

Structure of ARN5187

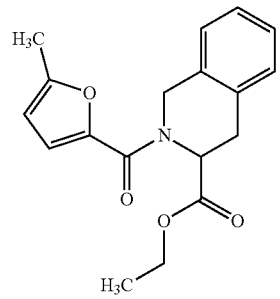 [SMILES: CCOC(=O)C1Cc2ccccc2CN1C(=O)c1ccc(C)o1]

Structure of ethyl 2-(5-methylfuran-2-carbonyl)-1,2,3,4-tetrahydroisoquinoline-3-carboxylate

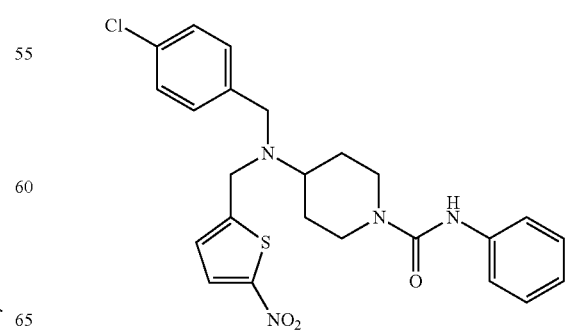

Structure of 4-((4-chlorobenzyl)((5-nitrothiophen-2-yl)methyl)amino)-N-phenylpiperidine-1-carboxamide

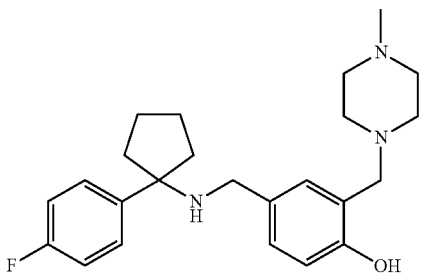 [SMILES: CN1CCN(Cc2cc(CNC3(c4ccc(F)cc4)CCCC3)ccc2O)CC1]

Structure of 4-(((1-(4-fluorophenyl)cyclopentyl)amino)methyl)-2-((4-methylpiperazin-1-yl)methyl)phenol

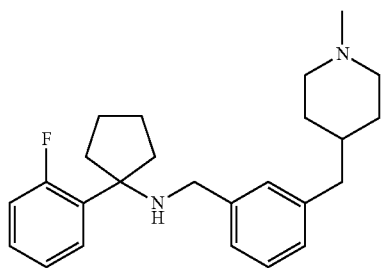 [SMILES: CN1CCC(Cc2cccc(CNC3(c4ccccc4F)CCCC3)c2)CC1]

Structure of 1-(2-fluorophenyl)-N-(3-((1-methylpiperidin-4-yl)methyl)benzyl)cyclopentan-1-amine

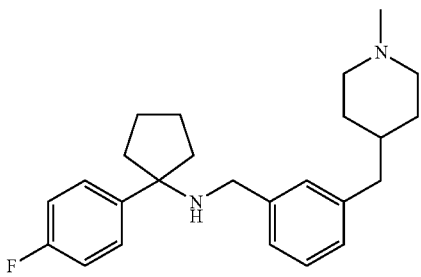 [SMILES: CN1CCC(Cc2cccc(CNC3(c4ccc(F)cc4)CCCC3)c2)CC1]

Structure of 1-(4-fluorophenyl)-N-(3-((1-methylpiperidin-4-yl)methyl)benzyl)cyclopentan-1-amine The invention also encompasses the use of variants of ARN5187, , ethyl 2-(5-methylfuran-2-carbonyl)-1,2,3,4-tetrahydroisoquinoline-3-carboxylate, 4-((4-chlorobenzyl)((5-nitrothiophen-2-yl)methyl)amino)-N-phenylpiperidine-1-carboxamide, 4-(((1-(4-fluorophenyl)cyclopentyl)amino)methyl)-2-((4-methylpiperazin-1-yl)methyl)phennol 1-(2-fluorophenyl)-N-(3-((1-methylpiperidin-4-yl)methyl)benzyl)cyclopentan-1-amine or 1-(4-fluorophenyl)-N-(3-((1-methylpiperidin-4-yl)methyl)benzyl)cyclopentan-1-amine which retain the REV-ERB inhibitory function of ARN5187, , ethyl 2-(5-methylfuran-2-carbonyl)-1,2,3,4-tetrahydroisoquinoline-3-carboxylate, 4-((4-chlorobenzyl)((5-nitrothiophen-2-yl)methyl)amino)-N-phenylpiperidine-1-carboxamide, 4-(((1-(4-fluorophenyl)cyclopentyl)amino)methyl)-2-((4-methylpiperazin-1-yl)methyl)phenol, 1-(2-fluorophenyl)-N-(3-((1-methylpiperidin-4-yl)methyl)benzyl)cyclopentan-1-amine or 1-(4-fluorophenyl)-N-(3-((1-methylpiperidin-4-yl)methyl)benzyl)cyclopentan-1-amine respectively.

PROTAC Reagents

Proteolysis targeting chimeras (also referred to as PROTACs or PROTAC reagents) may be used to inhibit REV-ERB activity as described herein. PROTACs are heterobifunctional small molecules that simultaneously bind a target protein and ubiquitin ligase, enabling ubiquitination and degradation of the target. In more detail, a PROTAC reagent typically comprises a ligand for the target protein (in the case of the present invention, REV-ERB) and a ligand for an E3 ligase recognition domain. Through the use of such a PROTAC, an E3 ligase is recruited to the PROTAC-bound REV-ERB, inducing ubiquitin transfer from the E3 ligase complex to the target protein (in the case of the present invention, REV-ERB). Once the PROTAC has induced a sufficient degree of ubiquitination of the target, it is then recognised and degraded by the proteasome.

As a non-limiting example, a PROTAC reagent may be produced by conjugating a ligand for an E3-ligase to a small molecule inhibitor as described herein (preferably SR8278) via a linker. In a preferred embodiment, a PROTAC reagent comprises a ligand for the E3 RING Cullin ligase von-Hippel Lindau protein (VHL) or cereblon—a part of a CRL4 E3 RING Cullin ligase complex, connected to a small molecule inhibitor of the invention via a linker. In some particularly preferred embodiments, the PROTAC reagent comprises a ligand for the E3 RING Cullin ligase von-Hippel Lindau protein (VHL) connected to SR8278, connected via a linker. In other particularly preferred embodiments, the PROTAC reagent comprises cereblon (a part of a CRL4 E3 RING Cullin ligase complex) and SR8278, connected via a linker.

Because of their mechanism of action, PROTAC reagents simply need any ligand for the target protein. The functional pharmacology of the ligand, in the absence of the linker and E3 ligase ligand, is unimportant. Therefore in some embodiments a REV-ERB inhibitory PROTAC reagent of the present invention may comprises a small molecule REV-ERB agonist as the ligand, such as GSK4112 (1,1-Dimethylethyl N-[(4-chlorophenyl)methyl]-N-[(5-nitro-2-thienyl)methyl])glycinate, SR6452).

Double-Stranded RNA

Double-stranded RNA (dsRNA) molecules may be used to inhibit REV-ERB activity as described herein. dsRNA molecules may be used in RNAi to inhibit REV-ERB activity.

Using known techniques and based on a knowledge of the sequence of REV-ERB, dsRNA molecules can be designed to antagonise REV-ERB by sequence homology-based targeting of the corresponding RNA sequence. Such dsRNAs will typically be small interfering RNAs (siRNAs), small hairpin RNAs (shRNAs), or micro-RNAs (miRNAs). The sequence of such dsRNAs will comprise a portion that corresponds with that of a portion of the mRNA encoding REV-ERB. This portion will usually be 100% complementary to the target portion within the mRNA transcribed from the REV-ERB gene, but lower levels of complementarity (e.g. 90% or more or 95% or more) may also be used. Typically the % complementarity is determined over a length of contiguous nucleic acid residues. A dsRNA molecule of the invention may, for example, have at least 80% complementarity to the target portion within the mRNA transcribed from the REV-ERB gene measured over at least 10, at least 20, at least 30, at least 40, at least 50, at least 60, at least 70, at least 80, at least 90, or more nucleic acid residues, up to the dsRNA molecule having at least 80% complementarity the mRNA transcribed from the REV-ERB gene of the invention over the entire length of the dsRNA molecule.

In a preferred embodiment, the dsRNA is a shRNA. ShRNA can be delivered to NK cell precursors by any appropriate means. Suitable techniques are known in the art and include the use of plasmid, viral and bacterial vectors to deliver the shRNA. Typically, the shRNA is delivered using a viral vector delivery system. In a preferred embodiment, the viral vector is a lentiviral vector.

Generally, once the shRNA has been delivered to an NK precursor cell, it is then transcribed in the nucleus and processed. The resulting pre-shRNA is exported from the nucleus and then processed by dicer and loaded into the RNA-induced silencing complex (RISC). The sense (passenger) strand is degraded. The antisense (guide) strand directs RISC to mRNA that has a complementary sequence. In the case of perfect complementarity, RISC cleaves the mRNA. In the case of imperfect complementarity, RISC represses translation of the mRNA. In both of these cases, the shRNA leads to target gene silencing.

A variant sequence may have at least 80% sequence identity to an shRNA sequence of the invention, measured over any appropriate length of sequence. Typically the % sequence identity is determined over a length of contiguous nucleic acid or amino acid residues. A variant sequence of the invention may, for example, have at least 80% sequence identity to a sequence of the invention measured over at least 10, at least 20, at least 30, at least 40, at least 50, at least 60, at least 70, at least 80, at least 90, or more nucleic acid or amino acid residues.

For example, a variant shRNA molecule of the invention may have at least 80% sequence identity with an shRNA molecule of the invention measured over at least 10, at least 20, at least 30, at least 40, at least 50, at least 60 or more nucleic acid residues, up to the variant shRNA molecule having at least 80% sequence identity with the shRNA molecule of the invention over the entire length of the variant shRNA molecule.

Antisense RNA

Single-stranded DNA (ssDNA) molecules, also known as antisense RNA, may be used to inhibit REV-ERB activity as described herein.

Using known techniques and based on a knowledge of the sequence of the REV-ERB gene, antisense RNA molecules can be designed to antagonise the REV-ERB gene by sequence homology-based targeting of the corresponding RNA. The sequence of such antisense will comprise a portion that corresponds with that of a portion of the mRNA transcribed from the REV-ERB gene. This portion will usually be 100% complementary to the target portion within the transcribed mRNA but lower levels of complementarity (e.g. 90% or more or 95% or more) may also be used.

Aptamers

Aptamers are generally nucleic acid molecules that bind a specific target molecule. Aptamers can be engineered completely in vitro, are readily produced by chemical synthesis, possess desirable storage properties, and elicit little or no immunogenicity in therapeutic applications. These characteristics make them particularly useful in pharmaceutical and therapeutic utilities.

As used herein, "aptamer" refers in general to a single or double stranded oligonucleotide or a mixture of such oligonucleotides, wherein the oligonucleotide or mixture is capable of binding specifically to a target. Oligonucleotide aptamers will be discussed here, but the skilled reader will appreciate that other aptamers having equivalent binding characteristics can also be used, such as peptide aptamers.

In general, aptamers may comprise oligonucleotides that are at least 5, at least 10 or at least 15 nucleotides in length. Aptamers may comprise sequences that are up to 40, up to 60 or up to 100 or more nucleotides in length. For example, aptamers may be from 5 to 100 nucleotides, from 10 to 40 nucleotides, or from 15 to 40 nucleotides in length. Where possible, aptamers of shorter length are preferred as these will often lead to less interference by other molecules or materials.

Aptamers may be generated using routine methods such as the Systematic Evolution of Ligands by Exponential enrichment (SELEX) procedure. SELEX is a method for the in vitro evolution of nucleic acid molecules with highly specific binding to target molecules. It is described in, for example, U.S. Pat. Nos. 5,654,151, 5,503,978, 5,567,588 and WO 96/38579.

The SELEX method involves the selection of nucleic acid aptamers and in particular single stranded nucleic acids capable of binding to a desired target, from a collection of oligonucleotides. A collection of single-stranded nucleic acids (e.g., DNA, RNA, or variants thereof) is contacted with a target, under conditions favourable for binding, those nucleic acids which are bound to targets in the mixture are separated from those which do not bind, the nucleic acid-target complexes are dissociated, those nucleic acids which had bound to the target are amplified to yield a collection or library which is enriched in nucleic acids having the desired binding activity, and then this series of steps is repeated as necessary to produce a library of nucleic acids (aptamers) having specific binding affinity for the relevant target.

Peptidomimetics

Peptidomimetics are compounds which mimic a natural peptide or protein with the ability to interact with the biological target and produce the same biological effect. Peptidomimetics may have advantages over peptides in terms of stability and bioavailability associated with a natural peptide. Peptidomimetics can have main- or side-chain modifications of the parent peptide designed for biological function. Examples of classes of peptidomimetics include, but are not limited to, peptoids and β-peptides, as well as peptides incorporating D-amino acids.

Antibodies

Antibodies may be used to inhibit REV-ERB activity as described herein.

As used herein, the term antibody encompasses the use of a monoclonal antibody or polyclonal antibody, as well as the antigen-binding fragments of a monoclonal or polyclonal antibody, or a peptide which binds to REV-ERB with specificity. The antibody may be a Fab, F(ab')2, Fv, scFv, Fd or dAb.

Variant Sequences

A sequence identity of at least 80% includes at least 82%, at least 84%, at least 86%, at least 88%, at least 90%, at least 91%, at least 92%, at least 93%, at least 94%, at least 95%, at least 96%, at least 97%, at least 98%, at least 99%, and 100% sequence identity (to each and every sequence presented herein and/or to each and every SEQ ID NO presented herein).

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the. Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position-Specific Gap Penalties and Weight Matrix Choice, 22 (22) Nucleic Acids Research 4673-4680 (1994); and iterative refinement, see, e.g., Osamu Gotoh, Significant Improvement in Accuracy of Multiple Protein. Sequence Alignments by Iterative Refinement as Assessed by Reference to Structural Alignments, 264(4) J. Mol. Biol. 823-838 (1996). Local methods align sequences by identifying one or more conserved motifs shared by all of the input sequences. Non-limiting methods include, e.g., Match-box, see, e.g., Eric Depiereux and Ernest Feytmans, Match-Box: A Fundamentally New Algorithm for the Simultaneous Alignment of Several Protein Sequences, 8(5) CABIOS 501-509 (1992); Gibbs sampling, see, e.g., C. E. Lawrence et al., Detecting Subtle Sequence Signals: A Gibbs Sampling Strategy for Multiple Alignment, 262 (5131) Science 208-214 (1993); Align-M, see, e.g., Ivo Van Walle et al., Align-M—A New Algorithm for Multiple Alignment of Highly Divergent Sequences, 20 (9) Bioinformatics: 1428-1435 (2004). Thus, percent sequence identity is determined by conventional methods. See, for example, Altschul et al., Bull. Math. Bio. 48: 603-16, 1986 and Henikoff and Henikoff, Proc. Natl. Acad. Sci. USA 89:10915-19, 1992.

Variants of the specific sequences provided above may alternatively be defined by reciting the number of nucleotides or amino acids that differ between the variant sequences and the specific reference sequences provided above. Thus, in one embodiment, the sequence may comprise (or consist of) a nucleotide sequence that differs from the specific sequences provided above at no more than 5, no more than 4, no more than 3, no more than 2 nucleotide positions, for example at no more than 1 nucleotide position. Conservative substitutions are preferred.

The variant nucleic acid molecules and peptides of the invention typically still retain the activity of the corresponding molecules of the invention. Thus, for example, the variant shRNA molecules of the invention retain the ability of the corresponding shRNA molecules to inhibit the expression of REV-ERB. The variant shRNA molecules may retain at least 50%, at least 60%, at least 70%, at least 80%, at least 90%, up to and including 100% of the modulatory activity of the shRNA molecules of the invention. This applies equally to any other variants of the inhibitors of the invention.

The compounds of the invention may be labelled (or tagged). Any appropriate label may be used. Suitable labels are known in the art.

Methods of Expanding NK Cells

The present invention relates to a method for expanding an NK cell population. Said method may be in vitro, in vivo or ex vivo. Said method comprises containing HPCs with a compound that inhibits the action of REV-ERB (as described herein) and expanding said cells to produce an NK cell population. The methods of the invention allow for the rapid expansion of NK cells, reducing the time needed for their culture, and hence the risk of exhaustion, enhancing the cytotoxicity of the NK cells when transfused into a patient.

When said method is carried out in vivo, said method is a therapeutic method as described herein. In such embodiments, all the disclosure herein in relation to therapeutic indications and applications of the invention is applicable to said methods.

Typically the method of the invention is ex vivo. Accordingly, the invention provides an ex vivo method for expanding an NK cell population comprising the steps of: (a) culturing an NK precursor cell comprising sample obtained from a patient; (b) contacting said sample with a compound that inhibits the action of REV-ERB; and (c) expanding said cells in vitro to produce an NK cell population. The compound may be any REV-ERB inhibitory compound of the invention as described herein. Typically said compound increases E4bp4 expression by decreasing REV-ERB activity as described herein.

The sample comprising HPCs obtained from a patient may be a sample obtained from bone marrow, cord blood and/or peripheral blood. Thus, the sample may be a cord or peripheral blood sample, or a bone marrow sample or biopsy.

According to the present invention, a sample comprising HPCs is any sample from a patient which comprises a sufficient number of HPCs (as described herein), such that an expanded NK cell population can be obtained by contacting said sample with a compound according to the present invention. Typically the sample comprises HSCs. Preferably said sample is enriched for HSCs, such as a cord or peripheral blood sample or a bone marrow sample or biopsy as described herein.

The HPCs may be cultured on or with suitable support/stromal cells or cell layer. Any appropriate stromal cell may be used, including, but not limited to OP9 stromal cells and/or EL08-1D2 stromal cells. Alternatively and/or in addition, the HPCs may be cultured in the presence of cytokines and growth factors associated with the development of cells in the NK cell differentiation pathway, including factors required for HPCs growth and/or factors required for NK cell growth and/or differentiation. Non-limiting examples of such factors include IL-3, IL-7, FIt3L, stem cell factor (SCF) and/or IL-15, or any combination thereof.

In some embodiments, the ex vivo method comprises a single stage in which the HPCs in a sample obtained from a patient are cultured, contacted with a compound of the invention and expanded to form an NK cell population, typically under substantially constant culture conditions. Typically this involves incubating the HPCs with factors such as IL-3, IL-7, SCF, FIt3L and/or IL-15, preferably all of these factors. The HPCs are preferably also cultured on or with stromal cells/cell layer, such as EL08-1D2 stromal cells.

In some embodiments, the ex vivo method comprises two stages. The first is a lymphoid production stage, in which the HPCs in a sample obtained from a patient are cultured. Typically this involves incubating the HPCs with cytokines and growth factors associated with lymphoid production, such as FIt3L, IL-7 and/or SCF. This stage may last for at least one, at least two, at least three, at least four, or more days. In some preferred embodiments, this stage lasts for two days.

The second stage of the ex vivo method is a stage of NK cell expansion. Typically this involves transferring the cultured HSCs to a suitable stromal (support) cell layer, such as OP9 stromal cells and culturing in cytokines and growth factors associated with NK cell development, such as IL-15. A compound of the invention is typically added during this second stage, and preferably at the start of this second stage. The second stage lasts for the remainder of the ex vivo culture period (as defined above). The culture medium may be changed as often as required during this second stage in order to facilitate NK cell expansion.

The HPC comprising sample may be cultured ex vivo for at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days or more. Typically said sample is cultured for at least 9 days in order to produce an expanded NK cell population. These culture periods are for the total culture period of the ex vivo method, i.e. if there are two stages, these periods are for the total (stage 1 plus stage 2).

The compound of the invention may be added to the sample comprising HPCs within one week, within six days, within five days, within four days, within three days, within two days, within one day of isolating the HPCs in the sample, or on the same day as isolating the NK cell precursors. Typically this is the same day that the sample is obtained from the patient. Preferably the compound of the invention is added to the sample within two days of isolating the HPCs in the sample, even more preferably on day two following isolation of the HPCs.

The method of the invention may further comprise modulating (increasing or decreasing the expression and/or activity of one or more additional gene and/or protein in the HPCs in order to enhance NK cell expansion. This modulation may be elicited by a compound of the invention, including the same compound of the invention as used to inhibit the activity of REV-ERB. Alternatively, one or more additional compounds may be used to modulate the expression and/or activity of the one or more additional gene and/or protein. Said modulation may occur directly or indirectly. Indirect modulation encompasses downstream effects caused by a compound of the invention inhibiting the activity of REV-ERB.

A method of the invention may result in an increase in, the number of NK cells of at least 1.5-fold, at least 2-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3-fold, at least 4-fold, at least 5-fold, at least 6-fold, at least 7-fold, at least 8-fold, at least 9-fold, at least 10-fold or more relative to a control. Typically the number of NK cells is increased by at least 2-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3-fold, or more compared with the control.

Typically an ex vivo method of the present invention involves a final step to purify the expanded NK cell population. This ensures a pure population for therapeutic administration as described herein. Purification of the expanded NK cell population may be by any appropriate means. Standard cell purification methods are known in the art, such as cell sorting, including fluorescence-activated cell sorting (FACS) and magnetic-activated cell sorting (MACS).

Therapeutic Indications

The invention provides a REV-ERB antagonist for use in a method of therapy by increasing the production of NK cells in a patient.

The REV-ERB antagonist for use in said method of therapy may be any REV-ERB antagonist as described herein. Typically the REV-ERB antagonist for use in said method increases E4bp4 expression by decreasing REV-ERB activity.

Typically the method of therapy comprises administering a compound which inhibits the action of REV-ERB (as described herein) to a patient or subject.

As used herein, the term "increasing the number of NK cells" and "increasing production of NK cells" can be understood to mean that the compound of the invention elicits a significant increase in the number of NK cells in a patient. This increase in NK cell number may be measured relative to a control (as described herein in the context of increasing E4bp4 expression and inhibiting REV-ERB activity).

A reference to an increase in the number of NK cells and/or increasing NK cell production may be quantified in terms of a fold increase relative to a control. Typically a compound of the invention can increase the number of NK cells, or give rise to an increase in NK cell production, of at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 3 fold or more relative to a control.

Alternatively, a reference to increasing the number of NK cells and/or increasing NK cell production may be understood to mean that, the number of NK cells is increased by at least 10%, at least 20%, at least 30%, at least 40%, at least 50%, at least 60, at least 70%, at least 80%, at least 85%, at least 90%, at least 95%, at least 100%, at least 150%, at least 200%, at least 300% or more compared with the control. Typically the number of NK cells is increased by at least 50%, preferably at least 70%, more preferably at least 80%, even more preferably at least 90% or more compared with a control.

In some embodiments, an increase in the number of NK cells and/or increase in NK cell production may be defined in terms of the absolute number of NK cells in a sample or patient, such as the percentage of NK cells, for example the percentage of NK cells in the circulating lymphocyte population. For example, a compound of the invention may cause an increase in NK number, resulting in a percentage of NK cells of at least 10%, at least 15%, at least 20%, at least 25%, at least 30%, at least 35%, at least 40%, at least 45%, at least 50%, at least 55%, at least 60%, at least 65%, at least 70%, at least 75%, at least 80% or more.

The number of NK cells may be determined by quantitative and/or qualitative analysis, and may be measured directly or indirectly. The number of NK cells relative to a control may be determined using any appropriate technique. Suitable standard techniques, such as flow cytometry, FACS and MACS, are known in the art.

The number of NK cells may be increased compared with a control for at least 6 hours, at least 12 hours, at least 24 hours, at least 30 hours, at least 36 hours, at least 42 hours, at least 48 hours, at least 54 hours, at least 60 hours, at least 72 hours, at least 4 days, at least 5 days, at least 6 days, at least 1 week, at least 2 weeks, at least 3 weeks, at least 1 month or more. Typically this is assessed relative to the last administration of the compound which inhibits REV-ERB activity.

The number of NK cells may be quantified in terms of the total number of NK cells in a sample from a patient or culture sample (from an ex vivo method of the invention).

In the context of the therapeutic uses and methods of the invention, a "subject" or "patient" (these terms are used interchangeably herein) is any animal patient that would benefit from an increase in the number of NK cells. Typical animal patients are mammals, such as primates. Preferably the patient is a human.

Thus, the present invention provides a method of treatment by increasing the number of NK cells in a patient in need thereof, comprising administering to said patient a therapeutically effective amount of a compound which inhibits the action of REV-ERB (as described herein).

Additionally, the present invention provides the use of a compound which inhibits the action of REV-ERB in the manufacture of a medicament. Said medicament increases the number of NK cells in a patient.

The therapeutic use or method of the invention may comprise administering a therapeutically effective amount of a compound of the invention, either alone or in combination with other therapeutic agents, to a subject.

As used herein, the term "treatment" or "treating" embraces therapeutic or preventative/prophylactic measures.

The compounds of the invention may also be used as a preventative therapy. As used herein, the term "preventing" includes preventing the onset of symptoms associated with a disease or disorder that may be treated by increasing NK cell number and/or reducing the severity or intensity of said symptoms. The term "preventing" includes inducing or providing protective immunity against such diseases or disorders, particularly infectious diseases as described herein. Immunity may be quantified using any appropriate technique, examples of which are known in the art.

A compound of the invention may be administered to a patient already having a disease or disorder which may be treated by increasing NK cell number. For example, the patient may be suspected of having an infectious disease or cancer as described herein, and may or may not be showing symptoms of said disease or disorder. When administered to such a patient, a compound of the invention can cure, delay, reduce the severity of, or ameliorate one or more symptoms, and/or prolong the survival of a subject beyond that expected in the absence of such treatment.

Alternatively, a compound of the invention may be administered to a patient who may ultimately be infected with a particular infectious disease, or develop a disease or disorder as described herein, in order to cure, delay, reduce the severity of, or ameliorate one or more symptoms, and/or prolong the survival of a subject beyond that expected in the absence of such treatment, or, in the case of infectious diseases help prevent that patient from transmitting said disease.

The treatments and preventative therapies of the present invention are applicable to a variety of different subjects of different ages. In the context of humans, the therapies are applicable to children (e.g. infants, children under 5 years old, older children or teenagers) and adults. In the context of other animal subjects (e.g. mammals such as primates), the therapies are applicable to immature subjects and mature/adult subjects.

The invention relates to the treatment of any disease or disorder which may be beneficially treated with by increasing the number of NK cells in a patient. Such diseases and disorders include cancer, infectious diseases (acute and chronic), autoimmune diseases and diseases or disorders related to female infertility or pregnancy. Infectious diseases that may be treated according to the present invention include viral infection, and infection by other pathogens, including bacteria, protists, fugal, or helminth pathogens. Typically said pathogens are intracellular pathogens which have at least one intracellular phase in their life cycle.

Infections of particular interest include viral infections, and zoonotic infections that are of particular importance from a public health perspective. Cancers that may be treated according to the present invention include bladder cancer, blood cancers, leukaemia, bone cancers, bowel cancer, brain tumours, breast cancer, kidney cancer, liver cancer, lung cancer, melanoma, ovarian cancer, pancreatic cancer, prostate cancer, skin cancer, stomach cancer, testicular cancer and uterine cancer. Autoimmune diseases that may be treated according to the present invention include systemic lupus erythematosus, rheumatoid arthritis, multiple sclerosis and obesity-induced insulin resistance. As used herein, the term diseases or disorders related to female infertility or pregnancy includes, but is not limited to, fetal growth restriction, preterm labour, defects in uterine vascular remodelling and preeclampsia.

The compounds of the invention may be used in combination with one or more additional therapeutic agents or treatments, which typically may be selected from a conventional treatment for the disease or disorder to be treated. As a non-limiting example, if a compound of the invention is for use in the treatment of a cancer, such as lung cancer, then said compound may be used in combination with conventional treatments for lung cancer, such as radiotherapy, chemotherapy or surgery. When used in combination with one or more additional therapeutic agent or treatment, a compound of the invention may be administered before, simultaneously with, or after the administration of the one or more additional therapeutic agent or treatment.

In some preferred embodiments, a compound of the invention is for use in combination with antibody-mediated immunotherapy. Antibody-mediated immunotherapy involves the administration of antibodies to a patient to target disease-specific antigens. Such antibodies could be used to increase the specificity and killing activity of NK cells, which express receptors for the Fc regions of IgG antibodies. Activation of these Fc receptors, leads to NK cell activation, resulting in cytokine secretion and release of cytotoxic granules by the activated NK cell, causing lysis of the cell expressing the disease antigen. Such combination therapy is particularly preferred for the treatment of cancer (using antibodies to tumour-specific antigens). Any antibody used in immunotherapy may be used in combination with a compound of the invention. Non-limiting examples of such antibodies include anti-CD20 mAbs (non-Hodgkin's lymphoma, chronic lymphocytic lymphoma), anti-ganglioside D2 (anti-GD2) mAbs (neuroblastoma, melanoma), anti-human epidermal growth factor (anti-HER2) mAbs (breast and gastric cancers), anti-epidermal growth factor receptor (anti-EGFR) mAbs (colorectal and head and neck cancer).

In other aspects, the invention provides the use of an expanded NK cell population (as described herein) in a therapeutic use or method as described herein. Any and all of the disclosure herein in relation to therapeutic indications of a compound of the invention may apply equally and independently to therapeutic applications of the expanded NK cell populations of the invention. As a non-limiting example, the present invention provides an expanded NK cell population (as described herein) for use in a method of therapy, for example in the treatment of cancer, an infectious diseases, an autoimmune disease or a disease or disorder related to female infertility or pregnancy. As another non-limiting example, the invention provides a method of treatment by increasing the number of NK cells in a patient in need thereof, comprising administering to said patient a therapeutically effective amount of an expanded NK cell population.

Pharmaceutical Compositions and Formulations

The term "compound" is herein used interchangeably with the terms "therapeutic/prophylactic composition", "formulation" or "medicament".

The compound or expanded NK cell population of the invention (as defined above) can be combined or administered in addition to a pharmaceutically acceptable carrier, diluent and/or excipient. Alternatively or in addition the compound or expanded NK cell population of the invention can further be combined with one or more of a salt, excipient, diluent, adjuvant, immunoregulatory agent and/or antimicrobial compound.

Pharmaceutically acceptable salts include acid addition salts formed with inorganic acids such as, for example, hydrochloric or phosphoric acids, or with organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Administration of immunogenic compositions, therapeutic formulations, medicaments and prophylactic formulations is generally by conventional routes e.g. intravenous, subcutaneous, intraperitoneal, or mucosal routes. The administration may be by parenteral injection, for example, a subcutaneous, intradermal or intramuscular injection. For example, formulations comprising antibodies or expanded NK cell populations of the invention may be particularly suited to administration intravenously, intramuscularly, intradermally, or subcutaneously. Administration of small molecule REV-ERB inhibitors may be injection, such as intravenously, intramuscularly, intradermally, or subcutaneously, or by oral administration (small molecules with molecule weight of less than 500 Da typically exhibiting oral bioavailability).

Accordingly, immunogenic compositions, therapeutic formulations, medicaments and prophylactic formulations of the invention may be prepared as injectables, either as liquid solutions or suspensions. Solid forms suitable for solution in, or suspension in, liquid prior to injection may alternatively be prepared. The preparation may also be emulsified, or the peptide encapsulated in liposomes or microcapsules.

The active immunogenic ingredients (such as the compounds or expanded NK cell populations of the invention) are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine.

Generally, the carrier is a pharmaceutically-acceptable carrier. Non-limiting examples of pharmaceutically acceptable carriers include water, saline, and phosphate-buffered saline. In some embodiments, however, where the composition comprises a compound of the invention, this may be in lyophilized form, in which case it may include a stabilizer, such as BSA. In some embodiments, it may be desirable to formulate the composition with a preservative, such as thiomersal or sodium azide, to facilitate long term storage.

Examples of additional adjuvants which may be effective include but are not limited to: complete Freunds adjuvant (CFA), Incomplete Freunds adjuvant (IFA), Saponin, a purified extract fraction of Saponin such as Quil A, a derivative of Saponin such as QS-21, lipid particles based on Saponin such as ISCOM/ISCOMATRIX, E. coli heat labile toxin (LT) mutants such as LTK63 and/or LTK72, aluminium hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryl oxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion, the MF59 formulation developed by Novartis, and the AS02, AS01, AS03 and AS04 adjuvant formulations developed by GSK Biologicals (Rixensart, Belgium).

Examples of buffering agents include, but are not limited to, sodium succinate (pH 6.5), and phosphate buffered saline (PBS; pH 6.5 and 7.5).

Additional formulations which are suitable for other modes of administration include suppositories and, in some cases, oral formulations or formulations suitable for distribution as aerosols. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders.

The dosage ranges for administration of the compounds of the present invention are those which produce the desired therapeutic effect. It will be appreciated that the dosage range required depends on the precise nature of the compound, the route of administration, the nature of the formulation, the age of the patient, the nature, extent or severity of the patient's condition, contraindications, if any, and the judgement of the attending physician. Variations in these dosage levels can be adjusted using standard empirical routines for optimisation. Similarly, the dose of a compound of the invention for use in a method of the invention, particularly an ex vivo method, can be readily determined by one of skill in the art, and is any dose that produces the desired increase in NK cell number and/or elicits the desired expansion in NK cells, to produce an expanded NK cell population. As a non-limiting example, doses of SR8278 according to the present invention may give rise to a final concentration of about 2 to about 20 µM, about 2 to about 15 µM, about 5 to about 15 µM, about 5 to about 14 µM, about 4 to about 13 µM, about 5 to about 12 µM, about 5 to about 11 µM, or preferably about 5 to about 10 µM.

The invention also provides the use of an expanded NK cell population (as described herein) in a pharmaceutical formulation. Any and all of the disclosure herein in relation to formulations of a compound of the invention may apply equally and independently to therapeutic applications of the expanded NK cell populations of the invention.

Key to SEQ ID NOs

-E4bp4 gene sequence (X64318.1)

SEQ ID NO: 1

```
   1 gccccttcct ttctcctcgt cggcccgaga gcaggaacac gataacgaag gaggcccaac
  61 ttcattcaat aaggagcctg acggatttat cccagacggt agaacaaaag gaagaatatt
 121 gatggatttt aaaccagagt ttttaaagag cttgagaata cggggaaatt aatttgttct
 181 cctacacaca tagatagggt aaggttgttt ctgatgcagc tgagaaaaat gcagaccgtc
 241 aaaaaggagc aggcgtctct tgatgccagt agcaatgtgg acaagatgat ggtccttaat
 301 tctgctttaa cggaagtgtc agaagactcc acaacaggtg aggacgtgct tctcagtgaa
 361 ggaagtgtgg ggaagaacaa atcttctgca tgtcggagga acgggaatt cattcctgat
 421 gaaaagaaag atgctatgta ttgggaaaaa aggcggaaaa ataatgaagc tgccaaaaga
 481 tctcgtgaga agcgtcgact gaatgacctg gttttagaga acaaactaat tgcactggga
 541 gaagaaaacg ccactttaaa agctgagctg ctttcactaa aattaaagtt tggtttaatt
 601 agctccacag catatgctca agagattcag aaactcagta attctacagc tgtgtacttt
 661 caagattacc agacttccaa atccaatgtg agttcatttg tggacgagca cgaaccctcg
 721 atggtgtcaa gtagttgtat ttctgtcatt aaacactctc cacaaagctc gctgtccgat
 781 atggtgtcaa gtagttgtat ttctgtcatt aaacactctc cacaaagctc gctgtccgat
 841 agtcctgaaa acaagttcca gattatcaag caagagccga tggaattaga gagctacaca
 901 agggagccaa gagatgaccg aggctcttac acagcgtcca tctatcaaaa ctatatgggg
 961 aattcttttct ctgggtactc acactctccc ccactactgc aagtcaaccg atcctccagc
1021 aactccccga gaacgtcgga aactgatgat ggtgtggtag gaaagtcatc tgatggagaa
1081 gacgagcaac aggtccccaa gggccccatc cattctccag ttgaactcaa gcatgtgcat
1141 gcaactgtgg ttaaagttcc agaagtgaat tcctctgcct tgccacacaa gctccggatc
1201 aaagccaaag ccatgcagat caagtagaa gcctttgata tgaatttga ggccacgcaa
1261 aaactttcct cacctattga catgacatct aaaagacatt tcgaactcga aaagcatagt
1321 gccccaagta tggtacattc ttctcttact cctttctcag tgcaagtgac taacattcaa
1381 gattggtctc tcaaatcgga gcactggcat caaaaagaac tgagtggcaa aactcagaat
1441 agtttcaaaa ctggagttgt tgaaatgaaa gacagtggct acaaagtttc tgacccagag
1501 aacttgtatt tgaagcaggg gatagcaaac ttatctgcag aggttgtctc actcaagaga
1561 cttatagcca cacaaccaat ctctgcttca gactctgggt aaattactac tgagtaagag
1621 ctgggcattt agaaagatgt catttgcaat agagcagtcc attttgtatt atgctgaatt
1681 ttcactggac ctgtgatgtc atttcactgt gatgtgcaca tgttgtctgt ttggtgtctt
1741 tttgtgcaca gattatgatg aagattagat tgtgttatca ctctgcctgt gtatagtcag
1801 atagtcatat gcgtaaggct gtatatatta agntttatt tttgttgttc tattataaag
1861 tgtgtaagtt accagtttca ataaaggatt ggtgacaaac acagaaaaaa aaaaaaaaaa
1921 aaa
```

-E4bp4 amino acid sequence (X64318.1)

SEQ ID NO: 2

MQLRKMQTVKKEQASLDASSNVDKMMVLNSALTEVSEDSTTGEDVLLSEGSVGKNKSSACRRKREFIPDEKKDAM

YWEKRRKNNEAAKRSREKRRLNDLVLENKLIALGEENATLKAELLSLKLKFGLISSTAYAQEIQKLSNSTAVYFQ

DYQTSKSNVSSFVDEHEPSMVSSSCISVIKHSPQSSLSDVSEVSSVEHTQESSVQGSCRSPENKFQIIKQEPMEL

ESYTREPRDDRGSYTASIYQNYMGNSFSGYSHSPPLLQVNRSSSNSPRTSETDDGVVGKSSDGEDEQQVPKGPIH

SPVELKHVHATVVKVPEVNSSALPHKLRIKAKAMQIKVEAFDNEFEATQKLSSPIDMTSKRHFELEKHSAPSMVH

-continued

SSLTPFSVQVTNIQDWSLKSEHWHQKELSGKTQNSFKTGVVEMKDSGYKVSDPENLYLKQGIANLSAEVVSLKRL

IATQPISASDSG

-REV-ERBα gene sequence (NM_021724.4)

SEQ ID NO: 3

```
   1 gggcacgagg cgctccctgg gatcacatgg tacctgctcc agtgccgcgt gcggcccggg
  61 aaccctgggc tgctggcgcc tgcgcagagc cctctgtccc agggaaaggc tcgggcaaaa
 121 ggcggctgag attggcagag tgaaatatta ctgccgaggg aacgtagcag ggcacacgtc
 181 tcgcctcttt gcgactcggt gccccgtttc tccccatcac ctacttactt cctggttgca
 241 acctctcttc ctctgggact tttgcaccgg gagctccaga ttcgccaccc cgcagcgctg
 301 cggagccggc aggcagaggc accccgtaca ctgcagagac ccgaccctcc ttgctacctt
 361 ctagccagaa ctactgcagg ctgattcccc tacacactc tctctgctct tcccatgcaa
 421 agcagaactc cgttgcctca acgtccaacc cttctgcagg gctgcagtcc ggccacccca
 481 agaccttgct gcagggtgct tcggatcctg atcgtgagtc gcggggtcca ctccccgccc
 541 ttagccagtg cccaggggc aacagcggcg atcgcaacct ctagtttgag tcaaggtcca
 601 gtttgaatga ccgctctcag ctggtgaaga catgacgacc ctggactcca acaacaacac
 661 aggtggcgtc atcacctaca ttggctccag tggctcctcc ccaagccgca ccagccctga
 721 atccctctat agtgacaact ccaatggcag cttccagtcc ctgacccaag gctgtcccac
 781 ctacttccca ccatccccca ctggctccct cacccaagac ccggctcgct cctttgggag
 841 cattccaccc agcctgagtg atgacggctc cccttcttcc tcatcttcct cgtcgtcatc
 901 ctcctcctcc ttctataatg ggagcccccc tgggagtcta caagtggcca tggaggacag
 961 cagccgagtg tccccagca agagcaccag caacatcacc aagctgaatg catggtgtt
1021 actgtgtaaa gtgtgtgggg acgttgcctc gggcttccac tacggtgtgc acgcctgcga
1081 gggctgcaag ggcttttccc gtcggagcat ccagcagaac atccagtaca aaaggtgtct
1141 gaagaatgag aattgctcca tcgtccgcat caatcgcaac cgctgccagc aatgtcgctt
1201 caagaagtgt ctctctgtgg gcatgtctcg agacgctgtg cgttttgggc catccccaa
1261 acgagagaag cagcggatgc ttgctgagat gcagagtgcc atgaacctgg ccaacaacca
1321 gttgagcagc cagtgcccgc tggagacttc acccacccag caccccaccc aggcccat
1381 gggcccctcg ccacccctg ctccggtccc ctcacccctg gtgggcttct cccagtttcc
1441 acaacagctg acgcctccca gatccccaag ccctgagccc acagtggagg atgtgatatc
1501 ccaggtggcc cgggcccatc gagagatctt cacctacgcc catgacaagc tgggcagctc
1561 acctggcaac ttcaatgcca accatgcatc aggtagccct ccagccacca ccccacatcg
1621 ctgggaaaat cagggctgcc cacctgcccc caatgacaac aacaccttgg ctgcccagcg
1681 tcataacgag gccctaaatg tctgcgcca ggctccctcc tcctaccctc ccacctggcc
1741 tcctggcccct gcacaccaca gctgccacca gtccaacagc aacgggcacc gtctatgccc
1801 cacccacgtg tatgcagccc cagaaggcaa ggcacctgcc aacagtcccc ggcagggcaa
1861 ctcaaagaat gttctgctgg catgtcctat gaacatgtac ccgcatggac gcagtgggcg
1921 aacggtgcag gagatctggg aggatttctc catgagcttc acgcccgctg tgcgggaggt
1981 ggtagagttt gccaaacaca tcccgggctt ccgtgacctt tctcagcatg accaagtcac
2041 cctgcttaag gctggcacct tgaggtgct gatggtgcgc tttgcttcgt tgttcaacgt
2101 gaaggaccag acagtgatgt tcctaagccg caccacctac agcctgcagg agcttggtgc
2161 catgggcatg ggagacctgc tcagtgccat gttcgacttc agcgagaagc tcaactccct
```

-continued

```
2221 ggcgcttacc gaggaggagc tgggcctctt caccgcggtg gtgcttgtct ctgcagaccg 2281 ctcgggcatg gagaattccg cttcggtgga gcagctccag gagacgctgc tgcgggctct 2341 tcgggctctg gtgctgaaga accggccctt ggagacttcc cgcttcacca agctgctgct 2401 caagctgccg gacctgcgga ccctgaacaa catgcattcc gagaagctgc tgtccttccg 2461 ggtggacgcc cagtgacccg cccggccggc cttctgccgc tgccccttg tacagaatcg 2521 aactctgcac ttctctctcc tttacgagac gaaaaggaaa agcaaaccag aatcttattt 2581 atattgttat aaaatattcc aagatgagcc tctggccccc tgagccttct tgtaaatacc 2641 tgcctccctc cccatcacc gaacttcccc tcctccccta tttaaaccac tctgtctccc 2701 ccacaacccct cccctggccc tctgatttgt tctgttcctg tctcaaatcc aatagttcac 2761 agctgagctg gcttcaaaaa aaaaaaaaaa aaa
```

-REV-ERBα amino acid sequence (NM_021724.4)

SEQ ID NO: 4

MTTLDSNNNTGGVITYIGSSGSSPSRTSPESLYSDNSNGSFQSLTQGCPTYFPPSPTGSLTQDPARSFGSIPPSL
SDDGSPSSSSSSSSSSSSFYNGSPPGSLQVAMEDSSRVSPSKSTSNITKLNGMVLLCKVCGDVASGFHYGVHACE
GCKGFFRRSIQQNIQYKRCLKNENCSIVRINRNRCQQCRFKKCLSVGMSRDAVRFGRIPKREKQRMLAEMQSAMN
LANNQLSSQCPLETSPTQHPTPGPMGPSPPPAPVPSPLVGFSQFPQQLTPPRSPSPEPTVEDVISQVARAHREIF
TYAHDKLGSSPGNFNANHASGSPPATTPHRWENQGCPPAPNDNNTLAAQRHNEALNGLRQAPSSYPPTWPPGPAH
HSCHQSNSNGHRLCPTHVYAAPEGKAPANSPRQGNSKNVLLACPMNMYPHGRSGRTVQEIWEDFSMSFTPAVREV
VEFAKHIPGFRDLSQHDQVTLLKAGTFEVLMVRFASLFNVKDQTVMFLSRTTYSLQELGAMGMGDLLSAMFDFSE
KLNSLALTEEELGLFTAVVLVSADRSGMENSASVEQLQETLLRALRALVLKNRPLETSRFTKLLLLKLPDLRTLNN
MHSEKLLSFRVDAQ

-REV-ERBβ gene sequence (AB307693.1)

SEQ ID NO: 5

```
   1 atggaggtga atgcaggagg tgtgattgcc tatatcagtt cttccagctc agcctcaagc 61 cctgcctctt gtcacagtga gggttctgag aatagtttcc agtcctcctc ctcttctgtt 121 ccatcttctc caaatagctc taattctgat accaatggta atcccaagaa tggtgatctc 181 gccaatattg aaggcatctt gaagaatgat cgaatagatt gttctatgaa aacaagcaaa 241 tcgagtgcac ctgggatgac aaaaaatcat agtggtgtga caaaatttag tggcatggtt 301 ctactgtgta agtctgtgg ggatgtggcg tcaggattcc actatggagt tcatgcttgc 361 gaaggctgta agggtttctt tcggagaagt attcaacaaa acatccagta caagaagtgc 421 ctgaagaatg aaaactgttc tataatgaga atgaatagga acagatgtca gcaatgtcgc 481 ttcaaaaagt gtctgtctgt tggaatgtca agagatgctg ttcggtttgg tcgtattcct 541 aagcgtgaaa acagaggat gctaattgaa atgcaaagtg caatgaagac catgatgaac 601 agccagttca gtggtcactt gcaaaatgac acattagtag aacatcatga acagacagcc 661 ttgccagccc aggaacagct gcgacccaag ccccaactgg agcaagaaaa catcaaaagc 721 tcttctcctc atcttctga ttttgcaaag gaagaagtga ttggcatggt gaccagagct 781 cacaaggata cctttatgta taatcaagag cagcaagaaa actcagctga gagcatgcag 841 ccccagagag agaacggat tcccaagaac atggagcaat ataatttaaa tcatgatcat 901 tgcggcaatg ggcttagcag ccattttccc tgtagtgaga gccagcagca tctcaatgga 961 cagttcaaag gaggaatat aatgcattac ccanatggcc atgccatttg tattgcaaat 1021 ggacattgta tgaacttctc caatgcttat actcaaagag tatgtgatag agttccgata 1081 gatggatttt ctcagaatga aacaagaat agttacctgt gcaacactgg aggaagaatg 1141 catctggttt gtccaatgag taagtctcca tatgtggatc ctcataaatc aggacatgaa
```

```
1201 atctgggaag aattttcgat gagcttcact ccagcagtga aagaagtggt ggaatttgca 1261 aagcgtattc ctgggttcag agatctctct cagcatgacc aggtcaacct tttaaaggct 1321 gggacttttg aggttttaat ggtacggttc gcatcattat ttgatgcaaa ggaacgtact 1381 gctaccttt  taagtggaaa gaaatatagt gtggatgatt tacactcaat gggagcaggg 1441 gatctgctaa actctatgtt tgaatttagt gagaagctaa atgccctcca acttagtgat 1501 gaagagatga gtttgtttac agctgttgtc ctggtatctg cagatcgatc tggaatagaa 1561 aacgtcaact ctgtggaggc tttgcaggaa actctcattc gtgcactaag gaccttaata 1621 atgaaaaacc atccaaatga ggcctctatt tttacaaaac tgcttctaaa gttgccagat 1681 cttcgatctt taaacaacat gcactctgag gagctcttgg cctttaaagt tcaccctaa
```

-REV-ERBβ amino acid sequence (AB307693.1)

SEQ ID NO: 6

MEVNAGGVIAYISSSSSASSPASCHSEGSENSFQSSSSSVPSSPNSSNSDTNGNPKNGDLANIEGILKNDRIDCS

MKTSKSSAPGMTKNHSGVTKFSGMVLLCKVCGDVASGFHYGVHACEGCKGFFRRSIQQNIQYKKCLKNENCSIMR

MNRNRCQQCRFKKCLSVGMSRDAVRFGRIPKREKQRMLIEMQSAMKTMMNSQFSGHLQNDTLVEHHEQTALPAQE

QLRPKPQLEQENIKSSSPPSSDFAKEEVIGMVTRAHKDTFMYNQEQQENSAESMQPQRGERIPKNMEQYNLNHDH

CGNGLSSHFPCSESQQHLNGQFKGRNIMHYPXGHAICIANGHCMNFSNAYTQRVCDRVPIDGFSQNENKNSYLCN

TGGRMHLVCPMSKSPYVDPHKSGHEIWEEFSMSFTPAVKEVVEFAKRIPGFRDLSQHDQVNLLKAGTFEVLMVRF

ASLFDAKERTVTFLSGKKYSVDDLHSMGAGDLLNSMFEFSEKLNALQLSDEEMSLFTAVVLVSADRSGIENVSNV

EALQETLIRALRTLIMKNHPNEASIFTKLLLKLPDLRSLNNMHSEELLAFKVH

-forward primer A for detection of E4bp4 wildtype allele

SEQ ID NO: 7

CTCTGAGCTTGGCTGATGTG

-reverse primer for the detection of E4bp4

SEQ ID NO: 8

GCTTCAAGTCTCCACCAAGC

-primer for the detection of the E4bp4 null allele

SEQ ID NO: 9

CCATGCTCCTGTCTTGATGA

EXAMPLES

The invention will be further clarified by the following examples, which are intended to be purely exemplary of the invention and are in no way limiting.

Example 1—REV-ERBα Antagonist SR8278 Addition Increases Percentage NK Cell Production Initially, a total of seven compounds (SR8278, Remodelin, GSK343, UNC0638, HKMT-1-005, SGC0946 and (R)-PFI-2) at 5, 10, and 20 μM were screened along with D4476 as a positive control. GSK343, UNC0638, HKMT-1-005, SGC0946 and (R)-PFI-2 are methyltransferase inhibitors. Methyltransferase inhibitors were tested based on the effect of EZH2 inhibitor.

Figure 2:
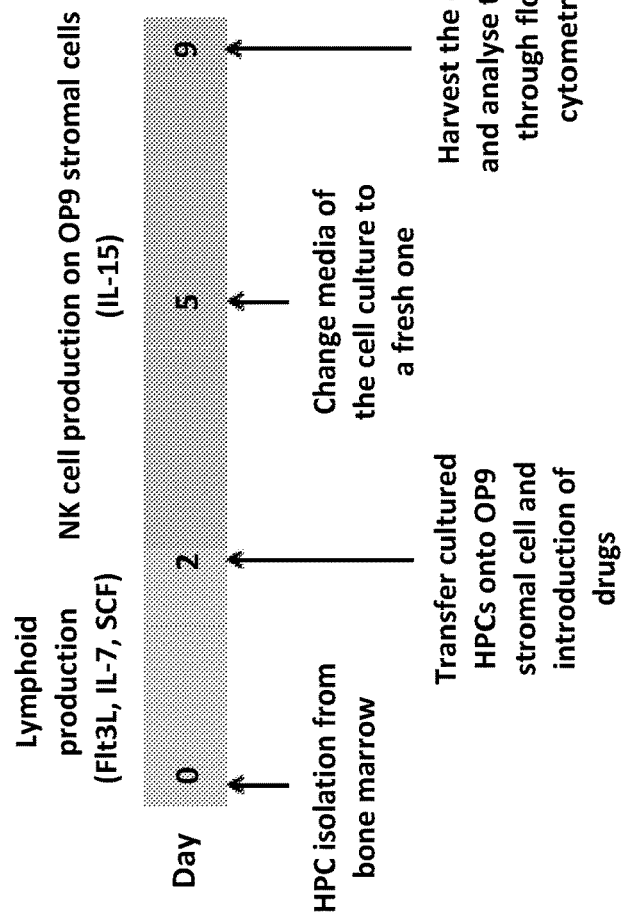
FIG. 2: Timeline of NK cell development assay. HPCs were isolated and cultured plus Flt3L, IL-7 and SCF cytokines. At Day 2, they were then transferred onto OP9 stromal cells plus or minus drug in culture medium plus the IL-15 cytokine. The media of the cultures were changed at Day 5 and the cells were harvested and analysed at Day 9.
Figure 3:
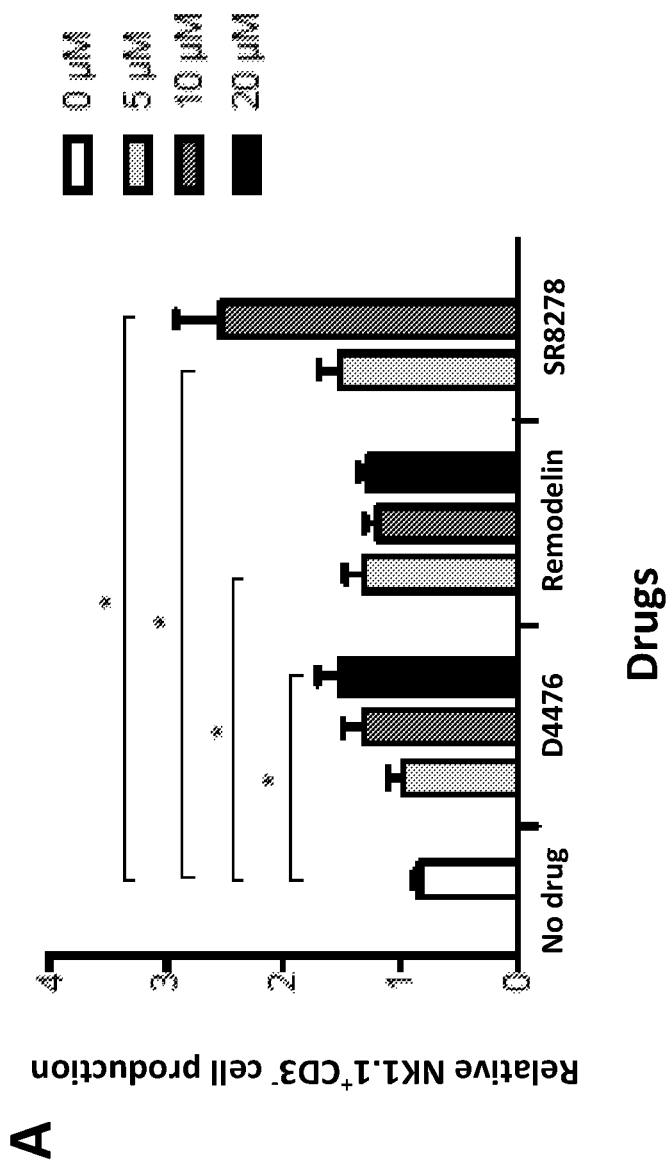
FIG. 3: HPCs were cultured in NK cell-producing conditions with the addition of different drug compounds at Day 2. At Day 9, percentage of NK cells was quantified using flow cytometry. (A) Graph showing relative mature mouse NK cell ($NK1.1^+$ $CD3^-$) production for the addition of 5, 10 and 20 μM D4476 (positive control), Remodelin and SR8278 compared to the 'No drug' control. (B) Flow cytometry gating strategy for the identification of mouse NK cells. (C) Representative flow cytometry results with percentage of NK cells shown. Results were averaged from one experiment with six repeats and the error bars represent the mean+SD. Asterisks indicate significant differences from the two annotated results (* is $P \leq 0.01$) based on Mann-Whitney test.
Figure 3:
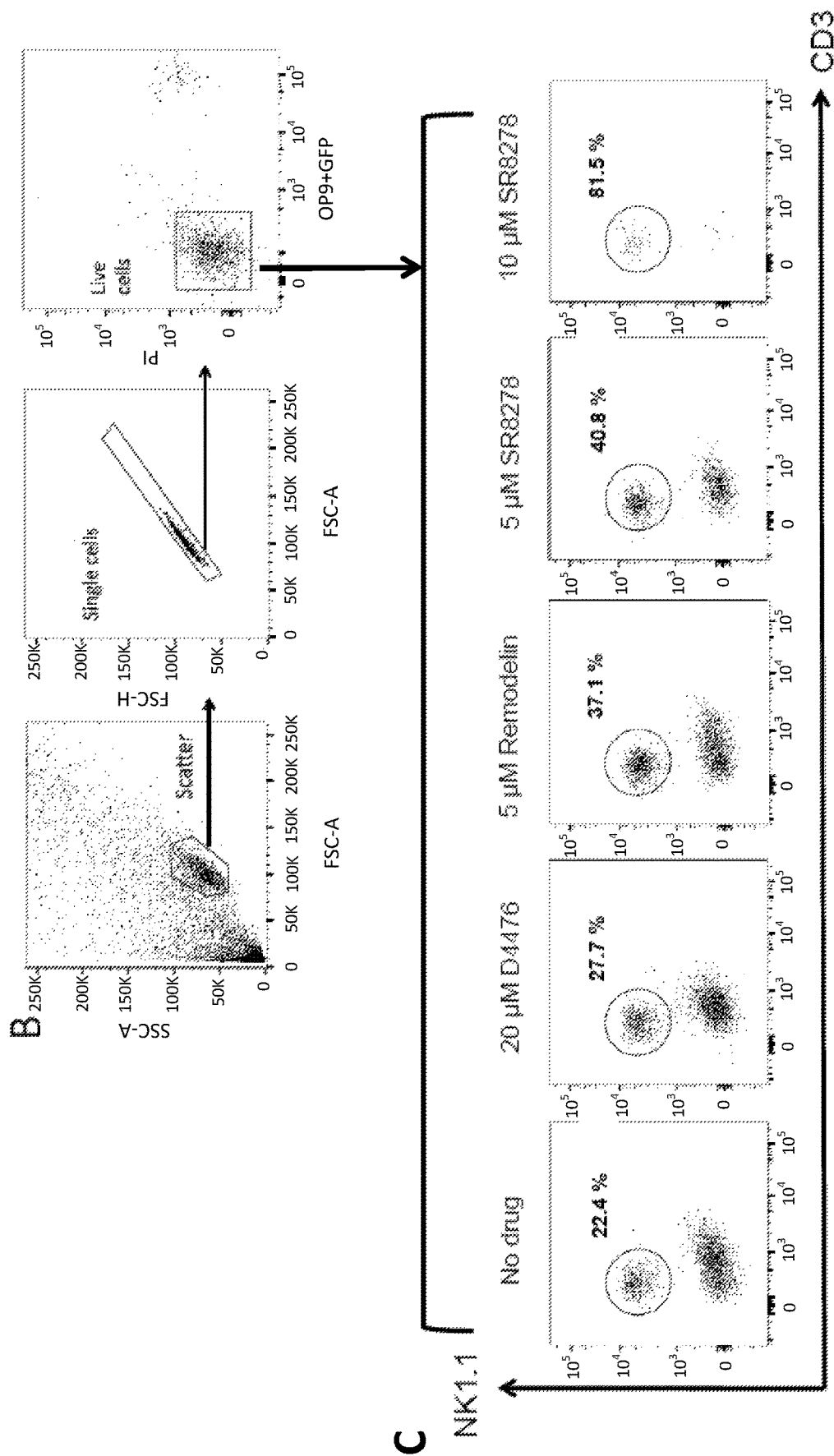

Lineage negative cells are enriched for Hematopoietic Progenitor Cells (HPCs). HPCs were isolated and cultured for a total of 9 days and the drugs added on Day 2 (FIG. 2). Cells were harvested on Day 9 and analysed using flow cytometry to determine the number of NK1.1$^+$ CD3$^-$ cells (FIG. 2). NK1.1$^+$ and CD3$^-$ are two cell surface markers that can define mouse NK cells. OP9 stromal cells were readily excluded from the analysis, as the OP9 stromal cells used were GFP positive (FIG. 3B). Flow cytometry data were analysed as the fold increase, relative to the 'No drug' or untreated control in each experiment. This is because the absolute percentage of NK cell production varies between experiments.

Figure 4:
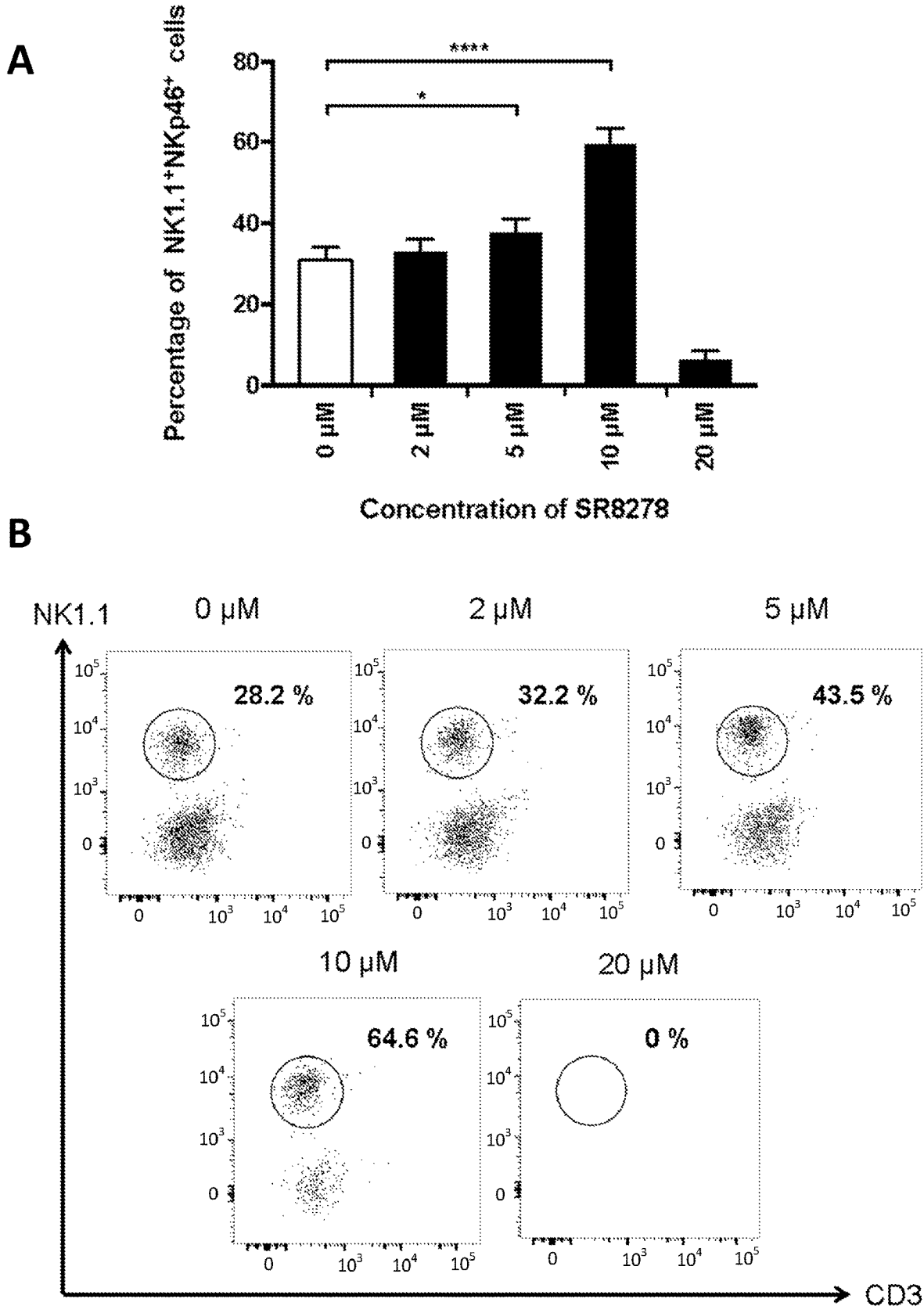
FIG. 4: HPCs were cultured in NK cell-producing conditions with the addition of different concentrations of SR8278. At Day 9, percentage of NK cells was quantified using flow cytometry. (A) Graph showing relative mature mouse NK cell ($NK1.1^+$ $CD3^-$) production for the addition of 2, 5, 10 and 20 μM SR8278 compared to the 'No drug' control. Results were averaged from three independent experiments with biological duplicates and technical triplicates and the error bars represent the mean+SD. Asterisks indicate significant differences from the two annotated results (* is $P \leq 0.05$; **** is $P \leq 0.001$) based on Mann-Whitney test. (B) Representative (exemplary) flow cytometry results with percentage of NK cells shown.

Out of the seven new compounds tested, only 2 compounds showed a significant increase in NK cell production (FIG. 3A), where others did not (data not shown). The addition of 201 μM D4476 as well as 5 μM Remodelin showed a significant increase but not as striking as 10 μM SR8278 (FIGS. 3A and 3C). When 10 μM SR8278 was added, the NK cell production increased over 2.4 fold when compared to the 'No drug' control (FIGS. 3A and 3C). However at 20 μM SR8278, the compound was toxic and killed most of the cells, hence there was a reduction in the number of NK cells detected (FIG. 4). Further experiments were done using SR8278 at 2, 5, 10 and 20 μM to confirm its activity. The results were consistent with the previous screen. 10 μM SR8278 showed the highest increase in NK cell production, followed by 5 μM (FIG. 4).

Example 2—Optimisation of Time of Addition of SR8278

Figure 5:
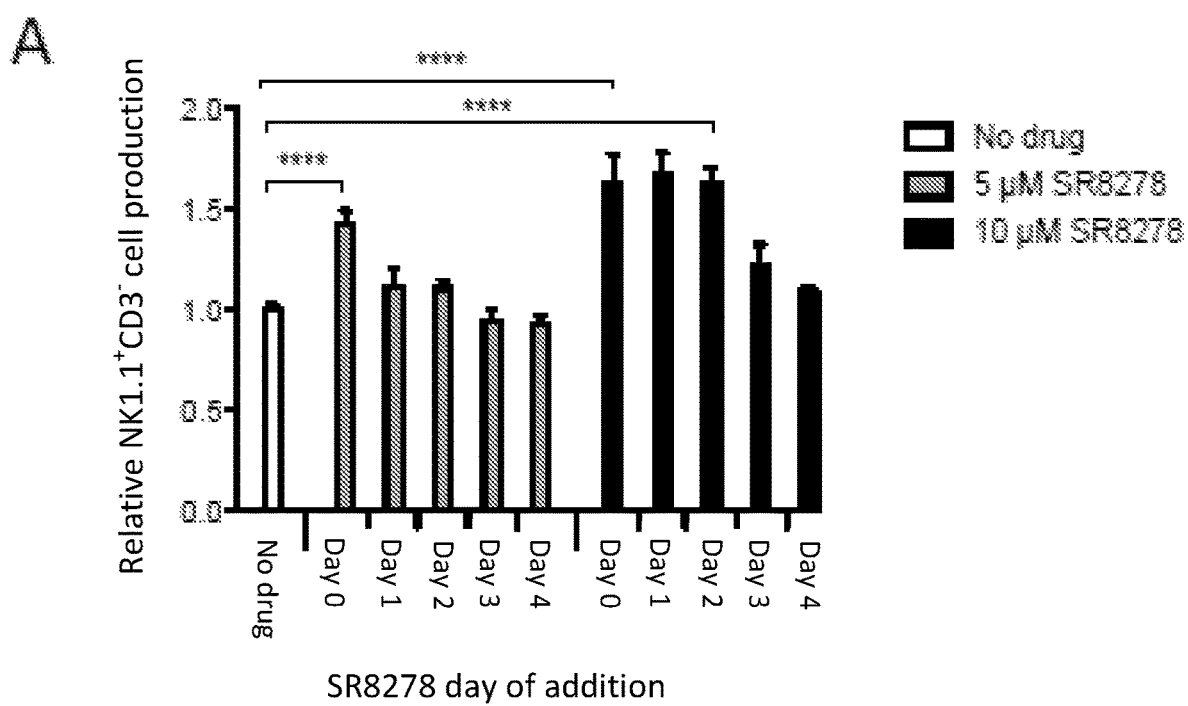
FIG. 5: Lineage negative cells (HPCs) were cultured in NK cell-producing conditions with the addition of 5 or 10 μM SR8278 on Day 0, 1, 2, 3 or 4. At Day 9, percentage of NK cells was quantified using flow cytometry. (A) Graph showing relative mature mouse NK cell (NK1.1+ CD3−) production when 5 and 10 μM SR8278 were added on different days compared to the 'No drug' control. (B) Representative flow cytometry results with percentage of NK cells shown. Addition of 5 μM SR8278 is shown on the top, whereas addition of 10 μM SR8278 is shown on the bottom. (C) Graph shows the number of live cells when 5 and 10 μM of SR8278 were added on different days. Results were averaged from two experiments with four repeats each and the error bars represent the mean+SD. Asterisks indicate significant differences from the two annotated results (* is $P \leq 0.01$, * is $P \leq 0.0001$ and ** is $P \leq 0.00001$) based on Mann-Whitney test.
Figure 5:
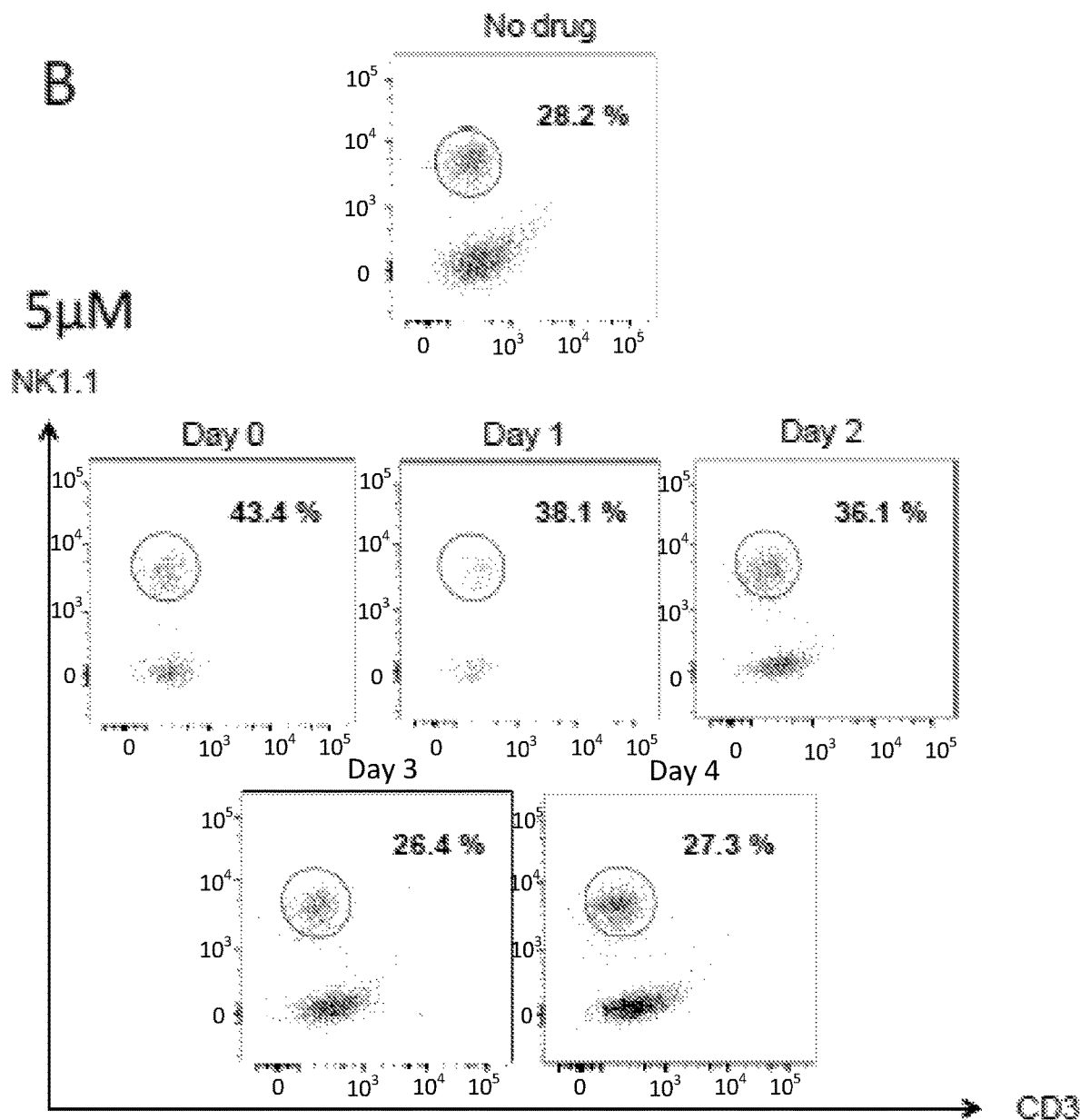
Figure 5B:
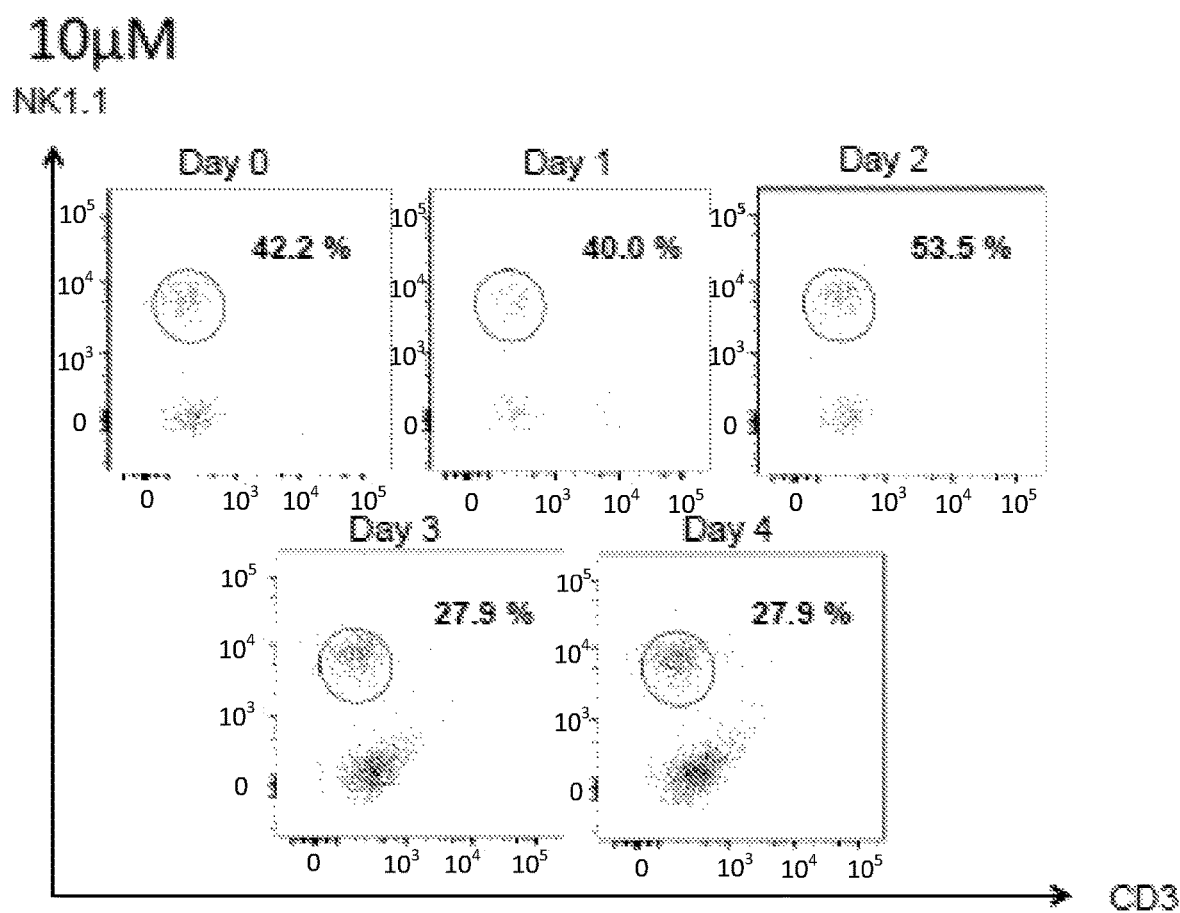
Figure 5:
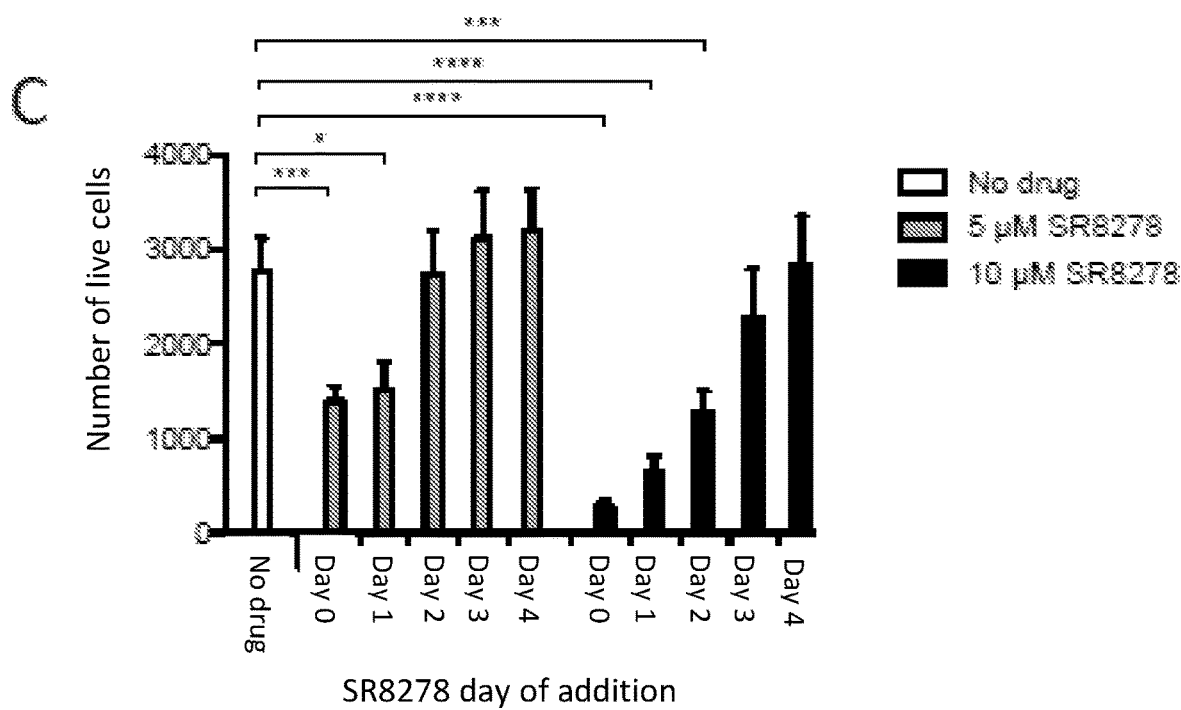

The effects of SR8278 were further examined. In particular the best time to add SR8278 to the cell culture was investigated. SR8278 was added on Day 0, 1, 2, 3 and 4 of HPC culture in NK cell-producing conditions. The experiment was done using 5 and 10 μM SR8278. At 5 μM, the addition of SR8278 showed the greatest effect of NK cell production at Day 0 with over 1.4-fold (FIGS. 5A and 5B). As expected, the addition of 10 μM SR8278 showed higher increase in NK cells production compared to 5 μM (FIGS. 5A and 5B). The increase was significant on Days 0, 1 and 2, at over 1.6-fold (FIGS. 5A and 5B). However, the addition of SR8278 after Day 2 showed no significant difference relative to the 'No drug' control.

Even though the addition of SR8278 at Days 0 and 1 showed the greatest increase in the percentage NK cells, the numbers of live cells were remarkably low when compared to the 'No drug' control (FIG. 5C). It is possible that when SR8278 was added to enhance E4bp4 expression at Day 0 or Day 1, the cells were not primed to differentiate into CLPs or NKPs. Too high dose or too early addition of SR8278 is not sustainable. From these results, Day 2 is the optimum time to add SR8278 to the HPC culture, providing maximal NK cell productions, as well as preserving high live cells counts.

Example 3—Administration of the REV-ERB Agonist. GSK4112, has the Opposite Effect to SR8278

It is predicted that the effect of SR8278 in the increase of NK cells resulted from the inhibition of REVERB, which normally inhibits E4bp4 expression. Therefore, the REV-ERB agonist, GSK4112, was tested to see whether it would lead to a decrease in NK cell production. HPC culture plus the addition of GSK4112 was performed exactly as previously shown in FIG. 3.

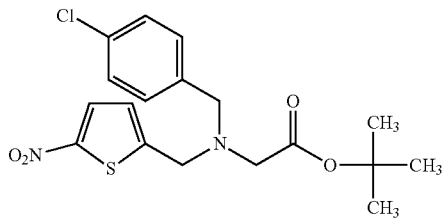 [SMILES: CC(C)(C)OC(=O)CN(Cc1ccc(Cl)cc1)Cc1ccc([N+](=O)[O-])s1]

Structure of GSK4112 (1,1-Dimethylethyl N-[(4-chlorophenyl)methyl]-N-[(5-nitro-2-thienyl)methyl]) glycinate, SR6452)

Figure 6:
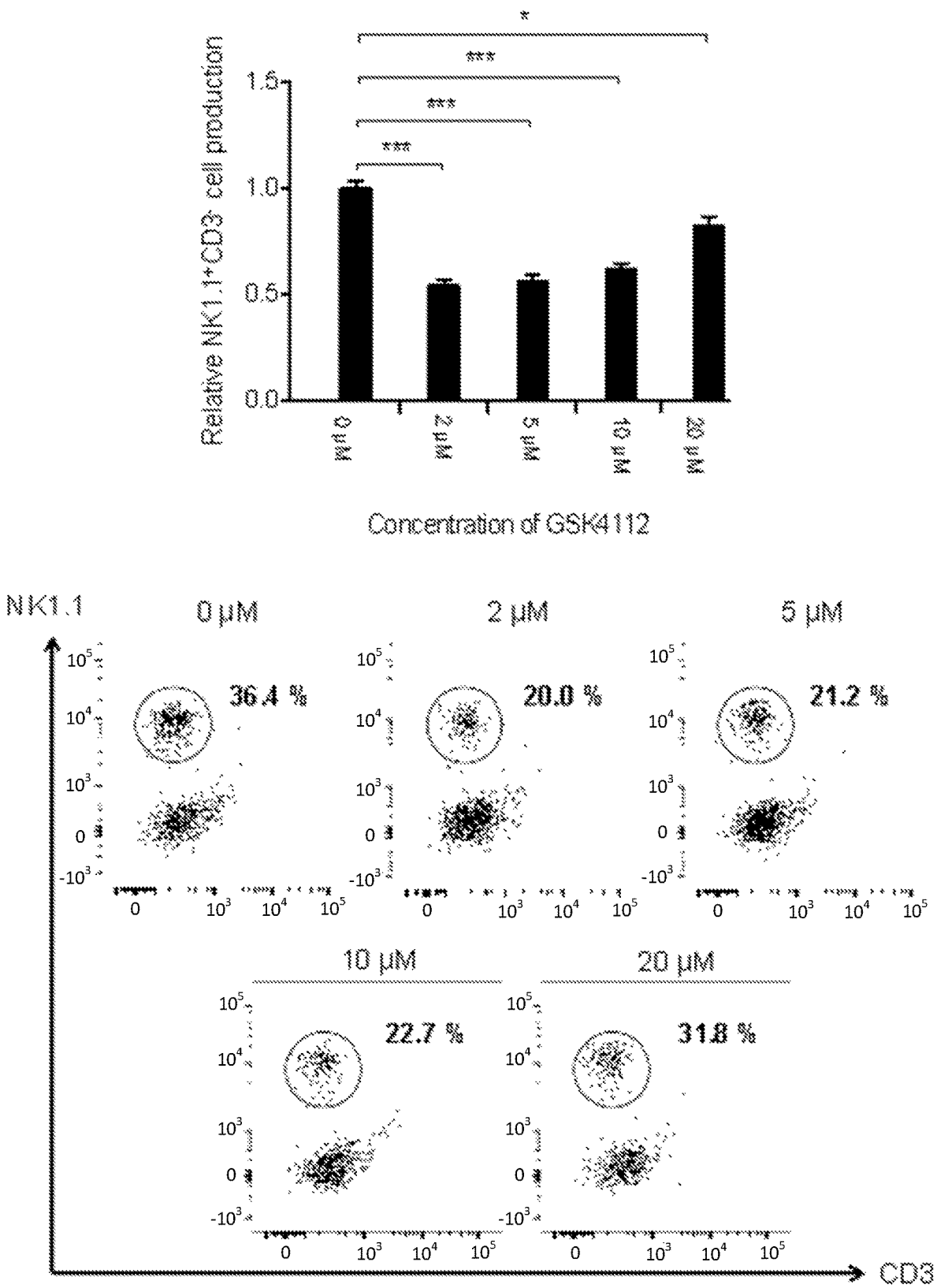
FIG. 6: HPCs were cultured in NK cell-producing conditions with the addition of different concentrations of GSK4112. At Day 9, percentage of NK cells was quantified using flow cytometry. (A) Graph showing relative mature mouse NK cell (NK1.1+ CD3−) production for the addition of 2, 5, 10 and 20 μM GSK4112 compared to the 'No drug' control. (B) Representative flow cytometry results with percentage of NK cells shown. Results were averaged from two experiments with four repeats each and the error bars represent the mean+SD. Asterisks indicate significant differences from the two annotated results (* is $P \leq 0.01$ and *** is $P \leq 0.0001$) based on Mann-Whitney test.

As predicted, NK cell production was reduced by nearly 50%, when GSK4112 was administered (FIG. 6). This supports that regulation of REV-ERB results in the control of NK cell development via modulation of E4bp4 expression and that GSK4112 and SR8278 act in this pathway involving REV-ERB-α and E4bp4.

Example 4—SR8278 Acts on NK Cells Via E4bp4

Following the experiment with GSK4112, it was predicted that SR8278 acts through the pathway involving REV-ERB and E4bp4. To confirm whether SR8278 requires E4bp4 to increase NK cell production, SR8278 was tested on HPCs isolated from wild type (WT) (E4bp4$^{-/-}$), E4bp4 knock-out (KO) (E4bp4$^{-/-}$) and heterozygous (Het) (E4bp4$^{-/-}$) mice. Cell cultures were performed as previously (FIG. 3), where SR8278 was added on Day 2 of the culture and NK cell production was measured by flow cytometry.

Figure 7:
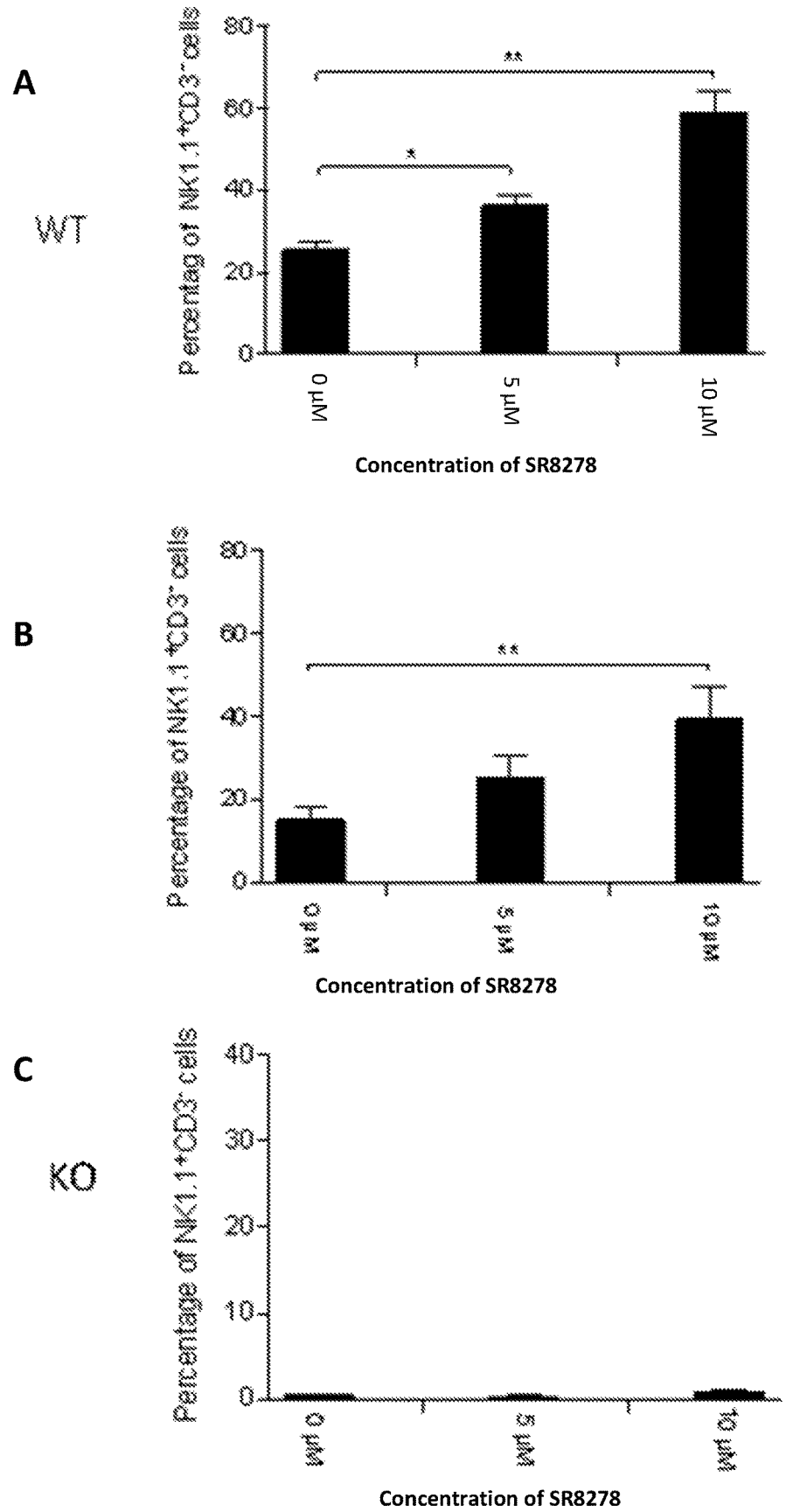
FIG. 7: HPCs isolated from either wild type (WT), E4bp4 knockout (KO) or heterozygous (Het) mice were cultured with the addition of 5 or 10 μM SR8278. At Day 9, percentage of NK cells was quantified using flow cytometry. Graph showing relative mature mouse NK cell (NK1.1$^+$ CD3$^-$) production compared to the 'No drug' control in experiments with (A) WT, (B) Het and (C) E4bp4 KO mice. (D) Representative flow cytometry results with percentage of NK cells shown for the addition of 10 µM SR8278. Results were averaged from two experiments with four repeats each and the error bars represent the mean+SD. Asterisks indicate significant differences from the two annotated results (* is P≤0.01 and ** is P≤0.001) based on Mann-Whitney test.
Figure 7:
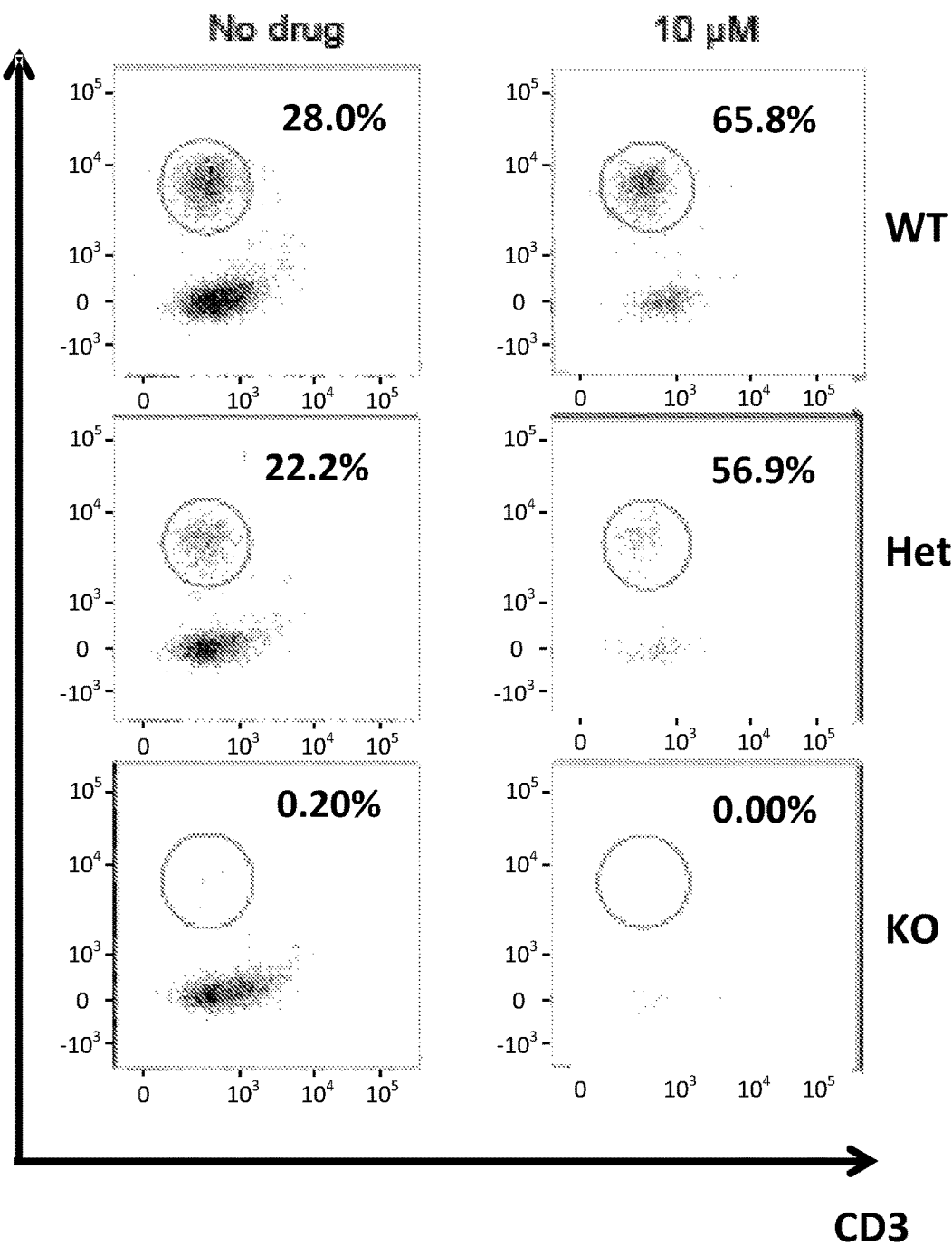

Unlike the previous Examples where the data were shown in fold difference in relation to the 'No drug' control, these data are shown as actual percentages of NK cells produced. This is because when E4bp4 KO mice were used, the percentage of NK cell in the 'No drug' control was virtually zero as the absence of E4bp4 halts NK cell development (FIGS. 7C and 7D). The largest significant increase can be seen when 5 μM and 10 μM SR8278 were added to HPCs in culture isolated from WT mice compared to the 'No drug' control (FIGS. 7A and 7D). The effects of culture of HPCs from Het mice were similar to WT mice (FIGS. 7A, 7B and 7D). On the other hand, there was an absent of NK cells in cultures of HPCs from E4bp4 KO mice regardless of SR8278 concentration (FIGS. 7C and 7D).

These data support the hypothesis that SR8278 acts on the pathway in which E4bp4 is essential. The presence of E4bp4 is mandatory for SR8278 to successfully increase NK cell production. SR8278 can inhibit the activity of REV-ERB, where REV-ERB normally inhibits E4bp4 expression. Therefore, the inhibition of REV-ERB by SR8278 derepresses E4bp4 expression. The activation of E4bp4 results in the promotion of NK cell development and more NK cells produced (FIG. 1).

Example 5—Addition of SR8278 Increases the Expression of E4bp4. Id2 and Eomes

Figure 8:
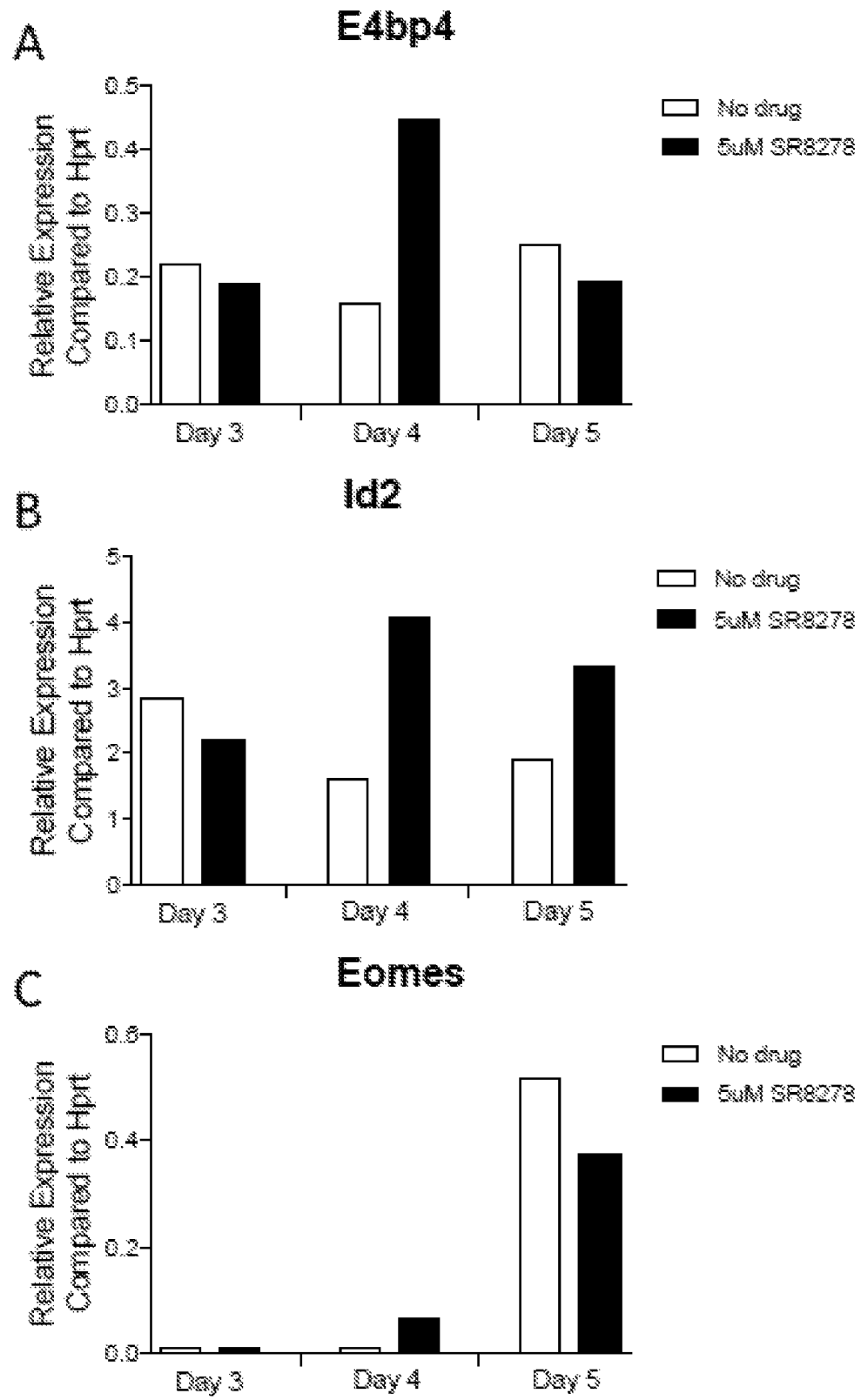
FIG. 8: HPCs were cultured with or without 5 µM SR8278 added on Day 2. At Day 3, 4 and 5, cells were harvested in order to quantify their relative cytokines expressions by RT-qPCR. The graphs show relative expression of (A) E4bp4, (B) Id2 and (C) Eomes normalized to the housekeeping gene, Hprt.

As the data presented in the above Examples indicates that SR8278 likely acts on the pathway with REV-ERB and E4bp4, it was predicted that genes which are under transcriptional control of E4bp4 such as Id2 and Eomes should be upregulated when E4bp4 expression is upregulated. HPCs isolated from a WT mouse were cultured as previously (FIG. 2) but the cells were harvested and analysed using RT-qPCR on Day 3, 4 and 5. The relative expression of the E4bp4, Id2 and Eomes genes was compared to the housekeeping gene, Hprt. At Day 4, E4bp4, Id2 and Eomes expression was higher in SR8278 treated samples when compared to the 'No drug' control (FIG. 8). The increase in E4bp4 expression disappeared at Day 5 but the increase of Id2 expression remained (FIG. 8B). The upregulation of E4bp4 and its downstream targets happens in a matter of hours and only stays high for a defined period of time.

These data therefore support the conclusion that SR8278 activates expression of the E4bp4 transcription factor gene, since the known downstream targets of E4bp4 (21) were concomitantly upregulated as well.

Example 6—SR8278 Also Enhances NK Cell Development from Human CD34$^+$ Cells

The hypothesis that SR8278 increases NK cells production would not have any potential therapeutic value if it was not also true for human NK cell production. Therefore, the effect of SR8278 on human NK cell production from human HPCs was examined. Human HPCs were obtained as the CD34$^+$ population purified from umbilical cord blood from collaborators at the Anthony Nolan Research Institute, London. Human NK cell development goes through a similar developmental pathway to mouse NK cell development. By contrast with mouse HPC culture, human CD34$^+$ cells were cultured straight onto EL08-1D2 stromal cells in the presence of IL-3, IL-7, Flt3L, SCF and IL-15 cytokines for 14 and 16 days before harvesting and analysis by flow cytometry. To try to optimise human NK cell production, 5 or 10 μM SR8278 were added on either day 2, 4 or 6 of the culture.

Figure 9:
FIG. 9: Human CD34$^+$ cells were cultured with the addition of 5 µM SR8278 at Day 4. At Day 14 and 16, percentage of hCD56$^+$ hCD45$^+$ (markers for human NK cells) cells was quantified using flow cytometry. (A) Graph showing percentage of hCD56$^+$ hCD45$^+$ cells compared to the 'No drug' control in different conditions. (B) Flow cytometry gating strategy for identification of human NK cells. (C) Representative flow cytometry results with percentage of NK cells shown. Results were averaged from one experiments with six repeats each and the error bars represent the mean+SD.
Figure 9:
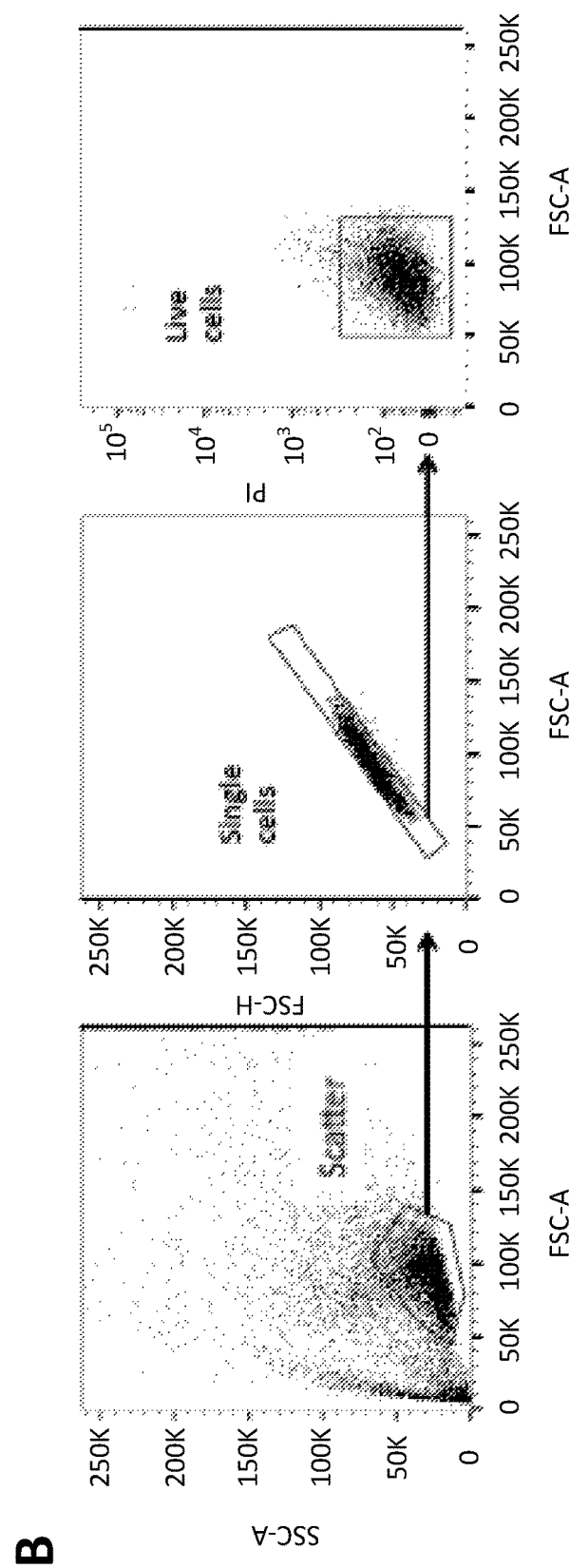
Figure 9:
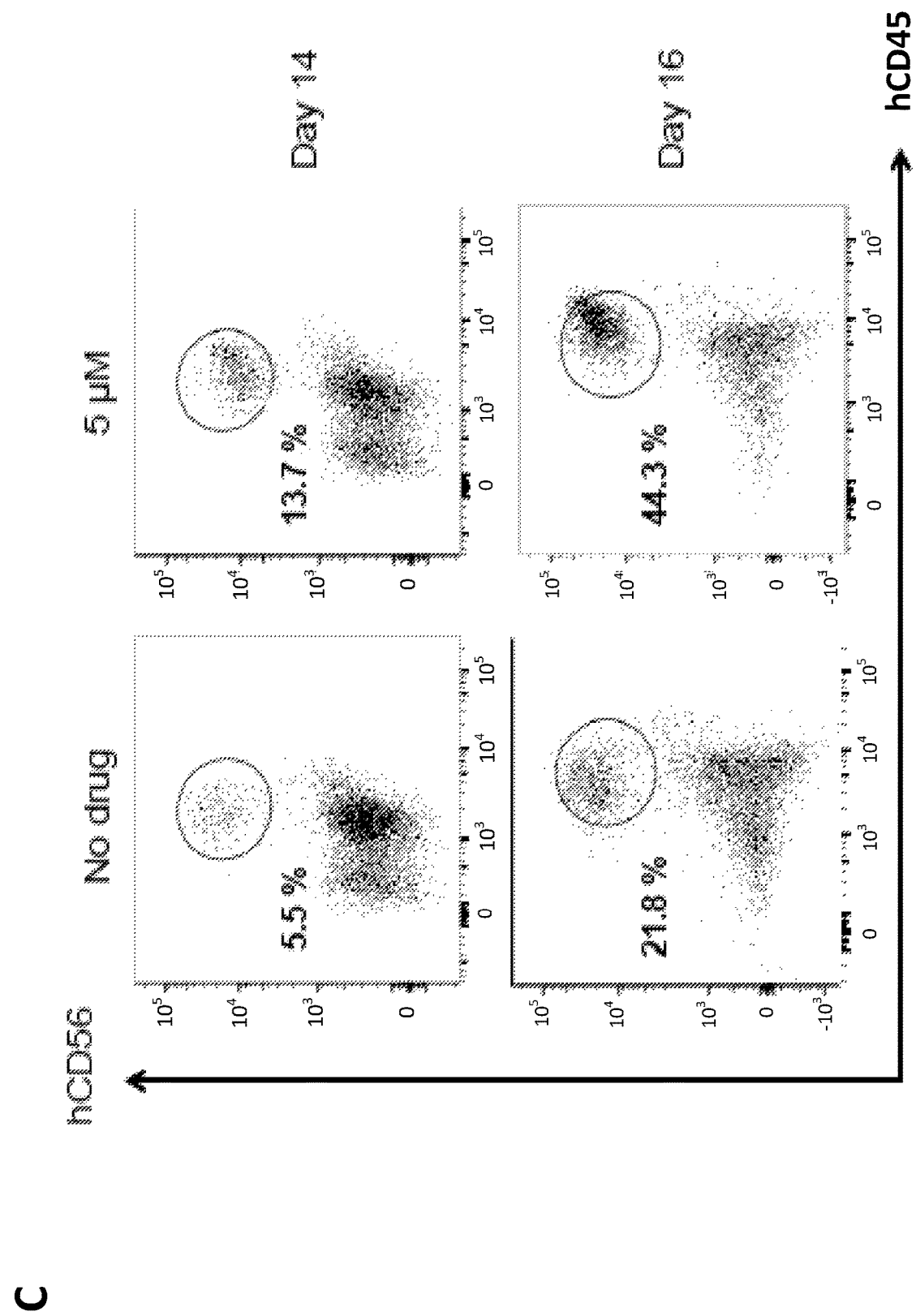

The data showed that human CD34+ cells were more sensitive to SR8278 than mouse HPCs as addition of 10 μM SR8278 was completely toxic to the cells. However, the effect at 5 μM SR8278 was not toxic and the addition of 5 μM SR8278 on Day 2 showed a clear increase in NK cell number (FIG. 9). Data are shown as percentage of NK cell because from Day 14 to Day 16, the number of NK cell increased exponentially from 5% to 20% in the 'No drug' control (FIG. 9). Addition of 5 μM SR8278 at Day 4 almost tripled the percentage of NK cells when the cells were harvested at Day 14, increasing from 5.53% to 13.7% (FIG. 9). On the other hand, the percentage of NK cell doubled when harvested at Day 16, increasing from 21.8% to 44.3% (FIG. 9).

Example 7—E4bp4 May be Inhibited by Both REV-ERBα and REV-ERBβ

Previous work has emphasised the action of REV-ERB-α in inhibiting E4bp4 expression, but the role for the REV-ERB homologue REV-ERB-β has not been investigated. In the present investigation, it was therefore decided to directly examine the effect of deleting the REV-ERB-α gene on NK cell production. The previous Examples suggest that REV-ERB-α KO mice would enhance E4bp4 expression and hence enhance NK cell development. HPCs extracted from bone marrow as well as splenocytes taken from WT (Rev-erb-α$^{+/+}$) and REV-ERB-α KO mice (Rev-erb-α$^{-/-}$) were therefore analysed by flow cytometry. If REV-ERB-α is responsible for the regulation of NK cell production, there should be an increased number of NKP and NK cells in the bone marrow and potentially, also the spleen.

Figure 10:
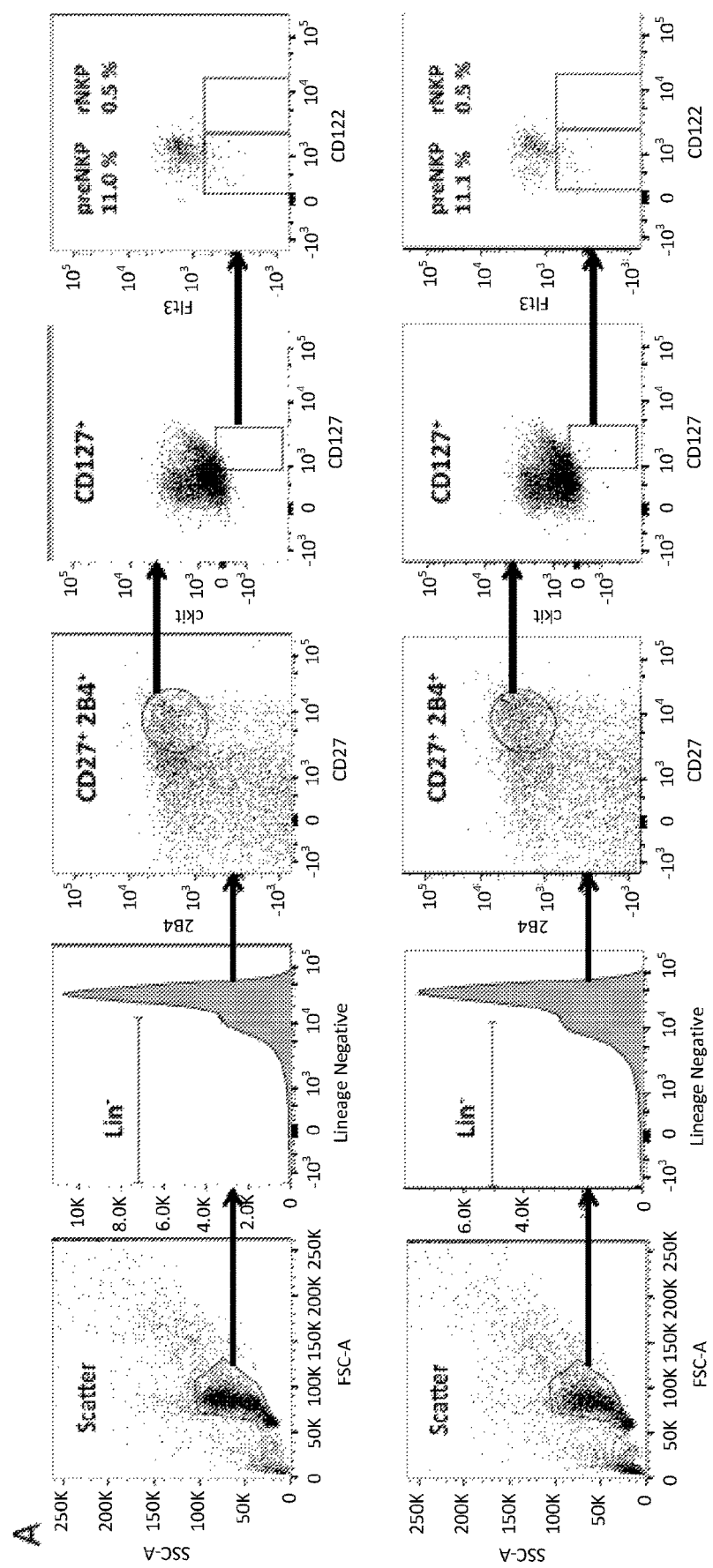
FIG. 10: (A) Flow cytometry gating strategy for identification of preNKPs and rNKPs in the bone marrow of WT (Top) and REV-ERB-α KO (Bottom) mice. Percentage of gated population is shown on each flow cytometry graphs (B) Flow cytometry results with percentage of NK cells shown for the identification of mouse NK cells in bone marrow (BM) and spleen of WT and REV-ERB-α KO mice. The results were obtained by using the gating strategy in FIG. 3B.
Figure 10:
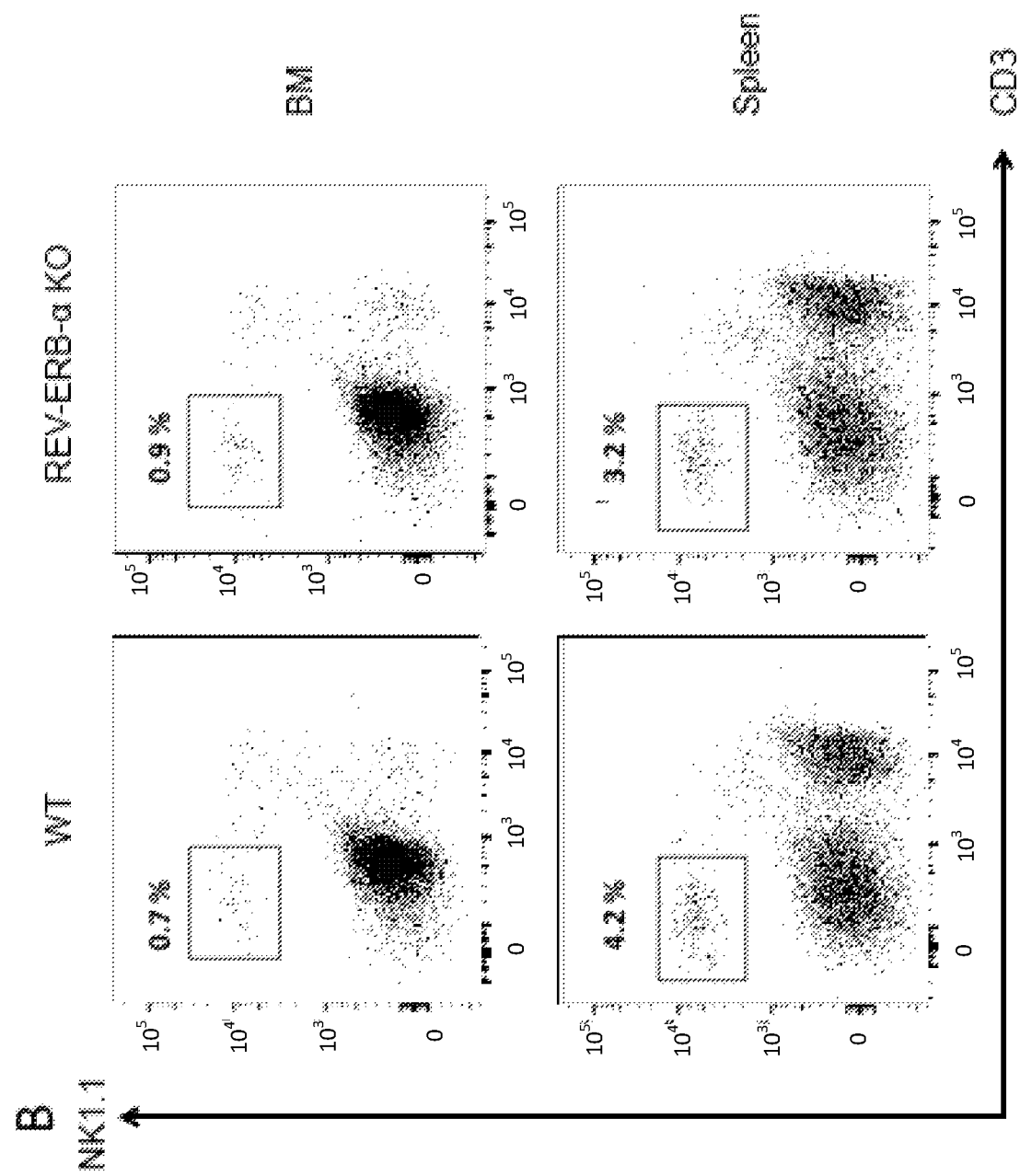

However, as shown in FIG. 10, in REV-ERB-α KO mice, the percentage of NK and NKP cells were no different from the WT. These findings suggest that both REV-ERB-α and REV-ERB-β, which is a homologue of REV-ERB-α may be inhibiting E4bp4 expression. When REV-ERB-α is missing, REVERB-β may compensate for the activity of REV-ERB-α. Supporting this hypothesis, chromatin immunoprecipitate experiments on REV-ERB-α and REV-ERB-β have shown that both REV-ERB-α and REV-ERB-β bind to the E4bp4 locus at exactly the same regions. Moreover, SR8278 is actually a dual inhibitor, inhibiting both REVERB-α and REV-ERB-β. Therefore, the increase in NK cells when SR8278 was administered may result from the inhibition of both REV-ERBs.

Figure 11:
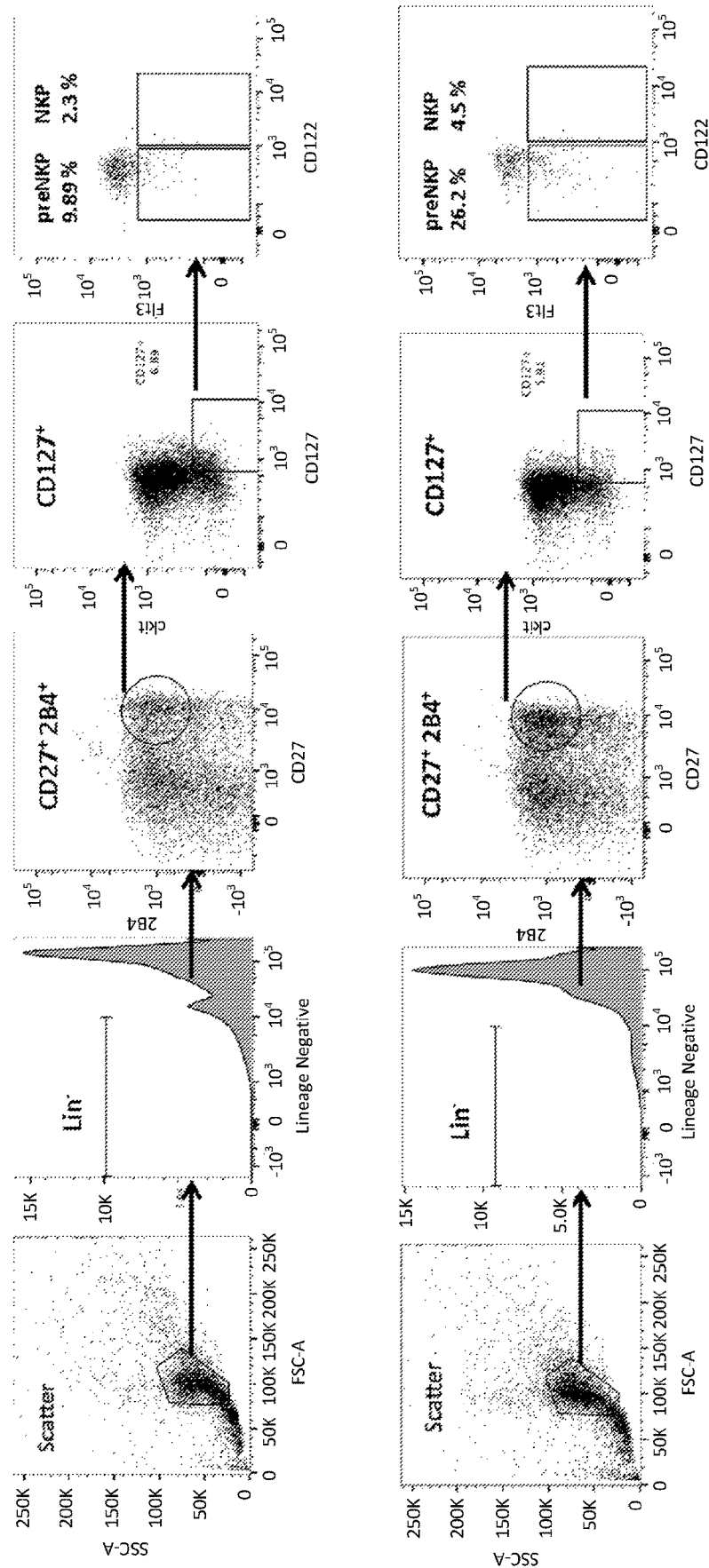
FIG. 11: (A) Flow cytometry gating strategy for identification of preNKPs and rNKPs in the bone marrow of WT (Top) and REV-ERB-α and REV-ERB-β double KO (Bottom) mice. Percentage of gated population is shown on each flow cytometry graphs. (B) Analysis of bone marrow of REV-ERBα/β double KO mice. DKO=mice with both REV-ERBα and β genes deleted, αHet/βHet=mice with only one allele of each REV-ERB gene deleted and βKO=mice with the REV-ERB β gene deleted. N=2 for each data point. LMPP=lymphoid-myeloid pluripotent progenitor cells, CLP=common lymphoid progenitor cells & NKP=NK cell progenitor cells. The y-axis indicates that these cell numbers are represented as percentage of the total lineage-negative cell population of bone marrow.
Figure 11:
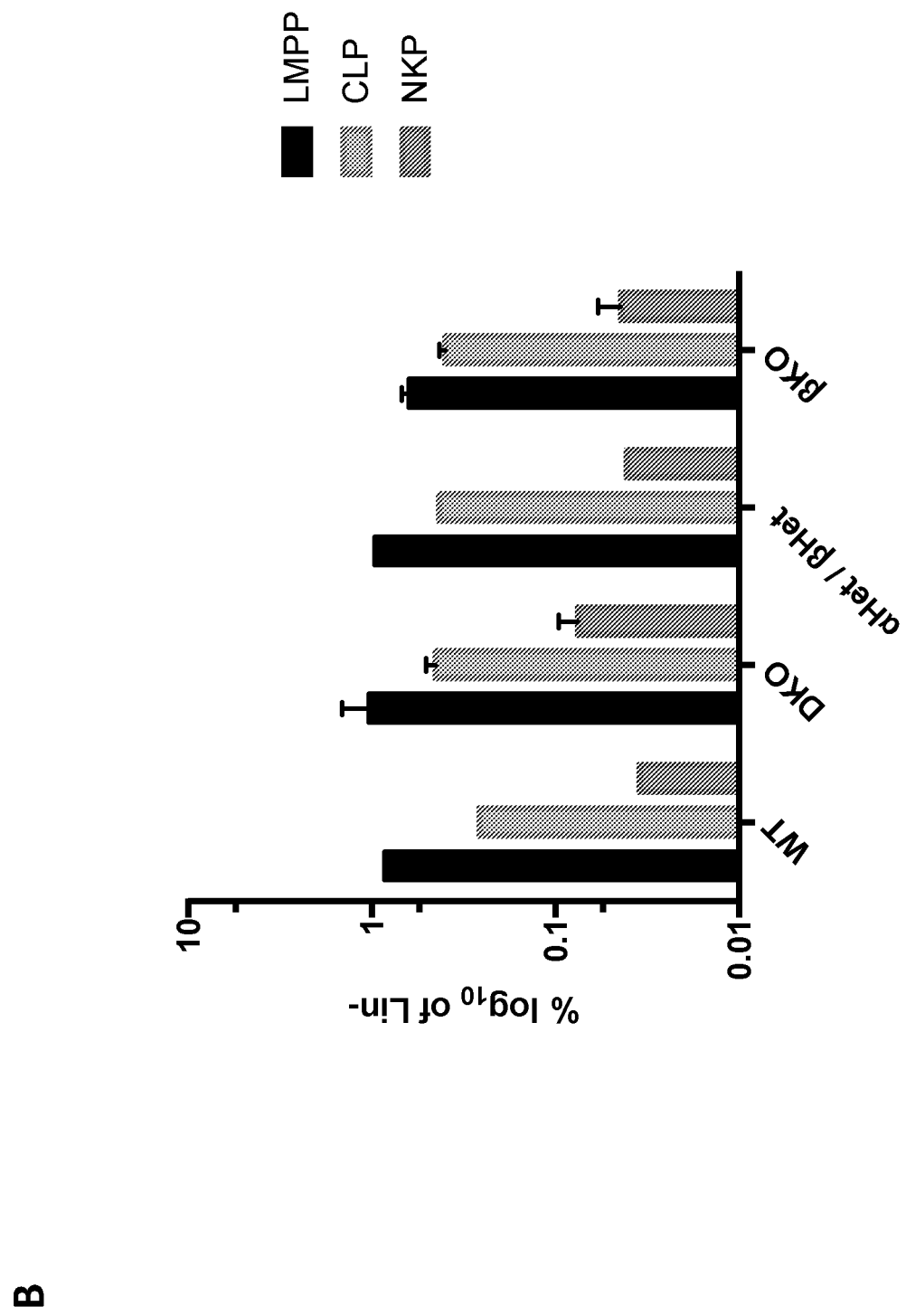

This is supported by the data reported in FIG. 11A, which demonstrates that mice deficient in both REV-ERB-α and REV-ERB-β have a very significant increase in the number of NKP cells. FIG. 11B provides further evidence in support of the joint role of REV-ERB-α and REV-ERB-13. FIG. 11B shows that in mutant mice with both REV-ERB genes deleted (DKO) there is a consistent increase in NKP cells numbers compared to other "control" mice (WT, mice with only one allele of REV-ERB-α and REV-ERB-β deleted (αHet/βHet), and mice with both copies of REV-ERB-β deleted (βKO)), whereas other progenitor cells are not affected.

Therefore, the present inventors have provided the first evidence that inhibition of both REV-ERB-α and REV-ERB-β, has therapeutic potential to increase NK cell number, and that such inhibition may be achieved using compounds of the invention such as SR8278.

Materials and Methods

Mice

Wild type mice, E4bp4 heterozygous mice (E4bp4$^{+/-}$), E4bp4 knockout mice (E4bp4$^{-/-}$), REV-ERB-α knockout mice (Rev-erb-α$^{-/-}$), REV-ERB-β knockout mice (Rev-erb-β$^{-/-}$ or βKO), REV-ERB-α and β double knockout mice (Rev-erb-α$^{-/-}$β$^{-/-}$ or DKO) and REV-ERB-α and β heterozygous mice (Rev-erb-α$^{+/-}$β$^{+/-}$ or αHet/βHet) were used. All mice were on a C57BL/6 background, between 6 and 12 weeks old and matched for age and gender. Rbpj$^{flox/flox}$ mice were on a FVB background. All animal husbandry and experimental procedures were carried out according to UK Home Office regulations and local guidelines. E4bp4 mice were genotyped with the forward primer 5'CTCTGAGCTTGGCTGATGTG3' (primer A) and reverse primer 5'GCTTCAAGTCTCCACCAAGC3' (primer B) for detection of the wild type allele or 5'CCATGCTCCTGTCTTGATGA3' for detection of the null allele.

Cells and Cell Culture

OP9-GFP stromal cells were cultured in Iscove's Modified Dulbecco's Media (IMDM) (Sigma Aldrich) supplemented with 20% Fetal Bovine Serum (FBS), and Penicillin/Streptavidin (P/S). For experiments done on 96-well plates, OP9 stromal cells were plated at the concentration of 2000 cells/well and incubated at 37° C., 5% $CO_2$ for 1 day before the addition of HPCs. For experiments done on 24-well plates, OP9 stromal cells were plated at the concentration of 4000 cells/well and were incubated at 37° C. 5% $CO_2$ for 2 days prior to addition of HPCs. EL08.1D2 stromal cells were cultured in Minimum Essential Medium Eagle—Alpha Modification (Alpha-MEM) supplemented with 50% Myelocult M5300 (Stem Cell Technologies), 7.5% FBS, 50 μM β-Mercaptoethanol, 1 μM Hydrocortisone and 1% P/S (Sigma Aldrich). For human CD34$^+$ progenitor cell experiments, EL08.1D2 were irradiated at 3000 rads/30 Gy and plated in 96-well EmbryoMax Gelatin (Millipore)-coated plates at the concentration of 20,000 cells/well. There were cultured at 32° C., 5% $CO_2$ overnight, before CD34$^+$ cells were transferred onto them.

Mouse HPC Isolation

Lineage negative HSCs were purified from mouse bone marrow by crushing the leg bones in Phosphate-buffered Saline (PBS) with 2% fetal calf serum (FCS) (STEMCELL Technologies), topped up to 40 ml with magnetic-activated cell sorting (MACS) buffer (PBS, 2 mM EDTA, 0.5% BSA, sterile and filtered) and centrifuged at 800 g for 2 minutes. The cells were resuspended in PE-conjugated cocktail, (20 μl of anti-B220 (RA3-6B2), anti-mouse CD2 (RM2-5, anti-Ter119 (TER119) and anti-NK.1.1 (PK136) and 5 μl of anti-CD11b (M1/70) and anti-GR-1 (RB6-8C5) antibodies (all from Bioscience)) incubated for 5 minutes at 4° C., centrifuged and resuspended in anti-PE microbeads for 15 minutes at 4° C. Cells were washed in MACS buffer and passed through MACS columns. This allowed negative selection of HPCs. Following lineage depletion, 50 pIl of the cells was analysed using flow cytometry to check for purity.

In Vitro Development of NK Cells from HPCs

The HPCs were plated and cultured in 24-well plates at a concentration of 5×10$^5$ HPCs/well in 1 ml of complete cytokine medium (Dulbecco's modified eagle medium (DMEM) (Sigma Aldrich), 10% FCS, 50 μM β-Mercaptoethanol, 10 ng/ml Flt3-ligand (Flt3L) (R&D Systems), 10 ng/ml IL-7 (R&D Systems), 100 ng/ml stem cell factor (SCF) (R&D Systems) and 1% P/S) for 2 days at 37° C., 5% $CO_2$. The HPCs were then transferred onto OP9 cells at 4500 cells/well for 96-well plate experiments and 3×10$^4$ cells/well for 24-well plate experiments in mouse NK cells differentiation medium (Alpha-MEM (Sigma Aldrich) plus 20% FCS, 1% P/S and 30 ng/ml IL-15). Cells were left in culture at 37° C., 5% $CO_2$ for 7 days with a change of mouse NK cells differentiation medium at day 3 or 4.

In Vitro Development of Human Umbilical Cord Blood Progenitor Cells

CD34+ umbilical cord blood progenitor cells were provided by Anthony Nolan Research Institute, University College London. These cells were isolated from whole cord blood and were cryopreserved in liquid nitrogen for storage and transport. Cells were thawed, counted and then plated on EL08.1D2 plates prepared previously at a concentration of 1000 cells/well in human NK cells differentiation medium (Alpha-MEM plus 20% Human AB serum (Invitrogen), 50 µM β-Mercaptoethanol and 1% P/S along with 5 ng/ml human-IL-3 (Peprotech), 20 ng/ml human-IL-7 (Peprotech), 10 ng/ml human-Flt3-L (Peprotech), 20 ng/ml human-SCF (Peprotech) and 10 ng/ml human-IL-15 (Peprotech). Note that human-IL-3 is only needed for the first week of culture. Cells were left in the culture at 37° C., 5% $CO_2$ for 14 or 16 days with a change of human NK differentiation medium at day 7 and 12.

Flow Cytometry

Cells to be analysed by flow cytometry were passed through 40 µm cell strainers to remove clumps and washed with PBS buffer, centrifuged at 800 g for 2 minutes and resuspended in 100111 fluorescent activated cell sorting (FACS) buffer (PBS plus 1% BSA) with appropriate fluorochrome conjugated antibodies at a dilution of 1 in 300. Cells were stained with the following antibodies, all of which were anti-mouse and are from eBioscience unless specified: 2B4 (clone m2B4(B6)458.1; BioLegend), CD2 (RM2-5), CD3 (17A2), CD11b (M1/70), CD19 (1D3), CD27 (LG.7F9), CD122 (TM-b1), CD127 (A7R34), B220 (RA3-6B2), ckit (ACK2), Flt3 (A2F10), Gr1 (RB6-8C5), NK1.1 (PK136), Sca1 (D7), Ter119 (TER119), NKp46 (29A1.4) anti-human CD45 (H130), anti-human CD2 (RPA-2.10) and anti-human CD56 (CMSSB). The lineage cocktail contained B220, CD2, CD11b, Gr1, NK1.1, and Ter119. Cells were stained in the dark at 4° C. for 30 minutes and then washed with 2 ml FACS buffer, centrifuged and resuspend in 300 µl FACS buffer plus Propidium Iodide (PI) also at a dilution of 1 in 300. Flow cytometry was performed using LSRFortessa™ cell analyser (Becton Dickinson Bioscience), sorted using FACSAria (Becton Dickinson) as indicated and full data analysis was done using FlowJo Software.

Polymerase Chain Reaction (PCR)

Individual PCR reactions contained 200 µM dNTPS, 1 µM forward primer (Primer A), 1 µM reverse primer (Primer B or C) and 0.5 U Taq polymerase. PCR reactions were set to the following conditions: 94° C. for 3 minutes (1 cycle); 94° C. for 30 seconds, 59° C. for 3 seconds, 72° C. for 45 seconds (40 cycles); 72° C. for 3 minutes (1 cycle); hold at 4° C.

DNA Electrophoresis

DNA electrophoresis was performed using 1% agarose (Sigma) dissolved in TAE buffer plus 500 ng/ml Ethidium Bromide (Sigma). DNA obtained from PCR reactions was analysed by gel electrophoresis was performed at 100 volts for approximately 45 minutes. Gels were imaged using EC3 Imaging System (Ultra Violet Products Ltd).

RNA Purification

RNA was extracted using Qiagen RNeasy Micro Kit according to the manufacture's protocol (Qiagen). Centrifugation was done at 8000 g for 15 seconds and the flow through discarded. Briefly, 350 µl of Buffer RLT+10% β-Mercaptoethanol were added to the harvested cells. RNA was further precipitated using 300 µl of 70% ethanol and transferred to RNeasy MinElute Spin Column and centrifuged. Next, 350 µl of buffer RW1 was added to the MinElute Spin Column and centrifuged. This was followed by the addition of 10 µl of DNase I (Qiagen) and 70 µl Buffer RDD (Qiagen) and left at room temperature for 15 minutes. 350 µl of Buffer RW1 was added to wash off DNase I and centrifuged. 500 µl of Buffer RPE was then added to the column and centrifuged, followed by the addition of 500 µl of 80% ethanol and centrifuged for 2 minutes. Finally, 14 µl of RNase-free water was added to elute the RNA and the column was spun for 1 minute at full speed. The concentration of RNA in each sample was measured using Nanodrop, and all samples were diluted to the same working concentration.

Reverse Transcription (Conversion of RNA into cDNA)

Reverse transcription was performed using Transcriptor First Strand cDNA Synthesis kit (Roche). Following the manufacturer's protocol, a template-primer mixture for one 20 µl reaction was prepared, where all reagents were provided in the kit: RNA (1 µg to 5 µg), 2 µl Random Hexamer Primer, top the reaction up to 13 µl with water (PCR-grade). Next, the template-primer mixture was denatured by heating the tube for 10 minutes at 65° C. to remove RNA secondary structures. To that template-primer mixture, 4 µl of Transcriptor Reverse Transcriptase Reaction Buffer, 0.5 µl of Protector RNase Inhibitor, 2 µl of Deoxynycleotide Mix and 0.5 µl of Transcriptor Reverse Transcriptase was added. The reagents was mixed and placed In a thermal block cycler with the following settings: 25° C. for 10 minutes; 55° C. for 30 minutes; 85° C. for 5 minutes and store at 4° C.

Quantification of Targeted Expressed RNA Using Realtime qPCR

| Temperature (° C.) | Time |
|---|---|
| 95 | 20 minutes |
| 95 | 3 seconds |
| 96 | 30 seconds |

Conditions Used for RT-qPCR

A standard curve was constructed using splenocytes cDNA diluted to 1, 1:10, 1:100, 1:1000 and 1:10000. To the 2 µl of cDNA produced in the previous step, 5 µl Taqman master mix (Applied Biosystem), 0.5 µl of Taqman gene expression assay kit of Hprt, Nfil3, Id2 or Eomes (Applied Biosystem) and 2.5 µl of RNase-free water. The program used is shown in Table 1 and the reaction was run for 47 cycles.

Statistical Analysis

Statistical analysis was done using Mann-Whitney test in GraphPad Prism 7

DISCUSSION

NK cells are lymphocytes that are capable of producing cytokines, influencing other immune cells as well as killing cancerous, pathogen-infected or damaged cells directly. Due to these properties, researchers are interested in boosting the number of NK cells in order to enhance cytotoxicity against cancerous or pathogen-infected cells. NK cells develop from HSCs in the bone marrow and are controlled by a tightly regulated process involving various transcription factors and cytokines. E4bp4 is the most critical gene regulating NK cell development. E4bp4 has a profound effect on NK cell production despite there being only a relatively small increase in E4bp4 mRNA levels during NK cell development. Little is known about any means that exist to control the activity of E4bp4 protein. The ability to control E4bp4 expression would have highly significant implications for the development and production of NK cells.

The present inventions have demonstrated that upon administration of SR8278, the production of NK cells in NK cell production assays increases more than 2-fold. In the assays conducted, the optimum time to add SR8278 to the HPC culture for in vitro NK cell production was at Day 2 and the optimum dose was 10 μM.

Since SR8278 is known to inhibit REV-ERB, an agonist of REV-ERB (GSK4112) was then tested and found to have the opposite effect to SR8278, decreasing NK cell production. This underlines the hypothesis that manipulation of the activity of REVERB may effect NK cell production.

The importance of the presence of E4bp4 for SR8278 function was further investigated. HPCs were isolate from WT, E4bp4 KO and Het mice. In the absence of E4bp4 in E4bp4 KO mice, SR8278 was found to have no effect on the production of NK cells. In order for SR8278 to perform its activity in increasing NK cell production, at least one allele of E4bp4 must be present.

As E4bp4 plays a critical role in the action of SR8278 in increasing NK cell production, the expression of genes that are under transcriptional control of E4bp4 such as Id2 and Eomes was tested, and found to be concomitantly upregulated.

The addition of SR8278 was also found to significantly increase human NK cell development from human HPCs cultured in vitro.

Previous experiments emphasized the role of REV-ERB-α in inhibiting E4bp4 expression. To investigate the role of REV-ERB-β, a stain test on NKP and NK cells were done using WT and REV-ERB-α KO mice. The percentage NK and NKP cells were found to be similar in wild type and REV-ERB-α KO. It is therefore possible that REV-ERB-α is not the only transcription factor that regulates E4bp4, but its homologue, REV-ERB-β, may have the same role as well. In the absence of REV-ERB-α, REV-ERB-β would compensate for REV-ERB-α activity as they are highly homologous. This is supported by the data reported herein which demonstrate that double REV-ERB-α and REV-ERB-β KO mice demonstrate an increase in the number of NKP cells compared with control cells, and even compared with REV-ERB-α KO or REV-ERB-α$^{+/-}$ and REV-ERB-β$^{+/-}$ (αHet/βHet) mice.

Control of E4bp4 expression by extrinsic stimuli has significant implications for the production of human NK cells for use in immunotherapy. The conventional methods for the production of NK cells from various sources (e.g. induced-pluripotent stem cells and umbilical cord blood stem cells) involves the use of cytokines and stromal cells to commit the cells to the NK lineage, but influencing E4bp4 expression could provide a simple strategy to enhance the process. Thus, the manipulation of E4bp4 expression has potential utility in the production of future NK cell immunotherapeutic products, including the direct mobilisation of NK cell production in vivo as immunotherapy.

The invention claimed is:

1. An ex vivo method for expanding a natural killer (NK) cell population, comprising the steps of:
   a) culturing an haematopoietic progenitor cell (HPC) comprising sample obtained from a patient;
   b) contacting said sample with a compound which inhibits the action of REV-ERB; and
   c) expanding said cells in vitro to produce an NK cell population.

2. The method of claim 1, wherein said compound increases E4bp4 expression by decreasing REV-ERB activity.

3. The method of claim 1, wherein said compound decreases the activity of REV-ERB-α and/or REV-ERB-β, preferably REV-ERB-β.

4. The method of claim 1, wherein said compound decreases the activity of REV-ERB-α and REV-ERB-β.

5. The method of claim 1, wherein said compound is a REV-ERB antagonist, preferably an antagonist of REV-ERB-α and REV-ERB-β.

6. The method of claim 1, wherein the compound is selected from a small molecule, a PROTAC reagent, a double stranded RNA (dsRNA), a small interfering RNA (siRNA), a small hairpin RNA (shRNA), a micro RNA, an antisense RNA, an aptamer, an antibody, a ribozyme, a peptide or a peptidomimetic.

7. The method of claim 6, wherein the compound is a small molecule.

8. The method of claim 1, wherein the compound is SR8278, ARN5187, ethyl 2-(5-methylfuran-2-carbonyl)-1,2,3,4-tetrahydroisoquinoline-3-carboxylate, 4-((4-chlorobenzyl)((5-nitrothiophen-2-yl)methyl)amino)-N-phenylpiperidine-1-carboxamide, 4(((1-(4-fluorophenyl)cyclopentyl)amino)methyl)-2-((4-methylpiperazin-1-yl)methyl)phenol, 1-(2-fluorophenyl)-N-(3-((1-methylpiperidin-4-yl)methyl)benzyl)cyclopentan-1-amine or 1-(4-fluorophenyl)-N-(3-((1-methylpiperidin-4-yl)methyl)benzyl)cyclopentan-1-amine, preferably SR8278.

9. The method of claim 1, wherein the sample of HPCs is obtained from bone marrow, cord blood and/or peripheral blood.

10. The method of claim 1, wherein the compound is added within 2 days of isolating the HPCs in the sample of claim 1(a).

* * * * *

SEQUENCE LISTING

```
<160> NUMBER OF SEQ ID NOS: 9

<210> SEQ ID NO 1
<211> LENGTH: 1923
<212> TYPE: DNA
<213> ORGANISM: Homo sapiens
<220> FEATURE:
<221> NAME/KEY: misc_feature
<222> LOCATION: (1833)..(1833)
<223> OTHER INFORMATION: n is a, c, g, or t

<400> SEQUENCE: 1
gcccctttct ttctcctcgt cggcccgaga gcaggaacac gataacgaag gaggcccaac      60
ttcattcaat aaggagcctg acggatttat cccagacggt agaacaaaag gaagaatatt     120
gatggatttt aaaccagagt tttaaagag cttgagaata cggggaaatt aatttgttct     180
cctacacaca tagatagggt aaggttgttt ctgatgcagc tgagaaaaat gcagaccgtc     240
aaaaaggagc aggcgtctct tgatgccagt agcaatgtgg acaagatgat ggtccttaat     300
tctgctttaa cggaagtgtc agaagactcc acaacaggtg aggacgtgct tctcagtgaa     360
ggaagtgtgg ggaagaacaa atcttctgca tgtcggagga aacgggaatt cattcctgat     420
gaaaagaaag atgctatgta ttgggaaaaa aggcggaaaa ataatgaagc tgccaaaaga     480
tctcgtgaga agcgtcgact gaatgacctg gttttagaga acaaactaat tgcactggga     540 gaagaaacg ccactttaaa agctgagctg ctttcactaa aattaaagtt tggtttaatt     600
agctccacag catatgctca agagattcag aaactcagta attctacagc tgtgtactt     660 caagattacc agacttccaa atccaatgtg agttcatttg tggacgagca cgaaccctcg     720
atggtgtcaa gtagttgtat ttctgtcatt aaacactctc cacaaagctc gctgtccgat     780
gtttcagaag tgtcctcagt agaacacacg caggagagct ctgtgcaggg aagctgcaga     840
agtcctgaaa acaagttcca gattatcaag caagagccga tggaattaga gagctacaca     900
```

-continued

```
agggagccaa gagatgaccg aggctcttac acagcgtcca tctatcaaaa ctatatgggg      960
aattctttct ctgggtactc acactctccc ccactactgc aagtcaaccg atcctccagc     1020
aactccccga gaacgtcgga aactgatgat ggtgtggtag gaaagtcatc tgatggagaa     1080
gacgagcaac aggtccccaa gggccccatc cattctccag ttgaactcaa gcatgtgcat     1140
gcaactgtgg ttaaagttcc agaagtgaat tcctctgcct tgccacacaa gctccggatc     1200
aaagccaaag ccatgcagat caaagtagaa gcctttgata tgaatttga ggccacgcaa      1260 aaactttcct cacctattga catgacatct aaaagacatt tcgaactcga aaagcatagt     1320
gccccaagta tggtacattc ttctcttact cctttctcag tgcaagtgac taacattcaa     1380
gattggtctc tcaaatcgga gcactggcat caaaagaac tgagtggcaa aactcagaat      1440
agtttcaaaa ctggagttgt tgaaatgaaa gacagtggct acaaagtttc tgacccagag     1500
aacttgtatt tgaagcaggg gatagcaaac ttatctgcag aggttgtctc actcaagaga     1560
cttatagcca cacaaccaat ctctgcttca gactctgggt aaattactac tgagtaagag     1620
ctgggcattt agaaagatgt catttgcaat agagcagtcc attttgtatt atgctgaatt     1680
ttcactggac ctgtgatgtc atttcactgt gatgtgcaca tgttgtctgt ttggtgtctt     1740
tttgtgcaca gattatgatg aagattagat tgtgttatca ctctgcctgt gtatagtcag     1800
atagtcatat gcgtaaggct gtatatatta agntttta t tttgttgttc tattataaag     1860
tgtgtaagtt accagtttca ataaaggatt ggtgacaaac acagaaaaaa aaaaaaaaaa     1920
aaa                                                                  1923
```

<210> SEQ ID NO 2
<211> LENGTH: 462
<212> TYPE: PRT
<213> ORGANISM: Homo sapiens

<400> SEQUENCE: 2

```
Met Gln Leu Arg Lys Met Gln Thr Val Lys Lys Glu Gln Ala Ser Leu
1               5                   10                  15

Asp Ala Ser Ser Asn Val Asp Lys Met Met Val Leu Asn Ser Ala Leu
            20                  25                  30

Thr Glu Val Ser Glu Asp Ser Thr Thr Gly Glu Asp Val Leu Leu Ser
        35                  40                  45

Glu Gly Ser Val Gly Lys Asn Lys Ser Ser Ala Cys Arg Arg Lys Arg
    50                  55                  60

Glu Phe Ile Pro Asp Glu Lys Lys Asp Ala Met Tyr Trp Glu Lys Arg
65                  70                  75                  80

Arg Lys Asn Asn Glu Ala Ala Lys Arg Ser Arg Glu Lys Arg Arg Leu
                85                  90                  95

Asn Asp Leu Val Leu Glu Asn Lys Leu Ile Ala Leu Gly Glu Glu Asn
            100                 105                 110

Ala Thr Leu Lys Ala Glu Leu Leu Ser Leu Lys Leu Lys Phe Gly Leu
        115                 120                 125

Ile Ser Ser Thr Ala Tyr Ala Gln Glu Ile Gln Lys Leu Ser Asn Ser
    130                 135                 140

Thr Ala Val Tyr Phe Gln Asp Tyr Gln Thr Ser Lys Ser Asn Val Ser
145                 150                 155                 160

Ser Phe Val Asp Glu His Glu Pro Ser Met Val Ser Ser Ser Cys Ile
                165                 170                 175

Ser Val Ile Lys His Ser Pro Gln Ser Ser Leu Ser Asp Val Ser Glu
```

```
                    180              185              190
Val Ser Ser Val Glu His Thr Gln Glu Ser Val Gln Gly Ser Cys
                195              200              205
Arg Ser Pro Glu Asn Lys Phe Gln Ile Ile Lys Gln Glu Pro Met Glu
            210              215              220
Leu Glu Ser Tyr Thr Arg Glu Pro Arg Asp Asp Arg Gly Ser Tyr Thr
225              230              235              240
Ala Ser Ile Tyr Gln Asn Tyr Met Gly Asn Ser Phe Ser Gly Tyr Ser
                245              250              255
His Ser Pro Pro Leu Leu Gln Val Asn Arg Ser Ser Asn Ser Pro
            260              265              270
Arg Thr Ser Glu Thr Asp Asp Gly Val Val Gly Lys Ser Ser Asp Gly
            275              280              285
Glu Asp Glu Gln Gln Val Pro Lys Gly Pro Ile His Ser Pro Val Glu
            290              295              300
Leu Lys His Val His Ala Thr Val Val Lys Val Pro Glu Val Asn Ser
305              310              315              320
Ser Ala Leu Pro His Lys Leu Arg Ile Lys Ala Lys Ala Met Gln Ile
                325              330              335
Lys Val Glu Ala Phe Asp Asn Glu Phe Glu Ala Thr Gln Lys Leu Ser
                340              345              350
Ser Pro Ile Asp Met Thr Ser Lys Arg His Phe Glu Leu Glu Lys His
            355              360              365
Ser Ala Pro Ser Met Val His Ser Ser Leu Thr Pro Phe Ser Val Gln
            370              375              380
Val Thr Asn Ile Gln Asp Trp Ser Leu Lys Ser Glu His Trp His Gln
385              390              395              400
Lys Glu Leu Ser Gly Lys Thr Gln Asn Ser Phe Lys Thr Gly Val Val
                405              410              415
Glu Met Lys Asp Ser Gly Tyr Lys Val Ser Asp Pro Glu Asn Leu Tyr
            420              425              430
Leu Lys Gln Gly Ile Ala Asn Leu Ser Ala Glu Val Val Ser Leu Lys
            435              440              445
Arg Leu Ile Ala Thr Gln Pro Ile Ser Ala Ser Asp Ser Gly
            450              455              460

<210> SEQ ID NO 3
<211> LENGTH: 2793
<212> TYPE: DNA
<213> ORGANISM: Homo sapiens

<400> SEQUENCE: 3
gggcacgagg cgctccctgg gatcacatgg tacctgctcc agtgccgcgt gcggcccggg    60
aaccctgggc tgctggcgcc tgcgcagagc cctctgtccc agggaaaggc tcgggcaaaa   120
ggcggctgag attggcagag tgaaatatta ctgccgaggg aacgtagcag ggcacacgtc   180
tcgcctcttt gcgactcggt gccccgtttc tccccatcac ctacttactt cctggttgca   240
acctctcttc ctctgggact tttgcaccgg gagctccaga ttcgccaccc cgcagcgctg   300
cggagccggc aggcagaggc accccgtaca ctgcagagac ccgaccctcc ttgctacctt   360
ctagccagaa ctactgcagg ctgattcccc ctacacactc tctctgctct tcccatgcaa   420
agcagaactc cgttgcctca acgtccaacc cttctgcagg gctgcagtcc ggccacccca   480
agaccttgct gcagggtgct tcggatcctg atcgtgagtc gcggggtcca ctccccgccc   540
```

```
ttagccagtg cccaggggc aacagcggcg atcgcaacct ctagtttgag tcaaggtcca    600
gtttgaatga ccgctctcag ctggtgaaga catgacgacc ctggactcca acaacaacac   660
aggtggcgtc atcacctaca ttggctccag tggctcctcc ccaagccgca ccagccctga   720
atccctctat agtgacaact ccaatggcag cttccagtcc ctgacccaag gctgtcccac   780
ctacttccca ccatccccca ctggctccct cacccaagac ccggctcgct cctttgggag   840
cattccaccc agcctgagtg atgacggctc cccttcttcc tcatcttcct cgtcgtcatc   900
ctcctcctcc ttctataatg ggagccccc tgggagtcta caagtggcca tggaggacag   960
cagccgagtg tcccccagca agagcaccag caacatcacc aagctgaatg catggtgtt  1020
actgtgtaaa gtgtgtgggg acgttgcctc gggcttccac tacggtgtgc acgcctgcga  1080
gggctgcaag ggcttttttcc gtcggagcat ccagcagaac atccagtaca aaggtgtct  1140
gaagaatgag aattgctcca tcgtccgcat caatcgcaac cgctgccagc aatgtcgctt  1200
caagaagtgt ctctctgtgg gcatgtctcg agacgctgtg cgttttgggc gcatccccaa  1260
acgagagaag cagcggatgc ttgctgagat gcagagtgcc atgaacctgg ccaacaacca  1320
gttgagcagc cagtgccgc tggagacttc acccacccag cacccacccc aggcccccat  1380
gggcccctcg ccaccccctg ctccggtccc ctcacccctg gtgggcttct cccagtttcc  1440
acaacagctg acgcctccca gatccccaag ccctgagccc acagtggagg atgtgatatc  1500
ccaggtggcc cgggccccatc gagagatctt cacctacgcc catgacaagc tgggcagctc  1560
acctggcaac ttcaatgcca accatgcatc aggtagccct ccagccacca ccccacatcg  1620
ctgggaaaat cagggctgcc cacctgcccc caatgacaac aacaccttgg ctgcccagcg  1680
tcataacgag gccctaaatg gtctgcgcca ggctcccctcc tcctacccctc ccacctggcc  1740
tcctggcccct gcacaccaca gctgccacca gtccaacagc aacgggcacc gtctatgccc  1800
cacccacgtg tatgcagccc cagaaggcaa ggcacctgcc aacagtcccc ggcagggcaa  1860
ctcaaagaat gttctgctgg catgtcctat gaacatgtac ccgcatggac gcagtgggcg  1920
aacggtgcag gagatctggg aggatttctc catgagcttc acgcccgctg tgcgggaggt  1980
ggtagagttt gccaaacaca tcccgggctt ccgtgacctt tctcagcatg accaagtcac  2040
cctgcttaag gctggcacct ttgaggtgct gatggtgcgc tttgcttcgt tgttcaacgt  2100
gaaggaccag acagtgatgt cctaagccg caccacctac agcctgcagg agcttggtgc  2160
catgggcatg ggagacctgc tcagtgccat gttcgacttc agcgagaagc tcaactccct  2220
ggcgcttacc gaggaggagc tgggcctctt caccgcggtg gtgcttgtct ctgcagaccg  2280
ctcgggcatg gagaattccg cttcggtgga gcagctccag gagacgctgc tgcgggctct  2340
tcgggctctg gtgctgaaga accggccctt ggagacttcc cgcttcacca agctgctgct  2400
caagctgccg gacctgcgga ccctgaacaa catgcattcc gagaagctgc tgtccttccg  2460
ggtggacgcc cagtgacccg cccggccggc cttctgccgc tgccccctgg tacagaatcg  2520
aactctgcac ttctctctcc tttacgagac gaaaaggaaa agcaaaccag aatcttattt  2580
atattgttat aaaatattcc aagatgagcc tctggccccc tgagccttct tgtaaatacc  2640
tgcctccctc ccccatcacc gaacttccc tcctcccta tttaaaccac tctgtctccc  2700
ccacaaccct cccctggccc tctgatttgt tctgttcctg tctcaaatcc aatagttcac  2760
agctgagctg gcttcaaaaa aaaaaaaaaa aaa                               2793
```

<210> SEQ ID NO 4
<211> LENGTH: 614

<212> TYPE: PRT
<213> ORGANISM: Homo sapiens

<400> SEQUENCE: 4

```
Met Thr Thr Leu Asp Ser Asn Asn Thr Gly Gly Val Ile Thr Tyr
1               5                   10                  15

Ile Gly Ser Ser Gly Ser Ser Pro Arg Thr Ser Pro Glu Ser Leu
                20                  25                  30

Tyr Ser Asp Asn Ser Asn Gly Ser Phe Gln Ser Leu Thr Gln Gly Cys
            35                  40                  45

Pro Thr Tyr Phe Pro Pro Ser Pro Thr Gly Ser Leu Thr Gln Asp Pro
        50                  55                  60

Ala Arg Ser Phe Gly Ser Ile Pro Pro Ser Leu Ser Asp Asp Gly Ser
65                  70                  75                  80

Pro Ser Ser Ser Ser Ser Ser Ser Ser Ser Ser Phe Tyr Asn
                85                  90                  95

Gly Ser Pro Pro Gly Ser Leu Gln Val Ala Met Glu Asp Ser Ser Arg
                100                 105                 110

Val Ser Pro Ser Lys Ser Thr Ser Asn Ile Thr Lys Leu Asn Gly Met
            115                 120                 125

Val Leu Leu Cys Lys Val Cys Gly Asp Val Ala Ser Gly Phe His Tyr
130                 135                 140

Gly Val His Ala Cys Glu Gly Cys Lys Gly Phe Phe Arg Arg Ser Ile
145                 150                 155                 160

Gln Gln Asn Ile Gln Tyr Lys Arg Cys Leu Lys Asn Glu Asn Cys Ser
                165                 170                 175

Ile Val Arg Ile Asn Arg Asn Arg Cys Gln Gln Cys Arg Phe Lys Lys
            180                 185                 190

Cys Leu Ser Val Gly Met Ser Arg Asp Ala Val Arg Phe Gly Arg Ile
        195                 200                 205

Pro Lys Arg Glu Lys Gln Arg Met Leu Ala Glu Met Gln Ser Ala Met
210                 215                 220

Asn Leu Ala Asn Asn Gln Leu Ser Ser Gln Cys Pro Leu Glu Thr Ser
225                 230                 235                 240

Pro Thr Gln His Pro Thr Pro Gly Pro Met Gly Pro Ser Pro Pro Pro
                245                 250                 255

Ala Pro Val Pro Ser Pro Leu Val Gly Phe Ser Gln Phe Pro Gln Gln
            260                 265                 270

Leu Thr Pro Pro Arg Ser Pro Ser Pro Glu Pro Thr Val Glu Asp Val
        275                 280                 285

Ile Ser Gln Val Ala Arg Ala His Arg Glu Ile Phe Thr Tyr Ala His
290                 295                 300

Asp Lys Leu Gly Ser Ser Pro Gly Asn Phe Asn Ala Asn His Ala Ser
305                 310                 315                 320

Gly Ser Pro Pro Ala Thr Thr Pro His Arg Trp Glu Asn Gln Gly Cys
                325                 330                 335

Pro Pro Ala Pro Asn Asp Asn Asn Thr Leu Ala Ala Gln Arg His Asn
            340                 345                 350

Glu Ala Leu Asn Gly Leu Arg Gln Ala Pro Ser Ser Tyr Pro Pro Thr
        355                 360                 365

Trp Pro Pro Gly Pro Ala His His Ser Cys His Gln Ser Asn Ser Asn
370                 375                 380

Gly His Arg Leu Cys Pro Thr His Val Tyr Ala Ala Pro Glu Gly Lys
385                 390                 395                 400
```

Ala Pro Ala Asn Ser Pro Arg Gln Gly Asn Ser Lys Asn Val Leu Leu
            405                 410                 415

Ala Cys Pro Met Asn Met Tyr Pro His Gly Arg Ser Gly Arg Thr Val
        420                 425                 430

Gln Glu Ile Trp Glu Asp Phe Ser Met Ser Phe Thr Pro Ala Val Arg
            435                 440                 445

Glu Val Val Glu Phe Ala Lys His Ile Pro Gly Phe Arg Asp Leu Ser
    450                 455                 460

Gln His Asp Gln Val Thr Leu Leu Lys Ala Gly Thr Phe Glu Val Leu
465                 470                 475                 480

Met Val Arg Phe Ala Ser Leu Phe Asn Val Lys Asp Gln Thr Val Met
            485                 490                 495

Phe Leu Ser Arg Thr Thr Tyr Ser Leu Gln Glu Leu Gly Ala Met Gly
        500                 505                 510

Met Gly Asp Leu Leu Ser Ala Met Phe Asp Phe Ser Glu Lys Leu Asn
        515                 520                 525

Ser Leu Ala Leu Thr Glu Glu Glu Leu Gly Leu Phe Thr Ala Val Val
    530                 535                 540

Leu Val Ser Ala Asp Arg Ser Gly Met Glu Asn Ser Ala Ser Val Glu
545                 550                 555                 560

Gln Leu Gln Glu Thr Leu Leu Arg Ala Leu Arg Ala Leu Val Leu Lys
            565                 570                 575

Asn Arg Pro Leu Glu Thr Ser Arg Phe Thr Lys Leu Leu Leu Lys Leu
        580                 585                 590

Pro Asp Leu Arg Thr Leu Asn Asn Met His Ser Glu Lys Leu Leu Ser
        595                 600                 605

Phe Arg Val Asp Ala Gln
    610

<210> SEQ ID NO 5
<211> LENGTH: 1740
<212> TYPE: DNA
<213> ORGANISM: Homo sapiens
<220> FEATURE:
<221> NAME/KEY: misc_feature
<222> LOCATION: (994)..(994)
<223> OTHER INFORMATION: n is a, c, g, or t

<400> SEQUENCE: 5

```
atggaggtga atgcaggagg tgtgattgcc tatatcagtt cttccagctc agcctcaagc      60
cctgcctctt gtcacagtga gggttctgag aatagtttcc agtcctcctc ctcttctgtt     120
ccatcttctc caaatagctc taattctgat accaatggta atcccaagaa tggtgatctc     180
gccaatattg aaggcatctt gaagaatgat cgaatagatt gttctatgaa acaagcaaa     240
tcgagtgcac ctgggatgac aaaaaatcat agtggtgtga caaaatttag tggcatggtt     300
ctactgtgta agtctgtgg ggatgtggcg tcaggattcc actatggagt tcatgcttgc     360
gaaggctgta agggtttctt tcggagaagt attcaacaaa acatccagta caagaagtgc     420
ctgaagaatg aaaactgttc tataatgaga atgaatagga acagatgtca gcaatgtcgc     480
ttcaaaaagt gtctgtctgt tggaatgtca agagatgctg ttcggtttgg tcgtattcct     540
aagcgtgaaa acagaggat gctaattgaa atgcaaagtg caatgaagac catgatgaac     600
agccagttca gtggtcactt gcaaaatgac acattagtag aacatcatga acagacagcc     660
ttgccagccc aggaacagct gcgacccaag ccccaactgg agcaagaaaa catcaaaagc     720
```

```
tcttctcctc catcttctga ttttgcaaag gaagaagtga ttggcatggt gaccagagct    780
cacaaggata cctttatgta taatcaagag cagcaagaaa actcagctga gagcatgcag    840
ccccagagag gagaacggat tcccaagaac atggagcaat ataatttaaa tcatgatcat    900
tgcggcaatg ggcttagcag ccattttccc tgtagtgaga gccagcagca tctcaatgga    960
cagttcaaag ggaggaatat aatgcattac ccanatggcc atgccatttg tattgcaaat   1020
ggacattgta tgaacttctc caatgcttat actcaaagag tatgtgatag agttccgata   1080
gatggatttt ctcagaatga aacaagaat agttacctgt gcaacactgg aggaagaatg   1140
catctggttt gtccaatgag taagtctcca tatgtggatc ctcataaatc aggacatgaa   1200
atctgggaag aattttcgat gagcttcact ccagcagtga aagaagtggt ggaatttgca   1260
aagcgtattc ctgggttcag agatctctct cagcatgacc aggtcaacct tttaaaggct   1320 gggactttg aggttttaat ggtacggttc gcatcattat ttgatgcaaa ggaacgtact   1380 gtcaccttt taagtggaaa gaaatatagt gtggatgatt tacactcaat gggagcaggg   1440
gatctgctaa actctatgtt tgaatttagt gagaagctaa atgccctcca acttagtgat   1500
gaagagatga gtttgtttac agctgttgtc ctggtatctg cagatcgatc tggaatagaa   1560
aacgtcaact ctgtggaggc tttgcaggaa actctcattc gtgcactaag gaccttaata   1620
atgaaaaacc atccaaatga ggcctctatt tttacaaaac tgcttctaaa gttgccagat   1680
cttcgatctt taacaacat gcactctgag gagctcttgg cctttaaagt tcacccttaa   1740
```

<210> SEQ ID NO 6  
<211> LENGTH: 578  
<212> TYPE: PRT  
<213> ORGANISM: Homo sapiens  
<220> FEATURE:  
<221> NAME/KEY: misc_feature  
<222> LOCATION: (332)..(332)  
<223> OTHER INFORMATION: Xaa can be any naturally occurring amino acid

<400> SEQUENCE: 6

```
Met Glu Val Asn Ala Gly Gly Val Ile Ala Tyr Ile Ser Ser Ser Ser
1               5                   10                  15

Ser Ala Ser Ser Pro Ala Ser Cys His Ser Glu Gly Ser Glu Asn Ser
            20                  25                  30

Phe Gln Ser Ser Ser Ser Val Pro Ser Ser Pro Asn Ser Ser Asn
        35                  40                  45

Ser Asp Thr Asn Gly Asn Pro Lys Asn Gly Asp Leu Ala Asn Ile Glu
    50                  55                  60

Gly Ile Leu Lys Asn Asp Arg Ile Asp Cys Ser Met Lys Thr Ser Lys
65                  70                  75                  80

Ser Ser Ala Pro Gly Met Thr Lys Asn His Ser Gly Val Thr Lys Phe
                85                  90                  95

Ser Gly Met Val Leu Leu Cys Lys Val Cys Gly Asp Val Ala Ser Gly
            100                 105                 110

Phe His Tyr Gly Val His Ala Cys Glu Gly Cys Lys Gly Phe Phe Arg
        115                 120                 125

Arg Ser Ile Gln Gln Asn Ile Gln Tyr Lys Lys Cys Leu Lys Asn Glu
    130                 135                 140

Asn Cys Ser Ile Met Arg Met Asn Arg Asn Arg Cys Gln Gln Cys Arg
145                 150                 155                 160

Phe Lys Lys Cys Leu Ser Val Gly Met Ser Arg Asp Ala Val Arg Phe
                165                 170                 175
```

```
Gly Arg Ile Pro Lys Arg Glu Lys Gln Arg Met Leu Ile Glu Met Gln
            180                 185                 190

Ser Ala Met Lys Thr Met Met Asn Ser Gln Phe Ser Gly His Leu Gln
        195                 200                 205

Asn Asp Thr Leu Val Glu His His Glu Gln Thr Ala Leu Pro Ala Gln
    210                 215                 220

Glu Gln Leu Arg Pro Lys Pro Gln Leu Glu Gln Glu Asn Ile Lys Ser
225                 230                 235                 240

Ser Ser Pro Pro Ser Asp Phe Ala Lys Glu Val Ile Gly Met
            245                 250                 255

Val Thr Arg Ala His Lys Asp Thr Phe Met Tyr Asn Gln Glu Gln Gln
                260                 265                 270

Glu Asn Ser Ala Glu Ser Met Gln Pro Gln Arg Gly Glu Arg Ile Pro
        275                 280                 285

Lys Asn Met Glu Gln Tyr Asn Leu Asn His Asp His Cys Gly Asn Gly
        290                 295                 300

Leu Ser Ser His Phe Pro Cys Ser Glu Ser Gln Gln His Leu Asn Gly
305                 310                 315                 320

Gln Phe Lys Gly Arg Asn Ile Met His Tyr Pro Xaa Gly His Ala Ile
                325                 330                 335

Cys Ile Ala Asn Gly His Cys Met Asn Phe Ser Asn Ala Tyr Thr Gln
            340                 345                 350

Arg Val Cys Asp Arg Val Pro Ile Asp Gly Phe Ser Gln Asn Glu Asn
        355                 360                 365

Lys Asn Ser Tyr Leu Cys Asn Thr Gly Gly Arg Met His Leu Val Cys
370                 375                 380

Pro Met Ser Lys Ser Pro Tyr Val Asp Pro His Lys Ser Gly His Glu
385                 390                 395                 400

Ile Trp Glu Glu Phe Ser Met Ser Phe Thr Pro Ala Val Lys Glu Val
                405                 410                 415

Val Glu Phe Ala Lys Arg Ile Pro Gly Phe Arg Asp Leu Ser Gln His
            420                 425                 430

Asp Gln Val Asn Leu Leu Lys Ala Gly Thr Phe Glu Val Leu Met Val
        435                 440                 445

Arg Phe Ala Ser Leu Phe Asp Ala Lys Glu Arg Thr Val Thr Phe Leu
450                 455                 460

Ser Gly Lys Lys Tyr Ser Val Asp Asp Leu His Ser Met Gly Ala Gly
465                 470                 475                 480

Asp Leu Leu Asn Ser Met Phe Glu Phe Ser Glu Lys Leu Asn Ala Leu
                485                 490                 495

Gln Leu Ser Asp Glu Glu Met Ser Leu Phe Thr Ala Val Val Leu Val
            500                 505                 510

Ser Ala Asp Arg Ser Gly Ile Glu Asn Val Asn Ser Val Glu Ala Leu
        515                 520                 525

Gln Glu Thr Leu Ile Arg Ala Leu Arg Thr Leu Ile Met Lys Asn His
530                 535                 540

Pro Asn Glu Ala Ser Ile Phe Thr Lys Leu Leu Leu Lys Leu Pro Asp
545                 550                 555                 560

Leu Arg Ser Leu Asn Asn Met His Ser Glu Glu Leu Leu Ala Phe Lys
                565                 570                 575

Val His
```

<210> SEQ ID NO 7

```
<211> LENGTH: 20
<212> TYPE: DNA
<213> ORGANISM: Artificial Sequence
<220> FEATURE:
<223> OTHER INFORMATION: forward primer A for detection of E4bp4
      wildtype allele

<400> SEQUENCE: 7
ctctgagctt ggctgatgtg                                              20

<210> SEQ ID NO 8
<211> LENGTH: 20
<212> TYPE: DNA
<213> ORGANISM: Artificial Sequence
<220> FEATURE:
<223> OTHER INFORMATION: reverse primer for the detection of E4bp4

<400> SEQUENCE: 8
gcttcaagtc tccaccaagc                                              20

<210> SEQ ID NO 9
<211> LENGTH: 20
<212> TYPE: DNA
<213> ORGANISM: Artificial Sequence
<220> FEATURE:
<223> OTHER INFORMATION: primer for the detection of the E4bp4 null
      allele

<400> SEQUENCE: 9
ccatgctcct gtcttgatga                                              20
```